US008361806B2

(12) United States Patent
Gjerde et al.

(10) Patent No.: US 8,361,806 B2
(45) Date of Patent: Jan. 29, 2013

(54) OPEN CHANNEL SOLID PHASE EXTRACTION SYSTEMS AND METHODS

(75) Inventors: Douglas T. Gjerde, Saratoga, CA (US); Christopher T. Hanna, San Francisco, CA (US)

(73) Assignee: PhyNexus, Inc., San Jose, CA (US)

( * ) Notice: Subject to any disclaimer, the term of this patent is extended or adjusted under 35 U.S.C. 154(b) by 0 days.

(21) Appl. No.: 12/986,102

(22) Filed: Jan. 6, 2011

(65) Prior Publication Data

US 2011/0118452 A1    May 19, 2011

Related U.S. Application Data

(63) Continuation of application No. 10/733,534, filed on Dec. 10, 2003, now Pat. No. 7,879,621, which is a continuation-in-part of application No. 10/434,713, filed on May 8, 2003, now abandoned.

(60) Provisional application No. 60/523,518, filed on Nov. 18, 2003.

(51) Int. Cl.
| | |
|---|---|
| G01N 1/18 | (2006.01) |
| G01N 30/96 | (2006.01) |
| G01N 30/04 | (2006.01) |
| G01N 30/14 | (2006.01) |
| G01N 30/40 | (2006.01) |
| G01N 30/84 | (2006.01) |
| G01N 33/68 | (2006.01) |

(52) U.S. Cl. .......... 436/178; 422/68.1; 422/69; 422/70; 422/500; 422/507; 436/86; 436/87; 436/174; 436/177

(58) Field of Classification Search .......... 422/68.1–70, 422/500, 527; 436/86–87, 174, 177–178, 436/500–548
See application file for complete search history.

(56) References Cited

U.S. PATENT DOCUMENTS

| | | | | |
|---|---|---|---|---|
| 3,097,927 | A * | 7/1963 | Skeggs | 436/53 |
| 4,028,056 | A * | 6/1977 | Snyder et al. | 436/514 |
| 4,186,187 | A * | 1/1980 | Jahnsen et al. | 422/64 |
| 4,221,568 | A * | 9/1980 | Boettger | 436/48 |
| 4,361,509 | A * | 11/1982 | Zimmerman et al. | 530/383 |
| 4,810,381 | A * | 3/1989 | Hagen et al. | 210/502.1 |
| 4,877,830 | A * | 10/1989 | Dobeli et al. | 525/54.3 |
| 4,882,275 | A * | 11/1989 | Klagsbrun | 435/70.3 |
| 4,923,978 | A * | 5/1990 | McCormick | 536/25.4 |
| 5,017,540 | A * | 5/1991 | Sandoval et al. | 502/158 |
| 5,284,755 | A * | 2/1994 | Gearing et al. | 435/69.1 |
| 5,518,914 | A * | 5/1996 | Buck et al. | 435/384 |
| 5,565,622 | A * | 10/1996 | Murphy | 73/61.55 |
| 5,833,927 | A * | 11/1998 | Raybuck et al. | 422/513 |
| 5,919,368 | A * | 7/1999 | Quinn et al. | 210/635 |
| 5,962,641 | A * | 10/1999 | Nelson et al. | 530/344 |
| 6,033,903 | A * | 3/2000 | Sisk et al. | 435/320.1 |
| 6,034,223 | A * | 3/2000 | Maddon et al. | 530/391.7 |
| 6,048,457 | A * | 4/2000 | Kopaciewicz et al. | 210/321.6 |
| 6,149,815 | A * | 11/2000 | Sauter | 210/635 |
| 6,416,716 | B1 * | 7/2002 | Shukla et al. | 422/527 |
| 6,429,192 | B1 * | 8/2002 | Laursen | 514/20.9 |
| 6,432,290 | B1 * | 8/2002 | Harrison et al. | 204/453 |
| 6,783,680 | B2 * | 8/2004 | Malik | 210/635 |

(Continued)

OTHER PUBLICATIONS

Smith, M. C. et al, Inorganic Chemistry 1987, 26, 1965-1969.*

(Continued)

*Primary Examiner* — Arlen Soderquist
(74) *Attorney, Agent, or Firm* — Sue S. Kalman

(57) ABSTRACT

The invention provides, inter alia, methods, devices and reagents for the preparation of native and non-denatured biomolecules using solid-phase extraction channels. The invention is particularly suited for the purification, concentration and/or analysis of protein analytes. The invention further provides, inter alia, methods, devices and reagents for the purification, concentration and/or analysis of multi-protein complexes.

14 Claims, 13 Drawing Sheets

U.S. PATENT DOCUMENTS

| | | | | |
|---|---|---|---|---|
| 6,887,384 | B1* | 5/2005 | Frechet et al. | 210/634 |
| 7,122,640 | B2* | 10/2006 | Gjerde et al. | 530/412 |
| 7,151,167 | B2* | 12/2006 | Gjerde et al. | 530/412 |
| 7,879,621 | B2* | 2/2011 | Gjerde et al. | 436/178 |
| 2001/0029024 | A1* | 10/2001 | Kodadek | 435/7.1 |
| 2002/0147326 | A1* | 10/2002 | Chaikin et al. | 536/23.5 |
| 2002/0158022 | A1* | 10/2002 | Huang et al. | 210/656 |
| 2002/0161014 | A1* | 10/2002 | Sadhu et al. | 514/266.2 |
| 2003/0003108 | A1* | 1/2003 | Fong et al. | 424/189.1 |
| 2003/0007897 | A1* | 1/2003 | Creasey | 422/100 |
| 2003/0032070 | A1* | 2/2003 | Good et al. | 435/7.21 |
| 2003/0099608 | A1* | 5/2003 | Presnell et al. | 424/85.1 |
| 2003/0176651 | A1* | 9/2003 | Grant et al. | 530/350 |
| 2003/0207791 | A1* | 11/2003 | Minucci et al. | 514/1 |
| 2004/0029195 | A1* | 2/2004 | Shiekhattar | 435/7.23 |
| 2004/0126890 | A1* | 7/2004 | Gjerde et al. | 436/53 |
| 2004/0171034 | A1* | 9/2004 | Agnew et al. | 435/6 |
| 2004/0223880 | A1* | 11/2004 | Gjerde et al. | 422/70 |
| 2004/0224362 | A1* | 11/2004 | Gjerde et al. | 435/7.1 |
| 2004/0224425 | A1* | 11/2004 | Gjerde et al. | 436/518 |
| 2004/0241721 | A1* | 12/2004 | Gjerde et al. | 435/6 |
| 2005/0106585 | A1* | 5/2005 | Gjerde et al. | 435/6 |
| 2005/0118646 | A1* | 6/2005 | Boniface et al. | 435/7.1 |
| 2007/0036685 | A1* | 2/2007 | Bakry et al. | 422/101 |
| 2007/0196833 | A1* | 8/2007 | Gjerde | 435/6 |

OTHER PUBLICATIONS

Hochuli, E., Journal of Chromatography 1988, 444, 293-302.*
Chicz, R. M. et al, Analytical Chemistry 1989, 61, 1742-1749.*
Geogoussi, Z. et al, Biochimica et Biophysica Acta 1990, 1055, 69-74.*
Bonn, G. K. et al, Chromatographia 1990, 30, 484-488.*
Siemens, I. R. et al, Journal of Neurochemistry 1994, 62, 257-264.*
Cole, L. J. et al, Electrophoresis 1995, 16, 549-556.*
Vunnum, S. et al, Chemical Engineering Science, 1995, 50, 1785-1803.*
Sardana, V. et al, Methods in Enzymology, 1996, 275, 3-16.*
Fan, N. et al, Biochemistry 1996, 35, 1911-1917.*
van Sommeren, A. P. G. et al, Journal of Virological Methods, 1997, 63, 37-46.*
Luciano, P. et al, Journal of Molecular Biology 1997, 272, 213-225.*
Betts, J. C. et al, Journal of Biological Chemistry 1997, 272, 12922-12927.*
Schmid, E. L. et al, Analytical Chemistry 1998, 70, 1331-1338.*
Roy, R. S. et al, Biochemistry 1998, 37, 4125-4136.*
Zhen, Y. et al, Protein Expression and Purification 1998, 13, 326-336.*
Dall'Acqua, W. et al, Biochemistry 1998, 37, 9266-9273.*
Goodwin, P. J. et al, Biochemistry 1998, 37, 10420-10428.*
Christiansen, J. et al, Biochemistry 1998, 37, 12611-12623.*
Grob, P. et al, Immunotechnology 1998, 4, 155-163.*
Heegaard, N. H. H. et al, Journal of Chromatography B 1998, 715, 29-54.*
Gobom, J. et al, Journal of Mass Spectrometry 1999, 34, 105-116.*
deCastro, M. J. et al, Biochemistry 1999, 38, 5076-5081.*
Tong, W. et al, Analytical Chemistry 1999, 71, 2270-2278.*
Nordhoff, E. et al, Nature Biotechnology 1999, 17, 884-888.*
Bonneil, E. et al, Journal of Chromatography B 1999, 736, 273-287.*
Bornhorst, J. A. et al, Methods in Enzymology 2000, 326, 245-254.*
Merchant, M. et al, Electrophoresis 2000, 21, 1164-1167.*
Prutsch, A. et al, Biochemistry 2000, 39, 6554-6563.*
Chan, J. M. et al, Biochemistry 2000, 39, 7221-7228.*
Yoshikawa, D. M. et al, Biochemistry 2000, 39, 11340-11347.*
Bratton, M. R. et al, Biochemistry 2000, 39, 12989-12995.*
Hafner, F. T. et al, Analytical Chemistry 2000, 72, 5779-5786.*
Bundy, J. L. et al, Analytical Chemistry 2001, 73, 751-757.*
Amarasinghe, A. K. et al, Methods in Enzymology 2001, 342, 143-158.*
Chaga, G. S., Journal of Biochemical and Biophysical Methods 2001, 49, 313-334.*
Mateo, C. et al, Journal of Chromatography A 2001, 915, 97-106.*
Lee, Y.-T. et al, Biochemistry 2001, 40, 6836-6844.*
Liu, B.-F. et al, Journal of Chromatography A 2001, 918, 401-409.*
Yu, C. et al, Analytical Chemistry 2001, 73, 5088-5096.*
Yu, B. et al, Biochemistry 2001, 40, 15581-15590.*
Gururaja, T. et al, Journal of Proteome Research 2002, 1, 253-261.*

* cited by examiner

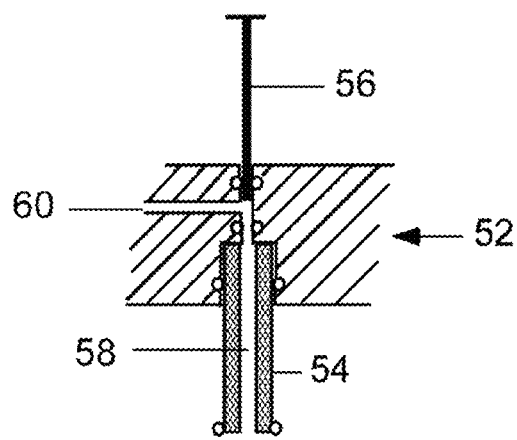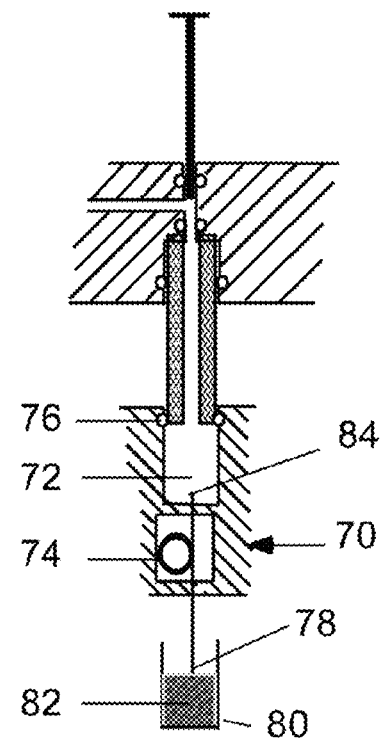
*FIG.-7A*   *FIG.-7B*

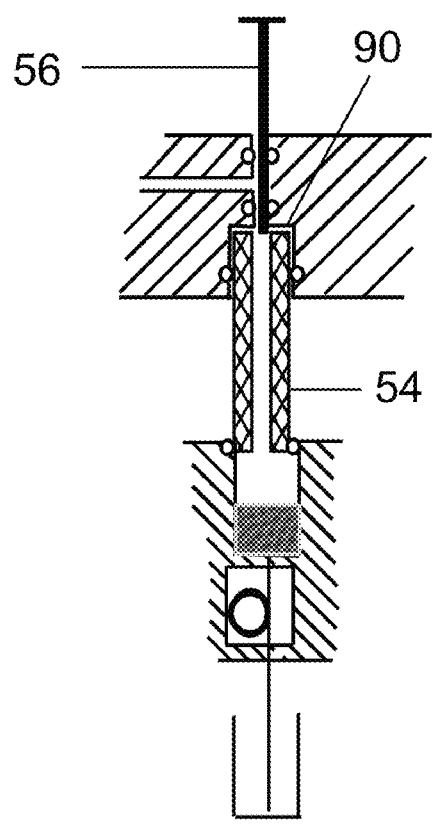 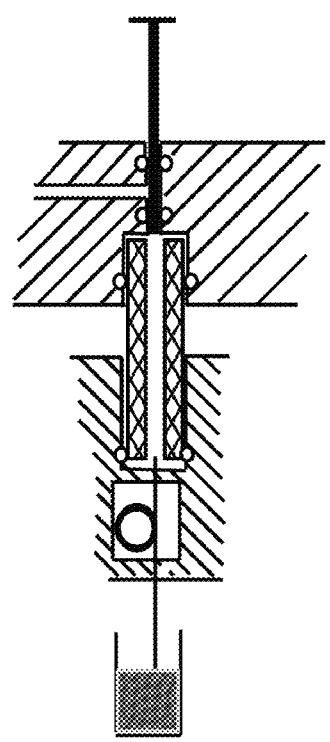
*FIG.-7C*        *FIG.-7D*

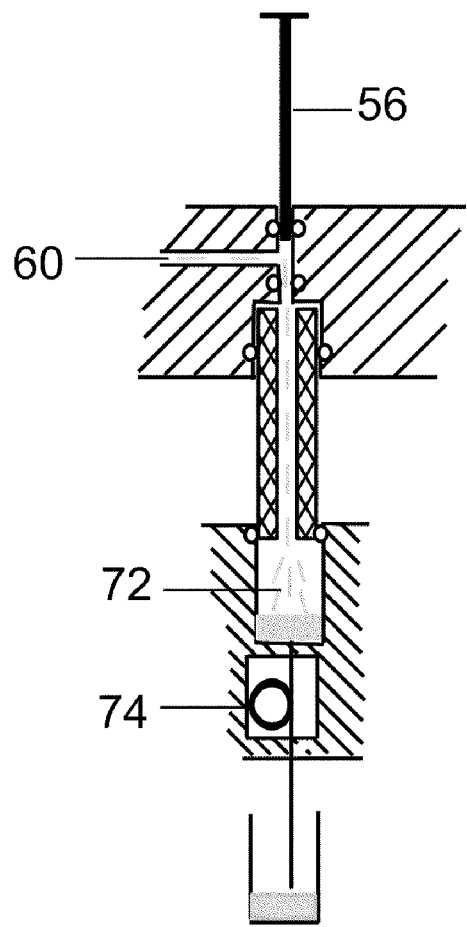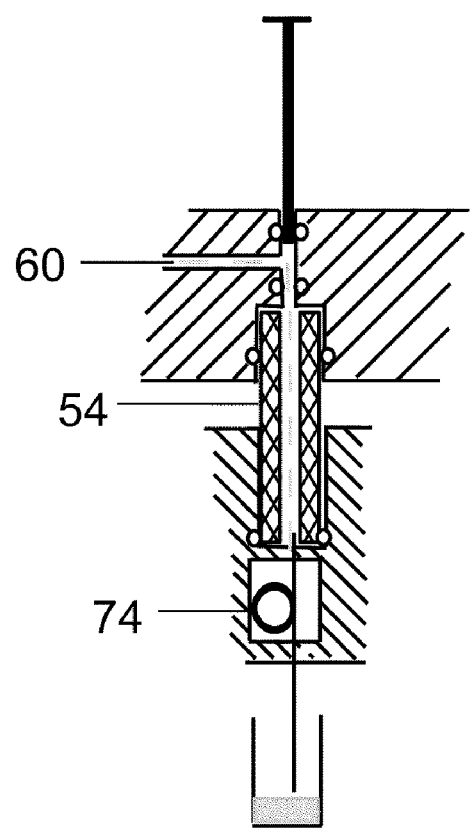
*FIG.-7E*  *FIG.-7F*

OPEN CHANNEL SOLID PHASE EXTRACTION SYSTEMS AND METHODS

CROSS-REFERENCE TO RELATED APPLICATIONS

This patent application is a continuation of U.S. patent application Ser. No. 10/733,534, filed Dec. 10, 2003, now U.S. Pat. No. 7,879,621, which is a continuation-in part of U.S. patent application Ser. No. 10/434,713, filed May 8, 2003, now abandoned, which claims priority to U.S. Provisional Patent Application No. 60/523,518, filed Nov. 18, 2003, the disclosures of which are incorporated herein by reference in their entirety for all purposes.

FIELD OF THE INVENTION

This invention relates to devices and methods for performing solid phase extractions in an open channel device, e.g., an extraction capillary. In some embodiments the invention is used for purifying, separating and/or concentrating an analyte. The analytes can be biomolecules or biomolecule complexes, including biological macromolecules such as polypeptides, polynucleotides, and/or polysaccharides.

BACKGROUND OF THE INVENTION

Solid phase extraction has been used to extract analytes from water and other liquids to prepare them for analysis. For example, the technique has found success in monitoring drinking water by extraction of organics from the water followed by high pressure liquid chromatography separation and mass spectrometry (MS) detection to determine the identity and concentration of pollutants. Proteins and nucleic acid materials are frequently isolated from biological samples by passing them through a packed column and cartridge containing a solid phase where the molecules of interest are adsorbed. After the sample has passed through the column and the sample molecules have been adsorbed, a solvent is used to desorb the molecules of interest and form a concentrated solution.

It is particularly important to be able to purify and concentrate non-polynucleotide biomolecules such as polypeptides and polysaccharides, since these molecules are not amenable to the types of amplification techniques routinely used with nucleic acids. Many proteins and peptides are only expressed at extremely low levels, and in the presence of a vast excess of contaminating proteins and other cellular constituents. For this reason, it is often necessary to purify and concentrate a protein sample of interest prior to performing analytical techniques such as MS, SPR, NMR, X-ray crystallography and the like. These techniques typically only require a small volume of sample, but it must be presented at a sufficiently high concentration and interfering contaminants should be removed. Hence, there is a need for sample preparation methods that permit the manipulation and processing of small sample volumes with minimal sample loss.

Other desirable attributes of a sample preparation technology are the ability to purify and manipulate protein complexes. In many applications, it is also critical that the purified protein retain its native function.

Methods and reagents for performing solid phase extractions in open channels, such as open capillaries, are described in co-pending U.S. patent application Ser. No. 10/434,713. The instant disclosure follows up on that application, providing in some instances more specific and detailed teaching for performing open channel solid phase extractions. These methods, and the related devices and reagents, will be of particular interest to the life scientist, since they provide a powerful technology for purifying, concentrating and analyzing biomolecules and other analytes of interest. However, the methods, devices and reagents are not limited to use in the biological sciences, and can find wide application in a variety of preparative and analytical contexts.

SUMMARY OF THE INVENTION

The subject invention pertains to solid phase extraction channels, and methods of using the same for extracting an analyte from solution. In some embodiments, the open channel is a capillary, i.e., an extraction capillary. Certain embodiments of the invention are particularly suited to the processing of biological samples, where the analyte of interest is a biomolecule. Of particular relevance are biological macromolecules such as polypeptides, polynucleotides, and polysaccharides, or large complexes containing one or more of these moieties. The biomolecule can be part of a larger structure, such as a biomolecule complex, an organelle, a virus, a cell or a membrane.

In general, the methods involve introducing a sample solution containing the analyte of interest into the extraction channel in a manner that permits the analyte to interact with and adsorb to an extraction surface coating the surface of the channel. The adsorbed analyte is then eluted in a desorption solution. Optionally, the extraction channel is washed one or more times prior to introduction of the desorption solution. The desorbed analyte can be collected, and is typically analyzed by any of a number of techniques, some of which are described in more detail below. The extraction process generally results in the enrichment, concentration, and/or purification of an analyte or analytes of interest.

In general, the methods involve introducing a sample solution containing the analyte of interest into the extraction channel in a manner that permits the analyte to interact with and adsorb to an extraction surface coating the surface of the channel. The adsorbed analyte is then eluted in a desorption solution. Optionally, the extraction channel is washed one or more times prior to introduction of the desorption solution. The desorbed analyte can be collected, and is typically analyzed by any of a number of techniques, some of which are described in more detail below. The extraction process generally results in the enrichment, concentration, and/or purification of an analyte or analytes of interest.

In some embodiments of the invention, bulk liquid is purged from the extraction channel prior to elution of the analyte, e.g., by blowing gas through the capillary. In some embodiments the extraction surface of the capillary is not dried by the purging, but remains hydrated or solvated. In other embodiments, the purging is more complete, resulting in partial or even substantial dehydration or desolvation of the extraction surface and/or analyte.

In another embodiment, the invention provides an extraction channel containing a bound analyte, where the extraction channel is substantially free of bulk liquid, e.g., as the result of a purge step. While substantially free of bulk solution, the analyte and/or extraction surface can be fully hydrated. In other embodiments, the extraction surface and/or analyte are partially or substantially dehydrated or desolvated.

In some embodiments, the amount of desorption solution used is less than the volume of the channel, i.e., the process is characterized by a tube enrichment factor of greater than one. In the context of open channel solid phase extraction, the term "tube enrichment factor," or "TEF," is defined as the ratio of the volume of an extraction channel to the volume of a liquid segment of desorption solvent used to desorb an analyte from the extraction surface. TEF is a component of the total enrichment of the sample. The total enrichment factor of the sample can be increased even further by processing a volume of sample solution that exceeds the volume of the channel. In the context of open channel solid phase extraction, the term "enrichment factor, (or "total enrichment factor") is defined as the ratio of the volume of a sample containing an analyte that is passed through (i.e, loaded onto or processed by) an extraction channel to the volume of desorption solvent used to desorb the analyte from the extraction surface.

In some embodiments of the invention, very small volumes of desorption solvent are employed. In another aspect, the invention provides methods of collecting very small fractions of desorbed sample, which might constitute the entire volume of desorption solution used or some fraction thereof. While many of the extraction devices of the invention are capable of providing purified analyte in a very small volume of liquid, they are also able (in many cases) to process relatively large original sample volumes, resulting in high enrichment factors.

It is possible to repeatedly expose the sample, wash and desorption solvent to the extraction surface (e.g., by simply moving it back and forth through the channel). In the case of sample, this can mean greater extraction efficiencies and hence greater recoveries. In the case of desorption solvent, this can translate into dramatically reduced desorption volume, resulting in a more enriched desorbed sample. Concentrations of the sample can be increased by using only a small slug of desorbing solvent that passes back and forth over the stationary phase before it is deposited from the channel to the target.

In some embodiments of the invention a solid-phase extraction chemistry attached to the inner surface of the channel is used to extract an analyte of interest from solution. The solid-phase extraction surface can take any of a wide variety of forms. For example, the extraction surface can be selected from, or based on, any of the extraction chemistries used in solid-phase extraction and/or chromatography, e.g., reverse-phase, normal phase, hydrophobic interaction, hydrophilic interaction, ion-exchange or affinity binding. Because the invention is particularly suited to the purification and/or concentration of biomolecules, extraction surfaces capable of adsorbing such molecules are particularly relevant. The extraction surface can be a monolayer, or can take the form of a 3-dimensional extraction matrix.

Extraction channels and associated methods of the invention find particular utility in preparing samples of analyte for analysis or detection by a variety analytical techniques. It is particularly useful for use with techniques that require small volumes of pure, concentrated analyte. In many cases, the results of these forms of analysis are improved by increasing analyte concentration. The methods are particular suited for use with label-free detection methods or methods that require functional, native (i.e., non-denatured protein), but are generally useful for any protein or nucleic acid of interest. Examples of applicable analytical techniques include MS, X-ray crystallography, SPR, biochips (e.g., protein chips), mictocantilever detection schemes, microcalorimetry, acoustic wave sensors, atomic force microscopy, scanning force microscopy, quartz crystal microweighing, and optical waveguide lightmode spectroscopy (OWLS), physical labeling, fluorescent tagging, planar waveguide imaging, optical biosensors, nanoarray technology, activity-based protein profiling, kinetic exclusion assays, surface immobilized assays, immunological assays, various ligand displacement/competition assays, direct genetic tests, biophysical methods, direct force measurements, NMR, electron microscopy (including cryo-EM) and IR.

In some embodiments of the invention, a plurality of channels (e.g., capillaries) are operated in parallel, i.e., in a multiplex fashion. In some embodiments, the invention provides a multiplexed extraction system comprising a plurality of extraction channels of the invention, e.g., fused silica extraction capillaries. The system can include a pump or pumps in operative engagement with the extraction channels, useful for pumping fluid through the capillaries in a multiplex fashion, i.e., concurrently. In some embodiments, each capillary is addressable.

In one embodiment, sample can be arrayed from an extraction capillary to a plurality of predetermined locations, for example locations on a chip or microwells in a multi-well plate.

The extraction process can be automated, for example by using software to program the computer controller to control the pumping, e.g., the volumes, flow rates, delays, and number of cycles.

The invention also provides software for implementing the methods of the invention. For example, the software can be programmed to control manipulation of solutions and addressing of capillaries into sample vials, collection vials, for spotting or introduction into some analytical device for further processing.

The invention also includes kits comprising one or more reagents and/or articles for use in a process relating to solid-phase extraction, e.g., buffers, standards, solutions, capillaries, sample containers, etc.

In some embodiments of the invention, desorption solvent gradients, step elutions and/or multidimensional elutions are performed. Gradients used in the context of the invention can be continuous or step. In some embodiments of the invention a multidimensional stepwise solid phase extraction process is employed.

In some embodiments, an extraction channel is used to purify entire classes of proteins on the basis of highly conserved motifs within their structure, whereby an affinity binding agent is used that reversibly binds to the conserved motif. Exemplary affinity binding agents include nucleotides, lectins, antibodies, protein interaction domains, dyes, synthetics peptides and peptide analogs, and other biomolecules and biomimetics.

In certain embodiments, extraction capillaries of the invention are used to extract and/or process multi-protein complexes. In some embodiments, multi-protein complex is adsorbed to the extraction surface and desorbed under conditions such that the integrity of the complex is retained throughout. In another embodiment, the extraction capillaries of the invention can be used as a tool to analyze the nature of the complex. For example, the protein complex is sorbed to the extraction surface, and the state of the complex is then monitored as a function of solvent variation. In one embodiment, a series of two or more desorption solvents is used sequentially, and the eluent is monitored to determine which protein constituents come off in a particular solvent.

In one embodiment, the capillary extraction devices and methods of the invention are used to purify proteins that are active (functional) and/or in their native state, i.e., non-denatured. This is accomplished by performing the extraction process under non-denaturing conditions.

In certain embodiments, an extraction channel can function not only as a separation device, but also as a means for collecting, transporting, storing and or dispensing a liquid sample. For example, in one embodiment the extraction capillary is used as a sample collection device, e.g., a sample collection needle. In another embodiment, an extraction capillary is transportable to the site where the eluted sample is destined, e.g., a storage vessel or an analytical instrument. In some embodiments of the invention involving transportable capillary or capillary devices, the entire capillary is transported, e.g., on the end of a syringe, or just the bare capillary or a portion thereof. In other cases, one end of the capillary remains attached to a stationary instrument or device and the other end is transportable, e.g., the end can be moved to ionization chamber or to predetermined location for spotting on solid substrate.

In some embodiments of the invention, sample is processed in the extraction capillary itself, e.g., a cell or virus is adsorbed by the extraction channel and lysed or otherwise processed in the capillary itself.

In some embodiments, the invention is used to change the composition of a solution in which an analyte is present. An example is the desalting of a sample, where some or substantially all of the salt (or other constituent) in a sample is removed or replaced by a different salt (or non-salt constituent). The removal of potentially interfering salt from a sample prior to analysis is important in a number of analytical techniques, e.g., mass spectroscopy.

BRIEF DESCRIPTION OF THE FIGURES

FIGS. 7A-J depict a section of a multiplexed capillary extraction apparatus in various stages of the extraction process.

DESCRIPTION OF SPECIFIC EMBODIMENTS OF THE INVENTION

Figure 1:
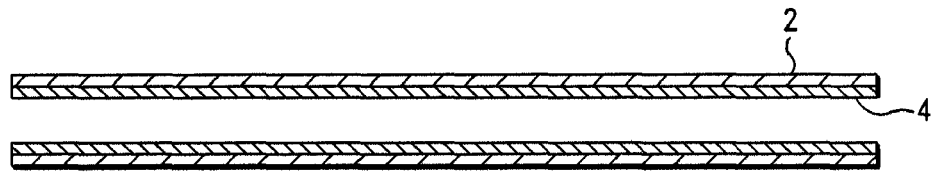
FIGS. 1-4 are schematic drawings exemplifying the operation of an extraction channel.

In accordance with the present invention there may be employed conventional chemistry, biological and analytical techniques within the skill of the art. Such techniques are explained fully in the literature. See, e.g. *Chromatography*, 5$^{th}$ edition, PART A: FUNDAMENTALS AND TECHNIQUES, editor: E. Heftmann, Elsevier Science Publishing Company, New York (1992); ADVANCED CHROMATOGRAPHIC AND ELECTROMIGRATION METHODS IN BIOSCIENCES, editor: Z. Deyl, Elsevier Science BV, Amsterdam, The Netherlands, (1998); CHROMATOGRAPHY TODAY, Colin F. Poole and Salwa K. Poole, and Elsevier Science Publishing Company, New York, (1991).

The subject invention pertains to solid phase extraction channels, and methods of using the same for extracting an analyte from solution. In some embodiments these extraction channels are open, that is, they are not packed with resin or other forms of chromatographic beads used in conventional chromatography. Rather, the channel is open and the extraction phase consists of an extraction surface bound either directly or non-directly to the channel surface. The extraction process involves flowing solvent, such as sample solvent, desorption solvent, and optionally a wash solvent, through the open channel, or some portion of the channel. In some preferred embodiments, the open channel is a capillary, i.e., an extraction capillary.

In preferred embodiments, the extraction surface covers the entire inner periphery of the extraction channel, as opposed to on just one face of the channel. Thus, even if only some section of the entire length of the capillary is coated with the extraction surface, in that section substantially the entire periphery is covered with the extraction surface. This is to be distinguished from, e.g., a channel in a microfluidic chip or device that has an extraction surface only on one face of the channel.

Methods of the invention typically involve adsorbing an analyte of interest from a sample solution onto the extraction surface of a solid-phase extraction channel, substantially evacuating the sample solution while leaving the adsorbed analyte bound to the extraction surface, and eluting the analyte from the channel in a desorption solution. The desorbed analyte can be collected, and is typically analyzed by any of a number of techniques, some of which are described in more detail below. In some embodiments the extraction surface is washed prior to elution. The extraction process generally results in the enrichment, concentration, and/or purification of an analyte or analytes of interest.

In conventional packed columns there are typically regions (i.e., volumes) that are not swept by solvent passing through the column, which results in sample loss. One advantage of the use of open channels as opposed to conventional packed columns is that unswept volumes can be substantially minimized or eliminated, thus dramatically minimizing or eliminating sample losses associated with such unswept volumes. Minimal unswept volumes allow the introduction, control and collection of defined volumes of liquid that can contain the analyte of interest. The tube or capillary channel must have the property of allowing movement and removal of liquid. In this respect, the tube could contain secondary structures, including roughness and protrusions or even beads or monolith structure as long as the channels that are formed in the secondary structure do not result in unswept volumes that substantially impact performance. A reference (Ronald Majors, 2002 Pittsburgh Conference, Part I, LC/GC Europe, April 2002, pp 2-15) gives details on encapsulated and monolith structures.

Certain embodiments of the invention are particularly suited to the processing of biological samples, where the analyte of interest is a biomolecule. Of particular relevance are biological macromolecules such as polypeptides, polynucleotides, and polysaccharides, or large complexes containing on or more of these moieties.

Because of the nature of the flow path in an open channel of the invention, it is possible to capture, purify and concentrate molecules or groups of molecules that have a relatively large structure compared even to a protein. An extraction channel with the appropriate binding functionality on the surface can bind and extract these structure without problems such as shearing or (frit or backed bed) filtration, that can occur with conventional extraction columns. Care does have to be taken when introducing the solution to the capillary channel or when flowing solutions through the capillary channel so that the structure is not sheared. Slower flow rates may be necessary. Examples of large structures that can be extracted are protein complexes, viruses and even whole cells that can be captured by a specific surface group.

Extraction Methods

In various embodiments, the subject invention provides methods for using solid-phase extraction channels (such as capillaries) to extract, purify, process and/or concentrate an analyte or analtyes of interest. The invention is particularly suited for the preparation of biomolecule analytes, especially biological macromolecules, including biomolecule complexes. Because of the nature of the capillaries, which are not as susceptible to clogging, unswept dead volumes or sample loss as conventional packed chromatography columns, they can be used for processing very large biological complexes, including large multiprotein complexes such as ribosomes, transcription complexes, proteasomes, etc., as well a organelles, membranes, viruses and whole cells.

In general, the methods involve introducing a sample solution containing the analyte of interest into the extraction channel in a manner that permits the analyte to interact with and adsorb to the extraction surface. The sample solution enters the channel through one end, and passes through the channel or some portion of the entire length of the channel, eventually exiting the channel through either the same end of the channel or out the other end. Introduction of the sample solution into the channel can be accomplished by any of a number of techniques for driving or drawing liquid through a channel. Examples would include use of a pump (e.g., a syringe, pressurized container, centrifugal pump, electrokinetic pump, or an induction based fluidics pump), gravity, centrifugal force, capillary action, or gas pressure to move fluid through the capillary. The sample solution is preferably moved through the channel at a flow rate that allows for adequate contact time between the sample and extraction surface. The sample solution can be passed through the capillary more than one time, either by circulating the solution through the channel in the same direction two or more times, or by passing the sample back and forth through the channel two or more times (e.g., by oscillating a plug or series of plugs of desorption solution in the channel). In some embodiments it is important that the pump be able to pump air, thus allowing for liquid to be blown out of the channel. Preferred pumps have good precision, good accuracy and minimal hysteresis, can manipulate small volumes, and can be directly or indirectly controlled by a computer or other automated means, such that the pump can be used to aspirate, infuse and/or manipulate a predetermined volume of liquid. The required accuracy and precision of fluid manipulation in the channel will vary depending on the step in the extraction procedure, the enrichment of the biomolecule desired, and the dimensions of the capillary. For example, for a capillary with dimensions of 200 µm id and 1 m in length, the internal volume is approximately 33 µL. A liquid slug of 10% of the capillary volume represents a 3.3 µL volume and a 10 cm length. Movement of the slug to within 2% of each end of the capillary means the slug should be within 4 cm of each end. Accuracy of dispensing the slug depends on the volume to be dispensed. Expelling the entire slug requires less accuracy than expelling only part of the slug. If 10% of the slug is expelled then, the slug must be moved to the end of the capillary (within a few mm) and then 1 cm of the slug is expelled or deposited to the target.

Thus, for example, in one embodiment an end of an extraction channel is attached to a syringe pump and the other end is positioned in a sample solution. The syringe plunger is pulled up to draw the sample solution into and through the channel. The sample can be drawn through the entire length of the channel, and optionally into the chamber of the syringe. The ability to draw liquid into the syringe is particularly relevant when the sample volume exceeds the volume of the channel. Once the entire volume of sample to be processed has been drawn into the channel and/or syringe chamber, and optionally after some incubation period where the sample is allowed to set in the syringe and/or channel, the syringe plunger is pushed down, driving the sample solution back through the channel and out through the same end from which it entered. At this point, the sample has passed through the capillary twice, once in each direction. If desired, for example to increase interaction of analyte with extraction surface and to increase the amount of adsorbed analyte, the drawing in and driving out of the sample solution can be repeated. Sample can be taken up into syringe chamber when the sample volume exceeds the volume of the channel. Once the entire volume of sample to be processed has been drawn into the channel and/or syringe chamber, and optionally after some incubation period where the sample is allowed to set in the syringe and/or channel, the syringe plunger is pushed down, driving the sample solution back through the channel and out through the same end from which it entered. At this point, the sample has passed through the capillary twice, once in each direction. If desired, for example to increase interaction of analyte with extraction surface and to increase the amount of adsorbed analyte, the drawing in and driving out of the sample solution can be when the sample volume exceeds the volume of the channel. Once the entire volume of sample to be processed has been drawn into the channel and/or syringe chamber, and optionally after some incubation period where the sample is allowed to set in the syringe and/or channel, the syringe plunger is pushed down, driving the sample solution back through the channel and out through the same end from which it entered. At this point, the sample has passed through the capillary twice, once in each direction. If desired, for example to increase interaction of analyte with extraction surface and to increase the amount of adsorbed analyte, the drawing in and driving out of the sample solution can be one or more time, e.g., four times, which would result in a total of 8 passes of the solution through the channel. This can be accomplished by other means, e.g., through a vacuum or pressure chamber.

In some cases it is desirable to hydrate, solvate and/or otherwise condition the extraction channel prior to use. The particular protocol will depend upon the nature of the extraction chemistry. Capillary conditioning is exemplified in the Examples appended hereto.

In some embodiments of the invention, after the sample solution has been exposed to the extraction surface and analyte adsorbed, the sample solution is substantially eliminated from the channel. For example, after the sample solution has been drawn through the channel one or more times it is substantially drawn or driven out of the capillary and replaced by either gas or liquid. For example, continuing with the illustrative embodiment described above, the syringe pump can be used to pump the sample solution out through the end through which it had entered. While it is not always necessary to remove the sample solution from the capillary prior to elution, it is usually desirable because it reduces the presence of unwanted contaminating species from the sample solution that end up with the eluted protein, and also facilitates control of the desorption solution in the channel. In some embodiments of the invention, residual sample solution can be more thoroughly removed from the channel by blowing air or gas through the channel. However, this is usually not necessary since typically a wash step is performed between the sample loading and elution steps in the purification.

The sample solution can be any solution containing an analyte or analytes of interest. Because sample passes through an open channel, the extraction capillaries of the invention are relatively tolerant of particulate matter in the sample solution compared to packed bed extraction columns. Still, it is often useful to clarify a crude sample prior to introduction into the channel, e.g., by centrifugation or filtration. Examples of sample solutions would include cell lysates, serum-free hybridoma growth medium, tissue or organ extracts, biological fluids, cell-free translation or transcription reactions, or organic synthesis reaction mixtures. In some cases the sample solution is the analyte in a solvent used to dissolve or extract the analyte from a biological or chemical sample. The solvent should be sufficiently weak to ensure sufficient adsorption of the analyte to the channel's extraction surface. Ideally, the adsorption is quantitative, near quantitative, or at least involves a substantial amount of the analyte. Nevertheless, the process can still be very useful where only some smaller fraction of the total analyte is adsorbed, depending upon the nature of the analyte, the amount of starting material, and the purpose for which the analyte is being processed.

In some embodiments of the invention, the channel is washed after the sample loading and prior to analyte elution. Although this step is optional, it is often desirable since it can remove contaminants from the extraction surface and thus improve the purity of the eluted product. In one embodiment, the wash solution is drawn through the capillary using the same or a different syringe pump as was used to draw sample solution through the capillary. A wash solution (i.e., a rinse solution) should be employed that will wash contaminants (e.g., proteins that are not specifically bound to an affinity group) from the extraction surface while, to the extent possible, allowing the adsorbed analyte to remain adsorbed to the extraction surface. The wash solution should also be one that does not damage the analyte molecule or extraction surface. In some cases, such as where the analyte is a protein or protein complex, a wash solution is used that does not denature or degrade the analyte, facilitating recovery of functional native protein.

The exact nature and composition of the wash solution can vary, and will to some extent be determined by the nature of the analyte, the extraction surface, and the nature of the adsorption. Ideally, a wash solution will be able to solubilize and/or wash contaminants from the capillary and extraction surface while leaving the adsorbed analyte bound. In practice, there might need to be some trade-off between the ability to remove all contaminants versus the ability to retain all analyte, which translates into a trade-off between sample purity and sample recovery. That is, a very stringent wash solution capable of effectively removing all contaminants will often also remove some analyte, whereas a wash solution that does not remove any analyte will often not be as effective in removing unwanted contaminants. To some extent, selection of the wash solution will depend upon the relative importance of sample purity vs. sample recovery.

Prior to elution of the adsorbed analyte from an extraction capillary, it is often desirable to purge any residual solution from the capillary, i.e., to blow out the capillary. This residual solution will typically be the wash solution if such is used, or the sample solution if there is not wash step. In some embodiments a purge step can be performed both before the wash step (e.g., to remove residual sample solution) and after the wash step, but purging is normally not necessary prior to the wash step. In certain embodiments, multiple wash steps are employed. For example, in some embodiments an extra $D_2O$ wash is employed prior to elution in a deuterated solvent. Purging can be effected after such extra steps if desired.

While it is often not possible, or even desirable, to remove all trace solution from the capillary and its surface, the objective is to remove enough of the solution so that it is not possible for short segments of solution to form in the capillary during the elution process. Thus, in one embodiment the objective is to substantially remove all bulk liquid from the capillary, without dehydrating or desolvating the extraction surface. The extraction surface and any bound analyte, e.g., a bound protein, remain hydrated and in their native state, while any bulk solution that could detract from the ultimate purity and concentration of the eluted analyte are removed. This can be accomplished by blowing a gas through the capillary for a suitable period of time. The amount of time will vary depending upon the nature of the extraction surface, the nature of the solution in the capillary, etc. An example of a typical purge protocol would involve application of 50-60 psi gas (e.g., nitrogen or helium) to the capillary for several seconds to several minutes. The extraction surface of the capillary will not be dried by the purging, but rather will remain hydrated or solvated, so long as the drying does not go on for too long, or, for example, at too high of a temperature. In other embodiments, the purging is more complete, resulting in partial or even substantial dehydration or desolvation of the extraction surface and/or analyte. Depending upon the nature of the analyte, the extraction surface, and the intended analytical technique, substantial drying is in some cases not a problem, e.g., in some cases where the analyte is a nucleic acid.

Thus, in one embodiment the invention provides an extraction channel (e.g., a capillary) containing a bound analyte that is substantially free of bulk liquid. In particular, the bound analyte can be a biomolecule, such as a biological macromolecule (e.g., a polypeptide, a polynucleotide, or a polysaccharide). The biomolecule can be part of a larger structure, such as a biomolecule complex, an organelle, a virus, a cell or a membrane. In preferred embodiments the analyte is a protein or protein-containing complex. While substantially free of bulk solution, the analyte and/or extraction surface can be fully hydrated. In the case of a biomolecule such as a protein, this hydration can stabilize the binding interaction and the structural and functional integrity of the molecule. An extraction capillary containing a bound, hydrated biomolecule but otherwise substantially free of bulk water can be prepared by purging the capillary for a suitable amount of time. It can be important not to over-dry the capillary, since this could cause the denaturation of a bound biomolecule, and could prevent or hinder recovery of the functional molecule. Under the proper conditions, the capillary and bound analyte will be stable for a substantial period of time, particularly if the proper hydration is maintained. The capillary is useful for providing a pure, concentrated sample of the adsorbed analyte, which can be recovered by using the appropriate elution protocol as described herein. In some embodiments the extraction surface is 3-dimensional.

In another embodiment, the invention provides an extraction channel that is substantially free of liquid and contains a bound biomolecule analyte, and wherein the extraction surface and/or analyte are partially or substantially dehydrated or desolvated. In some embodiments the extraction surface is 3-dimensional and/or the biomolecule is a nucleic acid, or some other molecule that is relatively stable to dehydration.

Finally, after any optional wash and/or purge steps have been performed, the adsorbed analyte is eluted from the capillary via desorption into a desorption solution. The desorption solution can be drawn or driven in and out of the capillary by the same or different mechanism as used for the sample solution and/or wash solution. Thus, in one embodiment a syringe attached to one end of the capillary is used to pull desorption solution through the other end of the capillary and to eject it from the same. The amount of desorption solution used will determine the ultimate concentration of the eluted analyte. While a sufficient amount of desorption solution must be used to achieve satisfactory recovery, it is generally advisable to use as small amount as practical in order to achieve a higher analyte concentration.

The term "liquid segment" is defined herein as a block of liquid in a channel, bounded at each end by a block of liquid or gas. When the liquid segment is substantially immiscible with the liquid or gas on either side of it, it is sometimes referred to as a slug, e.g., a slug of desorption solution. Substantially immiscible implies that constituents of the slug will not mix with any liquid or gas by which it is bound. Where a slug of desorption solution is bounded by gas, for example, the volume and analyte concentration of the slug is well-defined. This is in contrast to the case in many conventional chromatographic approaches, where eluted analyte can diffuse in the elution solvent, leading to, for example, broadening of chromatographic peaks in a chromatogram. Thus, in some embodiments the invention allows for the preparation of a small eluted sample of defined volume and substantially uniform concentration, as determined by the volume of the liquid segment used.

In some embodiments, the amount of desorption solution is greater than the volume of the channel. However, in others, an amount of desorption solution is used that is equal to or less than the volume of the extraction capillary. In the context of open channel solid phase extraction, the term "tube enrichment factor," or "TEF," is defined as the ratio of the volume of an extraction channel to the volume of a liquid segment of desorption solvent used to desorb an analyte from the extraction surface. Desorption of an extracted analyte into a volume of desorption solvent that is less than the volume of the channel, e.g., less than the volume of an extraction capillary, will result in a TEF of greater than one. For example, if analyte is extracted from a sample onto the extraction surface of an extraction capillary having a total volume of 1 µL, and subsequently desorbed into a 0.1 µL slug of desorption solution, the TEF of the extraction is 1 µL/0.1 µL, or 10. In some embodiments of the invention the ability to blow out liquid from an extraction capillary with gas and use a small slug of desorption solvent results in a positive TEF, which can contribute to concentration and enrichment of the analyte. In some embodiments the instant invention provides methods and systems for performing extractions with TEFs greater than one, e.g., TEFs of up to 2, 5, 10, 20, 50, 100, 500, 1000 or greater can be achieved. The resulting sample concentration and/or enrichment can be particularly important with low abundance samples and/or for use with analytical techniques requiring small volumes of sample.

TEF is a component of the total enrichment of the sample. The total enrichment factor of the sample can be increased even further by processing a volume of sample solution that exceeds the volume of the channel. In the context of open channel solid phase extraction, the term "enrichment factor" (or "total enrichment factor") is defined as the ratio of the volume of a sample containing an analyte that is passed through (i.e, loaded onto or processed by) an extraction channel to the volume of liquid segment of desorption solvent used to desorb an analyte from the extraction surface. For example, if a 100 µL, sample containing an analyte is passed through a 1 µL extraction capillary, and the extracted analyte is then eluted with 0.1 µL of desorption solvent, the enrichment factor for the extraction is 100 µL/0.1 µL, or 1000. Thus, the enrichment factor represents a theoretical upper limit for the degree of concentration of the analyte that would be achieved assuming 100% efficiency of analyte adsorption from sample to the extraction surface and of the subsequent desorption into the desorption solvent. The enrichment factor of an extraction can be increased by passing more sample solution through an extraction channel and/or by increasing TEF. The high enrichment factors that can be obtained in many embodiments of this invention are particularly useful when attempting to purify and concentrate a low abundance biomolecule from a relatively large volume of sample solution. In a sense, the ability to concentrate a low abundance protein is analogous to the ability of PCR to amplify a low abundance polynucleotide, and can allow for detection and analysis of proteins than might not otherwise be detectable. Depending upon the volume of sample solution processed and the TEF employed, in certain embodiments of the invention enrichment factors of 10, $10^2$, $10^3$, $10^4$, $10^5$ or higher can be achieved.

In some embodiments of the invention, very small volumes of desorption solvent are employed, e.g., in the range of 0.001 to 500 µL, 0.01 to 500 µL, 0.05 to 500 µL, 0.1 to 500 µL, 1 to 500 µL, 10 to 500 µL, 0.001 to 100 µL, 0.01 to 100 µL, 0.05 to 100 µL, 0.1 to 100 µL, 1 to 100 µL, 10 to 100 µL, 0.001 to 10 µL, 0.01 to 10 µL, 0.05 to 10 µL, 0.1 to 10 µL, 1 to 10 µL, 0.001 to 2 µL, 0.01 to 2 µL, 0.05 to 2 µL, 0.1 to 2 µL, or 0.5 to 2 µL. An advantage of some embodiments of the invention is the ability to collect purified sample in a small, well defined volume of desorption solvent. The desorption solvent can comprise a plug of liquid bounded at one or both ends by gas, or alternatively, by an immiscible liquid.

In another aspect, the invention provides methods of collecting very small fractions of desorbed sample, which might constitute the entire volume of desorption solution used or some fraction thereof. The amount of sample collected can be, e.g., in the range of 0.001 to 500 µL, 0.01 to 500 µL, 0.05 to 500 µL, 0.1 to 500 µL, 1 to 500 µL, 10 to 500 µL, 0.001 to 100 µL, 0.01 to 100 µL, 0.05 to 100 µL, 0.1 to 100 µL, 1 to 100 µL, 10 to 100 µL, 0.001 to 10 µL, 0.01 to 10 µL, 0.05 to 10 µL, 0.1 to 10 µL, 1 to 10 µL, 0.001 to 2 µL, 0.01 to 2 µL, 0.05 to 2 µL, 0.1 to 2 µL, or 0.5 to 2 µL. For example, in some embodiments very small volumes of the desorption solvent are spotted or arrayed on a chip, microwell plate, or other target, as described in more detail elsewhere herein.

While many of the extraction devices of the invention are capable of providing purified analyte in a very small volume of liquid, they are also able (in many cases) to process relatively large original sample volumes, resulting in high enrichment factors. For example, solution volumes of 100 µL to 500 µL, 100 µL to 1 mL, 100 µL to 10 mL, 100 µL to 100 mL, or 100 µL to 1000 mL can be processed in various embodiments of the invention.

It is possible to repeatedly expose the sample, wash and desorption solvent to the extraction surface (e.g., by simply flowing it back and forth through the channel). In the case of sample, this can mean greater extraction efficiencies and hence greater recoveries. In the case of desorption solvent, this can translate into dramatically reduced desorption volume, resulting in a more enriched desorbed sample. Concentrations of the sample can be increased by using only a small slug of desorbing solvent that passes back and forth over the stationary phase before it is deposited from the channel to the target.

The flow rate for the desorption solution should be slow enough that the integrity of the plug is not disturbed. When desorbing the analyte, it can be beneficial to allow the desorption solution to incubate in the capillary (or a section of the capillary when using a small slug of desorption solution) for a period of time, e.g, for one or several minutes.

In general, sensitivity and selectivity can be improved by increasing the number of passes of sample solution and/or desorption solution through the capillary, and/or by decreasing flow rate. Both result in longer exposure of the analyte to the extraction surface. However, both will also result in the extraction process taking longer, so there can be a trade-off of lower throughput for the improved sensitivity and selectivity. Depending upon the relative importance of sensitivity and selectivity vs. throughput, the appropriate number of passages and flow rate can be selected.

While for purposes of illustration much of the foregoing description has focused on the case where solutions enter and leave the capillary through the same opening, other embodiments can also be employed and are encompassed within the scope of the subject invention. For example, in some embodiments one or more of the solutions enter the capillary from one end and exit through the other, as is normally the case with conventional column chromatography.

The sample can be drawn into the channel or pumped through the channel. The sample may be moved back and forth in the channel as many times as is necessary to achieve the desired desorption. Small particulates and air bubbles typically have little or no effect on performance, a remarkable distinction from previous solid phase extraction systems.

The wash solution and desorption solvent also can be introduced from either end and may be moved back and forth in the channel. They can include combination of a capillary channel and a pump for gas and liquids such as conditioning fluid, sample, wash fluid, and desorption fluid. The pump can be, e.g., a syringe (pressure or vacuum), pressure vessel (vial), or centrifugation device. The pumping force is preferably on the bulk fluid and preferably not due to electro osmoticforce; fluid is moved through the capillary channel in a controlled manner. Generally, this means that the volume of liquid acted upon is controlled through positive displacement or movement of a specified volume, timing of the pumping action or through control of the volume of the fluid pumped through the channel. Examples of suitable pumps include syringe or piston, peristaltic, rotary vane, diaphragm, pressurized or vacuum chamber, gravity, centrifugal and centrifugal force, capillary action, piezo-electric, piezo-kinetic and electro-kinetic pumps.

FIGS. 1-4 are schematic drawings of the operation of an open tube extraction channel of this invention. FIG. 1 shows a tubular channel 2, the inner surface of which is coated with a solid phase extraction medium 4. Note that in this drawing the entire inner surface is coated with extraction medium, while in certain embodiments of the invention this might not be the case.

Figure 2:
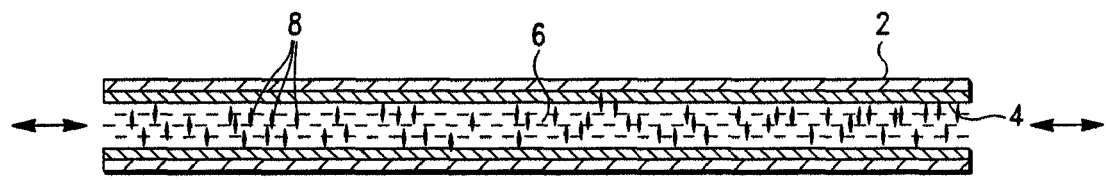

FIG. 2 shows the tubular channel of FIG. 1 as sample 6 is passed through the capillary, and the affinity binding reagent 4 reacts with the sample 6 and adsorbs (i.e., extracts) a protein of interest 8 from the sample. Contaminants that were present in the sample are washed away with an optional wash solution (not shown).

Figure 3:
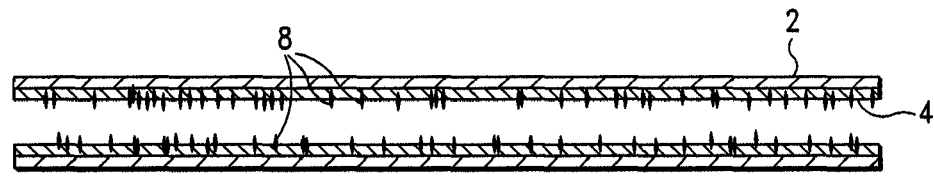

FIG. 3 shows the tubular channel of FIG. 2 after the liquid has been displaced from the channel 2 with a gas such as air, nitrogen or helium.

Figure 4:
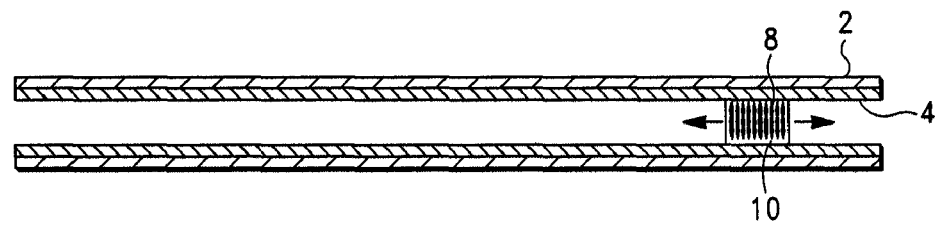

FIG. 4 shows the tubular channel of FIG. 3 as a segment of desorption solvent 10 is passed through the tube 2 to desorb and recover the protein 8. The segment can optionally be passed back and forth through the channel one or more times to improve sample recovery.

As an alternative to the procedure shown in FIG. 4, a desorption fluid can be pumped through the capillary channel in one direction, the front boundary of the fluid desorbing and collecting the protein. The protein desorbs quickly from the wall, and will travel in the front boundary segment of the desorption solvent as the solvent travels down the tube.

The analyte eluted in the solvent segment 10 can be directed and deposited into or onto the target, i.e. a collection vial, a tube, a surface, or an instrument.

After extraction, the residual liquid can be expelled from the tube with a gas such as air to minimize the wash step.

In some embodiments, a series of two or more plugs of desorption solvent separated by air bubbles are employed, i.e., a "sandwich" elution.

Solvents

Extractions of the invention typically involve the loading of analyte in a sample solution, an optional wash with a rinse solution, and elution of the analyte into a desorption solution. The nature of these solutions will now be described in greater detail.

With regard to the sample solution, it typically consists of the analyte dissolved in a solvent in which the analyte is soluble, and in which the analyte will bind to the extraction surface. Preferably, the binding is strong, resulting in the binding of a substantial portion of the analyte, and optimally substantially all of the analyte will be bound under the loading protocol used in the procedure. The solvent should also be gentle, so that the native structure and function of the analyte is retained upon desorption from the extraction surface. Typically, in the case where the analyte is a biomolecule, the solvent is an aqueous solution, typically containing a buffer, salt, and/or surfactants to solubilize and stabilize the biomolecule. Examples of sample solutions include cells lysates, hybridoma growth medium, cell-free translation or transcription reaction mixtures, extracts from tissues, organs, or biological samples, and extracts derived from biological fluids.

It is important that the sample solvent not only solubilize the analyte, but also that it is compatible with binding to the extraction phase. For example, where the extraction phase is based on ion exchange, the ionic strength of the sample solution should be buffered to an appropriate pH such that the charge of the analyte is opposite that of the immobilized ion, and the ionic strength should be relatively low to promote the ionic interaction. In the case of a normal phase extraction, the sample loading solvent should be non-polar, e.g., hexane, toluene, or the like. Depending upon the nature of the sample and extraction process, other constituents might be beneficial, e.g., reducing agents, detergents, stabilizers, denaturants, chelators, metals, etc.

A wash solution, if used, should be selected such that it will remove non-desired contaminants with minimal loss or damage to the bound analyte. The properties of the wash solution are typically intermediate between that of the sample and desorption solutions.

Desorption solvent can be introduced as either a stream or a plug of solvent. If a plug of solvent is used, a buffer plug of solvent can follow the desorption plug so that when the sample is deposited on the target, a buffer is also deposited to give the deposited sample a proper pH. An example of this is desorption from a protein G surface of IgG antibody which has been extracted from a hybridoma solution. In this example, 10 mM phosphoric acid plug at pH 2.5 is used to desorb the IgG from the tube. A 100 mM phosphate buffer plug at pH 7.5 follows the desorption solvent plug to bring the deposited solution to neutral pH. The deposited material can then be analyzed, e.g., by deposition on an SPR chip.

The desorption solvent should be just strong enough to quantitatively desorb the analyte while leaving strongly bound interfering materials behind. The solvents are chosen to be compatible with the analyte and the ultimate detection method. Generally, the solvents used are known conventional solvents. Typical solvents from which a suitable solvent can be selected include methylene chloride, acetonitrile (with or without small amounts of basic or acidic modifiers), methanol (containing larger amount of modifier, e.g. acetic acid or triethylamine, or mixtures of water with either methanol or acetonitrile), ethyl acetate, chloroform, hexane, isopropanol, acetone, alkaline buffer, high ionic strength buffer, acidic buffer, strong acids, strong bases, organic mixtures with acids/bases, acidic or basic methanol, tetrahydrofuran and water. The desorption solvent may be different miscibility than the sorption solvent.

In the case where the extraction involves binding of analyte to a specific cognate ligand molecule, e.g., an immobilized metal, the desorption solvent can contain a molecule that will interfere with such binding, e.g., imidazole or a metal chelator in the case of the immobilized metal.

Examples of suitable phases for solid phase extraction and desorption solvents are shown in Tables A and B.

TABLE A

| Desorption Solvent Features | Normal Phase Extraction | Reverse Phase Extraction | Reverse Phase Ion-Pair Extraction |
|---|---|---|---|
| Typical solvent polarity range | Low to medium | High to medium | High to medium |
| Typical sample loading solvent | Hexane, toluene, $CH_2Cl_2$ | $H_2O$, buffers | $H_2O$, buffers, ion-pairing reagent |
| Typical desorption solvent | Ethyl acetate, acetone, $CH_3CN$ (Acetone, acetonitrile, isopropanol, methanol, water, buffers) | $H_2O/CH_3OH$, $H_2O/CH_3CN$ (Methanol, chloroform, acidic methanol, basic methanol, tetrahydrofuran, acetonitrile, acetone, ethyl acetate,) | $H_2O/CH_3OH$, ion-pairing reagent $H_2O/CH_3CN$, ion-pairing reagent (Methanol, chloroform, acidic methanol, basic methanol, tetrahydrofuran, acetonitrile, acetone, ethyl acetate) |
| Sample elution selectivity | Least polar sample components first | Most polar sample components first | Most polar sample components first |
| Solvent change required to desorb | Increase solvent polarity | Decrease solvent polarity | Decrease solvent polarity |

TABLE B

| Desorption Solvent Features | Ion Exchange Extraction | Hydrophobic Interaction Extraction | Affinity Phase Extraction |
|---|---|---|---|
| Typical solvent polarity range | High | High | High |
| Typical sample loading solvent | $H_2O$, buffers | $H_2O$, high salt | $H_2O$, buffers |
| Typical desorption solvent | Buffers, salt solutions | $H_2O$, low salt | $H_2O$, buffers, pH, competing reagents, heat, solvent polarity |
| Sample elution selectivity | Sample components most weakly ionized first | Sample components most polar first | Non-binding, low-binding, high-binding |
| Solvent change required to desorb | Increase ionic strength or increase retained compounds pH or decrease pH | Decrease ionic strength | Change pH, add competing reagent, change solvent polarity, increase heat |

The Extraction Channel

The subject invention involves the use of solid-phase extraction channels for the extraction of one or more analytes from a sample solution. The term "channel" encompasses but is not limited to the various forms of conventional capillary tubing that are used for applications such as chromatography and capillary electrophoresis, e.g., fused silica capillary tubing. Thus, the term also encompasses other open channels of similar dimensions, having one or more capillary flow passageways, each having an inlet and outlet. Examples include a capillary tube, a bundle of tubes, a solid block or chip having one or more passageways or flow cells running therethrough, e.g., a microfluidics device such as those associated with BiaCore, Inc. (Piscataway, N.J.), Gyros, Inc. (Uppsala, Sweden), Caliper Technologies, Inc. (Mountain View, Calif.) and the like. The passageways can have linear or non-linear central axes, e.g., they can be coiled, curved or straight. The cross-sectional geometry of the passageway is not critical, so long as it allows the channel to function as an extraction channel. For example, capillary tubes having a round cross-sectional geometry work well and can be purchased from a number of vendors. However, other geometries, such as oval, rectangular or another polygonal shape, or a combination of such shapes, can also be employed.

Whatever the geometry of the channel, the dimensions should be such that analyte is able to effectively diffuse and interact with the extraction surface during the course of the extraction process and fluids can be moved through the channel, e.g., pumped through the channel. In general, the larger the molecular weight of an analyte the slower it will diffuse. Thus, with large biological macromolecules it is desirable that the ratio of channel surface area to channel volume per a length of channel is high enough to allow for effective diffusion of analyte to the surface during the time the sample is in the channel. In general, the greater the ratio of the channel perimeter (or circumference, in the case of a round channel) to internal cross-sectional area, the greater the transport or diffusion of analyte from sample solution to extraction surface. In the case of a round channel, this simply means that the smaller the internal diameter of the capillary the more effective the transport will be for a given length of capillary and under given conditions of sample volume, flow rates, residence times, etc. Of course, the trade-off for increased interaction with the capillary extraction surface is lower flow capacity with lower channel perimeter and a lower extraction capacity due to less surface area. In addition, if the perimeter (e.g., circumference) is very small there could be problems with clogging due to any particulate matter or the like that might be present in a sample, such as a crude cell lysate. One of skill in the art would be able to readily select an appropriate capillary having dimensions that allow for effective transport of analyte to the extraction surface while maintaining adequate solution flow and extraction capacity.

As an alternative to increasing ratio of extraction surface area to capillary volume, the transport of bulky analyte to the extraction surface can be improved by lengthening the channel, the flow rate through the channel can be increased, the sample can be passed back and forth through the channel multiple times, the sample can be allowed to incubate in the channel for a period of time, and/or the sample solution can be agitated as it flows through the channel (by introducing tortuosity into the flow path, e.g., by coiling the capillary), by introducing beads or other features into the capillary, etc. Note that a feature such as a bead that is introduced into a capillary to modulate flow properties should not be penetrable to the analyte or introduce unswept dead volumes that would be contrary to the free flow of solvent through the open channel. One measure of flow path tortuosity in the context of coiled capillary tubing is the agitation aspect ratio, described in greater detail in U.S. patent application Ser. No. 10/434,713.

One measure of the effective surface area of a column is the ratio of surface area to volume for a given length of channel, e.g., the ratio of perimeter to cross-sectional area. For example, in the case of a capillary having an inner diameter of 200 μm, the perimeter (in this case the circumference, assuming that the channel is circular) is $\pi \times 200$ μm, or 628 μm. The cross-sectional area is $\pi \times (100$ μm$)^2$, or 31,400 μm$^2$, and the ratio is 0.2 μm$^{-1}$. For a 5 μm i.d. capillary the ratio is 0.8 μm$^{-1}$, for a 50 μm i.d. capillary the ratio is 0.08 μm$^{-1}$, for a 100 μm i.d. capillary the ratio is 0.04 μm$^{-1}$, for a 500 μm i.d. capillary the ratio is 0.0008 μm$^{-1}$, and for a 1000 μm i.d. capillary the ratio is 0.004 μm$^{-1}$. This illustrates the principle that the narrower the channel, the greater is the effective surface area per volume of the channel. In practice, it is likely that the inner surface of a capillary or other channel is not a smooth circle, so the calculated numbers are only theoretical. Of course, the trade-off for the increase in surface area is the reduced capacity of the smaller volume capillary, and sometimes other problems that are introduced by the use of such small channels.

The same sort of calculation can be performed with non-circular channels to derive the ration of perimeter to cross-sectional area, which is generally a measure of the effective surface area of the channel. For example, a square capillary with inner dimensions of 100 μm×10 μm would have a perimeter of 400 μm (4×100 μm) and a cross-sectional area of 10,000 μm$^2$ ((100 μm)$^2$), so the ratio is 400/10,000=0.04 μm$^{-1}$. In some embodiments of the invention, channels having a ratio perimeter to cross-sectional area in the range of, e.g., 0.001 to 2 μm$^{-1}$, 0.002 to 2 μm$^{-1}$, 0.004 to 2 μm$^{-1}$, 0.008 to 2 μm$^{-1}$, 0.04 to 2 μm$^{-1}$, 0.08 to 2 μm$^{-1}$, 0.4 to 2 μm$^{-1}$, 0.8 to 2 μm$^{-1}$, 0.001 to 0.8 μm$^{-1}$, 0.002 to 0.8 μm$^{-1}$, 0.004 to 0.8 μm$^{-1}$, 0.008 to 0.8 μm$^{-1}$, 0.04 to 0.8 μm$^{-1}$, 0.001 to 0.04 μm$^{-1}$, 0.002 to 0.04 μm$^{-1}$, 0.004 to 0.04 μm$^{-1}$, or 0.008 to 0.04 μm$^{-1}$.

The inner walls of the channel can be relatively smooth, rough, textured or patterned. Preferably, they are relatively non-porous. The inner surface can have irregular structure such as is described by Paul Kenis, et al., (2000) Acc. Chem. Res., 33:84 and Paul Kenis, et al., (1999) Science, 285:83. The tube can contain a monolith structure provided that it has channels for liquid passage. Whatever the internal structure of the capillary, it is important to minimize dead volumes or areas that prevent effective removal of solution from the capillary prior to the desorption step in an extraction process.

The capillary channel may be composed of a number of different materials. These include fused silica, polypropylene, polymethylmethacrylate, polystyrene, (nickel) metal capillary tubing, and carbon nanotubes. Polymeric tubes are available as straight tubing or multihole tubing (Paradigm Optics, Inc., Pullman, Wash.). Functional groups may be needed on the capillary tube surface to perform solid phase extraction. Methods to attach chemical groups to polymers are described in the following organic synthesis texts, and these texts are hereby incorporated by reference herein in their entireties, Jerry March ADVANCED ORGANIC CHEMISTRY, 3rd ed., Wiley Interscience: New York (1985); Herbert House, MODERN SYNTHETIC REACTIONS, 2$^{nd}$ ed., Benjamin/Cummings Publishing Co., California (1972); and James Fritz, et al., ION CHROMATOGRAPHY, 3rd, ed., Wiley-VCH, New York (2002); and ORGANIC SYNTHESIS ON SOLID PHASE, F. Dorwald Wiley VCH Verlag Gmbh, Weinheim 2002. Nickel tubing is available from Valco Instrument, Inc., Houston, Tex.

In some embodiments, the extraction channel is a carbon nanotube. Formation of carbon nanotubes has been described in a number of publications including Kenichiro Koga, et al., Nature, 412:802 (2001). Organic functional groups can be attached to the walls of carbon nanotubes and similar polymer composites. See, e.g., Odegard, G. M. et al., "The effect of chemical functionalization on mechanical properties of nanotube/polymer composites," 44$^{th}$ AIAA/ASME/ASCE/AHS Structures, Structural Dynamics and Materials Conference, 7-10 Apr. 2003, Norfolk, Va. and Chen et al. "Chemical attachment of organic functional groups to single-walled carbon nanotube material," (1998) J. Mater. Res. 13(9):2423-13.

In some embodiments, the extraction channel is a fused silica capillary tubing. As used herein the term "fused silica" refers to silicon dioxide (SiO2) in its amorphous (glassy) state, which is a species of the broader genera of compositions commonly referred to as high quality synthetic glass of nearly pure SiO2. The term "synthetic fused silica" refers to amorphous silicon dioxide that has been produced through chemical deposition rather than refinement of natural ore. This synthetic material is of much higher purity and quality as compare to fused quartz made from natural minerals. Examples of fused silica capillaries relevant to this invention include those produced by Polymicro Technologies, LLC of Phoenix, Ariz. and SGE Inc. of Ringwood, Australia. In some cases, it is beneficial to etch a fused silica capillary (e.g., by treatment with base) prior to derivatization with an extraction surface, as described in U.S. patent application Ser. No. 10/434,713.

When using silica capillary, it can be useful to assay the number of silanol groups, e.g., before, during or after derivatization with an extraction surface. Methods of assaying for silanol groups are described in co-pending U.S. patent application entitled "Detection of Silanol Groups on a Surface," Ser. No. 10/733,685, filed Dec. 10, 2003, incorporated by reference herein in its entirety.

The extraction channels of the invention can be of any diameter so long as they are not too large to function as extraction channels, e.g., in the case of a circular capillary, internal diameters in the range of about 2 to 3000 microns, about 2 to 1000 microns, about 10 to 700 microns, about 25 to 400 microns, or about 100 to 200 microns. For non-circular capillaries or channels, corresponding internal perimeter dimensions are desirable.

The volumes of extraction channels can vary depending upon the nature of the analyte, the extraction chemistry, the channel capacity, and the amount of purified analyte required for the particular application. In various embodiments, the volume of the extraction column can be on the order of milliliters, microliters, or nanoliters, e.g., in a range having an upper limit of 1 µL, 10 µL, 100 µL, 1 mL, 10 mL, or 100 mL; and a lower limit of 0.1 nL, 1 nL, 10 nL, 100 nL, 1 µL, 10 µL, 100 µL or 1 mL.

In embodiments of the invention employing capillary tubing, the tubing is beneficially coated with a flexible coating material, typically a polymer or resin. Preferred coating materials include polyimide, silicone, polyacrylate, aluminum or fluoropolymer, especially semiconductor grade polyimide.

Some embodiments of the invention involve the use of a channel having a length of greater than 5 cm, especially in the range of 10 cm to 10 m, 20 cm to 2 m, or 100 cm to 1 m. In other cases the range of capillary lengths is shorter, e.g., having a lower limit of 0.5 cm, 1 cm, 2 cm, 5 cm or 10 cm, and an upper limit of 1 cm, 2 cm, 5 cm, 10 cm, 100 cm, 1 m or 10 m.

In some embodiments of the invention the channel is coiled into a coil comprising multiple turns, e.g., at least 2 turns, at least 5 turns, at least 10 turns, at least 50 turns, at least 100 turns, or even 200 or more turns. In particular, with respect to fused silica capillary tubing the maximum number of turns is in general limited only by the length of capillary used, the design of the device, and the ASR limitations as described herein. Thus in some embodiments the number of coils can reach 1000, 2000, 10,000 or even more. Specific teaching regarding the coiling of capillary tubing is provided in the U.S. patent application entitled "Biomolecule Open Channel Solid Phase Extraction Systems and Methods," Ser. No. 10/733,664, filed Dec. 10, 2003, incorporated by reference herein in its entirety.

Extraction Surfaces

In the subject invention a solid-phase extraction chemistry attached to the inner surface of the capillary is used to extract an analyte of interest from solution. The solid-phase extraction surface can take any of a wide variety of forms. For example, the extraction surface can be selected from, or based on, any of the extraction chemistries used in solid-phase extraction and/or chromatography, e.g., reverse-phase, normal phase, hydrophobic interaction, hydrophilic interaction, ion-exchange or affinity binding. Because the invention is particularly suited to the purification and/or concentration of biomolecules, extraction surfaces capable of adsorbing such molecules are particularly relevant. The extraction surface can be a monolayer, or can take the form of a 3-dimensional extraction matrix, as described in more detail in the U.S. Provisional Application No. 60/523,518, incorporated by reference herein in its entirety.

As used herein the term "affinity binding agent" refers to a molecule or functional group having a specific binding affinity for a molecule or chemical moiety of interest. For example, the affinity group could have a specific affinity for a particular biomolecule or class of biomolecules, or for a specific motif or chemical moiety. Examples would be affinity binding agents (e.g., a ligand) that specifically bind to antibodies or particular classes of antibodies (e.g., Protein A or Protein G) or that specifically bind an affinity tag used to purify recombinant fusion proteins (e.g., a poly-histidine tag). Preferred are affinity binding agents that interact selectively and reversibly with an analyte of interest. The references listed below show different types of affinity binding groups used for solid phase extraction and are hereby incorporated by reference herein in their entireties. Antibody Purification Handbook, Amersham Biosciences, Edition AB, 18-1037-46 (2002); Protein Purification Handbook, Amersham Biosciences, Edition AC, 18-1132-29 (2001); Affinity Chromatography Principles and Methods, Amersham Pharmacia Biotech, Edition AC, 18-1022-29 (2001); The Recombinant Protein Handbook, Amersham Pharmacia Biotech, Edition AB, 18-1142-75 (2002); and Protein Purification: Principles, High Resolution Methods, and Applications, Jan-Christen Janson (Editor), Lars G. Ryden (Editor), Wiley, John & Sons, Incorporated (1989).

There are a wide variety of affinity binding agents suitable for use in embodiments of the subject invention. Many of the groups fall into one of the following interaction categories:

1. Chelating metal—ligand interaction
2. Protein—Protein interaction
3. Organic molecule or moiety—Protein interaction
4. Sugar—Protein interaction
5. Nucleic acid—Protein interaction
6. Nucleic acid—nucleic acid interaction In Table C are listed a number of examples of affinity binding reagents, the corresponding analyte, and the interaction category.

TABLE C

| Examples of Affinity molecule or moiety fixed at surface | Captured biomolecule | Interaction Category |
|---|---|---|
| Ni-NTA | His-tagged protein | 1 |
| Ni-NTA | His-tagged protein within a multi-protein complex | 1, 2 |
| Fe-IDA | Phosphopeptides, phosphoproteins | 1 |
| Fe-IDA | Phosphopeptides or phosphoproteins within a multi-protein complex | 1, 2 |
| Antibody or other Proteins | Protein antigen | 2 |
| Antibody or other Proteins | Small molecule-tagged protein | 3 |
| Antibody or other Proteins | Small molecule-tagged protein within a multi-protein complex | 2, 3 |
| Antibody or other Proteins | Protein antigen within a multi-protein complex | 2 |
| Antibody or other Proteins | Epitope-tagged protein | 2 |
| Antibody or other Proteins | Epitope-tagged protein within a multi-protein complex | 2 |
| Protein A, Protein G or Protein L | Antibody | 2 |
| Protein A, Protein G or Protein L | Antibody | 2 |
| ATP or ATP analogs; 5'-AMP | Kinases, phosphatases (proteins that requires ATP for proper function) | 3 |
| ATP or ATP analogs; 5'-AMP | Kinase, phosphatases within multi-protein complexes | 2, 3 |
| Cibacron 3G | Albumin | 3 |
| Heparin | DNA-binding protein | 4 |
| Heparin | DNA-binding proteins within a multi-protein complex | 2, 4 |
| Lectin | Glycopeptide or glycoprotein | 4 |
| Lectin | Glycopeptide or glycoprotein within a multi-protein complex | 2, 4 |
| ssDNA or dsDNA | DNA-binding protein | 5 |

TABLE C-continued

| Examples of Affinity molecule or moiety fixed at surface | Captured biomolecule | Interaction Category |
|---|---|---|
| ssDNA or dsDNA | DNA-binding protein within a multi-protein complex | 2, 5 |
| ssDNA | Complementary ssDNA | 6 |
| ssDNA | Complementary RNA | 6 |
| Streptavidin/Avidin | Biotinylated peptides (ICAT) | 3 |
| Streptavidin/Avidin | Biotinylated engineered tag fused to a protein (see avidity.com) | 3 |
| Streptavidin/Avidin | Biotinylated protein | 3 |
| Streptavidin/Avidin | Biotinylated protein within a multi-protein complex | 2, 3 |
| Streptavidin/Avidin | Biotinylated engineered tag fused to a protein within a multi-protein complex | 2, 3 |
| Streptavidin/Avidin | Biotinylated nucleic acid | 3 |
| Streptavidin/Avidin | Biotinylated nucleic acid bound to a protein or multi-protein complex | 2, 3 |
| Streptavidin/Avidin | Biotinylated nucleic acid bound to a complementary nucleic acid | 3, 6 |

U.S. patent application Ser. No. 10/434,713 describes in more detail the use of specific affinity binding reagents in capillary solid-phase extraction. Examples of specific affinity binding agents include proteins having an affinity for antibodies, Fc regions and/or Fab regions such as Protein G, Protein A, Protein A/G, and Protein L; chelated metals such as metal-NTA chelate (e.g., Nickel NTA, Copper NTA, Iron NTA, Cobalt NTA, Zinc NTA), metal-IDA chelate (e.g., Nickel IDA, Copper IDA, Iron IDA, Cobalt IDA) and metal-CMA (carboxymethylated aspartate) chelate (e.g., Nickel CMA, Copper CMA, Iron CMA, Cobalt CMA, Zinc CMA); glutathione surfaces-nucleotides, oligonucleotides, polynucleotides and their analogs (e.g., ATP); lectin surface-heparin surface-avidin or streptavidin surface, a peptide or peptide analog (e.g., that binds to a protease or other enzyme that acts upon polypeptides).

In some embodiments of the invention, the affinity binding reagent is one that recognizes one or more of the many affinity groups used as affinity tags in recombinant fusion proteins. Examples of such tags include poly-histidine tags (e.g., the 6×-His tag), which can be extracted using a chelated metal such as Ni-NTA-peptide sequences (such as the FLAG epitope) that are recognized by an immobilized antibody; biotin, which can be extracted using immobilized avidin or streptavidin; "calmodulin binding peptide" (or, CBP), recognized by calmodulin charged with calcium-glutathione S-transferase protein (GST), recognized by immobilized glutathione; maltose binding protein (MBP), recognized by amylose; the cellulose-binding domain tag, recognized by immobilized cellulose; a peptide with specific affinity for S-protein (derived from ribonuclease A); and the peptide sequence tag CCxxCC (where xx is any amino acid, such as RE), which binds to the affinity binding agent bis-arsenical fluorescein (FlAsH dye).

Antibodies can be extracted using, for example, proteins such as protein A, protein G, protein L, hybrids of these, or by other antibodies (e.g., an anti-IgE for purifying IgE).

Chelated metals are not only useful for purifying poly-his tagged proteins, but also other non-tagged proteins that have an intrinsic affinity for the chelated metal, e.g., phosphopeptides and phosphoproteins.

Antibodies can also be useful for purifying non-tagged proteins to which they have an affinity, e.g., by using antibodies with affinity for a specific phosphorylation site or phosphorylated amino acids.

In other embodiments of the invention extraction surfaces are employed that are generally less specific than the affinity binding agents discussed above. These extraction chemistries are still often quite useful. Examples include ion exchange, reversed phase, normal phase, hydrophobic interaction and hydrophilic interaction extraction or chromatography surfaces. In general, these extraction chemistries, methods of their use, appropriate solvents, etc. are well known in the art, and in particular are described in more detail in U.S. patent application Ser. No. 10/434,713 and references cited therein, e.g., Chromatography, $5^{th}$ edition, PART A: FUNDAMENTALS AND TECHNIQUES, editor: E. Heftmann, Elsevier Science Publishing Company, New York, pp A25 (1992); ADVANCED CHROMATOGRAPHIC AND ELECTROMIGRATION METHODS IN BIOSCIENCES, editor: Z. Deyl, Elsevier Science BV, Amsterdam, The Netherlands, pp 528 (1998); CHROMATOGRAPHY TODAY, Colin F. Poole and Salwa K. Poole, and Elsevier Science Publishing Company, New York, pp 394 (1991); and ORGANIC SYNTHESIS ON SOLID PHASE, F. Dorwald Wiley VCH Verlag Gmbh, Weinheim 2002.

Analytical Techniques

Extraction channels and associated methods of the invention find particular utility in preparing samples of analyte for analysis or detection by a variety of analytical techniques. In particular, the methods are useful for purifying an analyte, class of analytes, aggregate of analytes, etc, from a biological sample, e.g., a biomolecule originating in a biological fluid. It is particularly useful for use with techniques that require small volumes of pure, concentrated analyte. In many cases, the results of these forms of analysis are improved by increasing analyte concentration. In some embodiments of the invention the analyte of interest is a protein, and the extraction serves to purify and concentrate the protein prior to analysis. The methods are particular suited for use with label-free detection methods or methods that require functional, native (i.e., non-denatured protein), but are generally useful for any protein or nucleic acid of interest.

These methods are particularly suited for application to proteomic studies, the study of protein-protein interactions, and the like. The elucidation of protein-protein interaction networks, preferably in conjunction with other types of data, allows assignment of cellular functions to novel proteins and derivation of new biological pathways. See, e.g., Curr Protein Pept Sci. 2003 4(3):159-81.

Many of the current detection and analytical methodologies can be applied to very small sample volumes, but often require that the analyte be enriched and purified in order to achieve acceptable results. Conventional sample preparation technologies typically operate on a larger scale, resulting in waste because they produce more volume than is required. This is particularly a problem where the amount of starting sample is limited, as is the case with many biomolecules. These conventional methods are generally not suited for working with the small volumes required for these new methodologies. For example, the use of conventional packed bed chromatography techniques tend to require larger solvent volumes, and are not suited to working with such small sample volumes for a number of reasons, e.g., because of loss of sample in dead volumes, on frits, etc. See U.S. patent application Ser. No. 10/434,713 for a more in-depth discussion of problems associated with previous technologies in connection with the enrichment and purification of low abundance biomolecules.

In certain embodiments, the invention involves the direct analysis of analyte eluted from an extraction channel without any intervening sample processing step, e.g., concentration, desalting or the like, provided the method is designed correctly. Thus, for example, a sample can be eluted from a capillary and directly analyzed by MS, SPR or the like. This is a distinct advantage over other sample preparation methods that require concentration, desalting or other processing steps before analysis. These extra steps can increase the time and complexity of the experiment, and can result in significant sample loss, which poses a major problem when working with low abundance analytes and small volumes.

One example of such an analytical technique is mass spectroscopy (MS). In application of mass spectrometry for the analysis of biomolecules, the molecules are transferred from the liquid or solid phases to gas phase and to vacuum phase. Since many biomolecules are both large and fragile (proteins being a prime example), two of the most effective methods for their transfer to the vacuum phase are matrix-assisted laser desorption ionization (MALDI) or electrospray ionization (ESI). Some aspects of the use of these methods, and sample preparation requirements, are discussed in more detail in U.S. patent application Ser. No. 10/434,713. In general ESI is more sensitive, while MALDI is faster. Significantly, some peptides ionize better in MALDI mode than ESI, and vice versa (Genome Technology, June 220, p 52). The extraction channel methods and devices of the instant invention are particularly suited to preparing samples for MS analysis, especially biomolecule samples such as proteins. An important advantage of the invention is that it allows for the preparation of an enriched sample that can be directly analyzed, without the need for intervening process steps, e.g., concentration or desalting.

ESI is performed by mixing the sample with volatile acid and organic solvent and infusing it through a conductive needle charged with high voltage. The charged droplets that are sprayed (or ejected) from the needle end are directed into the mass spectrometer, and are dried up by heat and vacuum as they fly in. After the drops dry, the remaining charged molecules are directed by electromagnetic lenses into the mass detector and mass analyzed. In one embodiment, the eluted sample is deposited directly from the capillary into an electrospray nozzle, e.g., the capillary functions as the sample loader. In another embodiment, the capillary itself functions as both the extraction device and the electrospray nozzle.

For MALDI, the analyte molecules (e.g., proteins) are deposited on metal targets and co-crystallized with an organic matrix. The samples are dried and inserted into the mass spectrometer, and typically analyzed via time-of-flight (TOF) detection. In one embodiment, the eluted sample is deposited directly from the capillary onto the metal target, e.g., the capillary itself functions as the sample loader. In one embodiment, the extracted analyte is deposited on a MALDI target, a MALDI ionization matrix is added, and the sample is ionized and analyzed, e.g., by TOF detection.

In other embodiments of the invention, channel extraction is used in conjunction with other forms of MS, e.g., other ionization modes. In general, an advantage of these methods is that they allow for the "just-in-time" purification of sample and direct introduction into the ionizing environment. It is important to note that the various ionization and detection modes introduce their own constraints on the nature of the desorption solution used, and it is important that the desorption solution be compatible with both. For example, the sample matrix in many applications must have low ionic strength, or reside within a particular pH range, etc. In ESI, salt in the sample can prevent detection by lowering the ionization or by clogging the nozzle. This problem is addressed by presenting the analyte in low salt and/or by the use of a volatile salt. In the case of MALDI, the analyte should be in a solvent compatible with spotting on the target and with the ionization matrix employed.

In some embodiments, the invention is used to prepare an analyte for use in an analytical method that involves the detection of a binding event on the surface of a solid substrate. These solid substrates are generally referred to herein as "binding detection chips," examples of which include hybridization microarrays and various protein chips. As used herein, the term "protein chip" is defined as a small plate or surface upon which an array of separated, discrete protein samples (or "dots") are to be deposited or have been deposited. In general, a chip bearing an array of discrete ligands (e.g., proteins) is designed to be contacted with a sample having one or more biomolecules which may or may not have the capability of binding to the surface of one or more of the dots, and the occurrence or absence of such binding on each dot is subsequently determined. A reference that describes the general types and functions of protein chips is Gavin MacBeath, Nature Genetics Supplement, 32:526 (2002). See also Ann. Rev. Biochem., 2003 72:783-812.

In general, these methods involve the detection binding between a chip-bound moiety "A" and its cognate binder "B"; i.e, detection of the reaction A+B=AB, where the formation of AB results, either directly or indirectly, in a detectable signal. Note that in this context the term "chip" can refer to any solid substrate upon which A can be immobilized and the binding of B detected, e.g., glass, metal, plastic, ceramic, membrane, etc. In many important applications of chip technology, A and/or B are biomolecules, e.g., DNA in DNA hybridization arrays or protein in protein chips. Also, in many cases the chip comprises an array multiple small, spatially-addressable spots of analyte, allowing for the efficient simultaneous performance of multiple binding experiments on a small scale.

In various embodiments, it can be beneficial to process either A or B, or both, prior to use in a chip experiment, using the extraction capillaries and related methodologies described herein. In general, the accuracy of chip-based methods depends upon specific detection of the AB interaction. However, in practice binding events other than authentic AB binding can have the appearance of an AB binding event, skewing the results of the analysis. For example, the presence of contaminating non-A species that have some affinity for B, contaminating non-B species having an affinity for A, or a combination of these effects, can result in a binding event that can be mistaken for a true AB binding event, or interfere with the detection of a true AB binding event. These false binding events will throw off any measurement, and in some cases can substantially compromise the ability of the system to accurately quantify the true AB binding event.

Thus, in one embodiment, an extraction channel is used to purify a protein for spotting onto a protein chip, with the protein serving as A. In the production of protein chips, it is often desirable to spot the chip with very small volumes of protein, e.g., on the order of 1 µL, 100 nL, 10 nL or even less. Many embodiments of this invention are particularly suited to the efficient production of such small volumes of purified protein. The technology can also be used in a "just-in-time" purification mode, where the chip is spotted just as the protein is being purified.

Examples of protein analytes that can be beneficially processed by the technology described herein include antibodies (e.g., IgG, IgY, etc.); general affinity proteins, (e.g., scFvs, Fabs, affibodies, peptides, etc.); nucleic acids aptamers and photoaptamers as affinity molecules, and other proteins to be screened for undetermined affinity characteristics (e.g., protein libraries from model organisms). The technology is particularly useful when applied to preparation of protein samples for global proteomic analysis, for example in conjunction with the technology of Protometrix Inc. (Branford, Conn.). See, for example, Zhu et al. "Global analysis of protein activities using proteome chips (2001) Science 293 (5537): 2101-05; Zhu et al., "Analysis of yeast protein kinases using protein chips" (2000) Nature Genetics 26:1-7; and Michaud and Snyder "Proteomic approaches for the global analysis of proteins" (2002) BioTechniques 33:1308-16.

A variety of different approaches can be used to affix A to a chip surface, including direct/passive immobilization (can be covalent in cases of native thiols associating with gold surfaces, covalent attachment to functional groups at a chip surface (e.g., self-assembled monolayers with and without additional groups, immobilized hydrogel, etc.), non-covalent/affinity attachment to functional groups/ligands at a chip surface (e.g., Protein A or Protein G for IgGs, phenyl(di) boronic acid with salicylhydroxamic acid groups, streptavidin monolayers with biotinylated native lysines/cysteines, etc.).

In this and related embodiments, a protein is purified and/or concentrated using an extraction channel method as described herein, and then spotted at a predetermined location on the chip. In preferred embodiments, the protein is spotted directly from an extraction capillary onto the substrate. That is, the protein is extracted from a sample solution and then eluted in a desorption solution directly onto the chip. Of course, in this embodiment it is important that the desorption solution be compatible with the substrate and with any chemistry used to immobilize or affix the protein to the substrate. Typically a microarray format involves multiple spots of protein samples (the protein samples can all be the same or they can be different from one another). Multiple protein samples can be spotted sequentially or simultaneously. Simultaneous spotting can be achieved by employing a multiplex format, where an array of extraction capillaries is used to purify and spot multiple protein samples in parallel. The small size and portability made possible by the use of capillaries facilitates the direct spotting of freshly purified samples, and also permits multiplexing formats that would not be possible with bulkier conventional protein extraction devices. Particularly when very small volumes are to be spotted, it is desirable to use a pump capable of the accurate and reproducible dispensing of small volumes of liquid, as described elsewhere herein.

In another embodiment, extraction capillaries of the invention are used to purify B, e.g., a protein, prior to application to a chip. As with A, purified B can be applied directly to the chip, or alternatively, it can be collected from the capillary and then applied to the chip. The desorption solution used should be selected such that it is compatible with the chip, the chemistry involved in the immobilization of A, and with the binding and/or detection reactions. As with A, the methods of the invention allow for "just-in-time" purification of the B molecule.

A variety of extraction chemistries and approaches can be employed in the purification of A or B. For example, if a major contaminant or contaminants are known and sufficiently well-defined (e.g., albumin, fibrin, etc), an extraction chemistry can be employed that specifically removes such contaminants. Alternatively, A or B can be trapped on the extraction surface, contaminants removed by washing, and then the analyte released for use on the binding chip. This further allows for enrichment of the molecule, enhancing the sensitivity of the AB event.

The detection event requires some manner of A interacting with B, so the central player is B (since it isn't part of the protein chip itself). The means of detecting the presence of B are varied and include label-free detection of B interacting with A (e.g., surface plasmon resonance imaging as practiced by HTS Biosystems (Hopkinton, Mass.) or Biacore, Inc. (Piscataway, N.J.), microcantilever detection schemes as practiced by Protiveris, Inc. (Rockville, Md.) microcalorimetry, acoustic wave sensors, atomic force microscopy, quartz crystal microweighing, and optical waveguide lightmode spectroscopy (OWLS), etc). Alternatively, binding can be detected by physical labeling of B interacting with A, followed by spatial imaging of AB pair (e.g., Cy3/Cy5 differential labeling with standard fluorescent imaging as practiced by BD-Clontech (Palo Alto, Calif.), radioactive ATP labeling of kinase substrates with autoradiography imaging as practiced by Jerini AG (Berlin, Germany), etc), or other suitable imaging techniques.

In the case of fluorescent tagging, one can often achieve higher sensitivity with planar waveguide imaging (as practiced by ZeptoSens (Witterswil, Switzerland)). See, for example, Voros et al. (2003) BioWorld 2-16-17; Duveneck et al. (2002) Analytica Chimica Acta 469: 49-61, Pawlak et al. (2002) Proteomics 2:383-93; Ehrat and Kresbach (2001) Chimia 55:35-39—Weinberger et al. (2000) Pharmacogenomics 395-416; Ehrat and Kresbach (2000) Chimia 54:244-46—Duveneck and Abel (1999) Review on Fluorescence-based Planar Waveguide Biosensors, Proc. SPIE, Vol. 3858: 59-71; Budach et al. (1999) Anal. Chem. 71:3347-3355; Duveneck et al. (1996) A Novel Generation of Luminescence-based Biosensors: Single-Mode Planar Waveguide Sensors, Proc. SPIE, 2928:98-109; and Neuschafer et al. (1996) Planar Waveguides as Efficient Transducers for Bioaffinity Sensors, Proc. SPIE, 2836:221-234.

Binding can also be detected by interaction of AB complex with a third B-specific affinity partner C, where C is capable of generating a signal by being fluorescently tagged, or is tagged with a group that allows a chemical reaction to occur at that location (such as generation of a fluorescent moiety, direct generation of light, etc.). Detection of this AB-C binding event can occur via fluorescent imaging, (as practiced, e.g., by Zyomyx, Inc. (Hayward, Calif.) and SomaLogic Inc. (Boulder, Colo.)), chemiluminescence imaging (as practiced by HTS Biosystems and Hypromatrix Inc (Worcester, Mass.)), fluorescent imaging via waveguide technology, or other suitable detection means.

In other embodiments of the invention, similar methodology is used to extract and spot other non-protein analytes in an array format, e.g., polynucleotides, polysaccharides or natural products. Analogous to the protein chip example above, any of these analytes can be directly spotted on a microarray substrate, thus avoiding the necessity to collect purified sample in some sort of vial or microwell prior to transfer to the substrate. Of course, it is also possible to use the extraction methods of the invention to purify and collect such substrates prior to spotting, particularly if the high recovery and activity to be achieved by direct spotting is not required.

In some embodiments, the technology is used to prepare a sample prior to detection by optical biosensor technology, e.g., the BIND biosensor from SRU Biosystems (Woburn, Mass.). Various modes of this type of label-free detection are described in the following references: B. Cunningham, P. Li, B. Lin, J. Pepper, "Colorimetric resonant reflection as a direct biochemical assay technique," Sensors and Actuators B, Volume 81, p. 316-328, Jan. 5, 2002; B. Cunningham, B. Lin, J. Qiu, P. Li, J. Pepper, B. Hugh, "A Plastic Colorimetric Resonant Optical Biosensor for Multiparallel Detection of Label-Free Biochemical Interactions," Sensors & Actuators B, volume 85, number 3, pp 219-226, (November 2002); B. Lin, J. Qiu, J. Gerstemnaier, P. Li, H. Pien, J. Pepper, B. Cunningham, "A Label-Free Optical Technique for Detecting Small Molecule Interactions," Biosensors and Bioelectronics, Vol. 17, No. 9, p. 827-834, September 2002; Cunningham, J. Qiu, P. Li, B. Lin, "Enhancing the Surface Sensitivity of Colorimetric Resonant Optical Biosensors," Sensors and Actuators B, Vol. 87, No. 2, p. 365-370, December 2002, "Improved Proteomics Technologies," Genetic Engineering News, Volume 22, Number 6, pp 74-75, Mar. 15, 2002; and "A New Method for Label-Free Imaging of Biomolecular Interactions," P. Li, B. Lin, J. Gerstemnaier, and B. T. Cunningham, Accepted July, 2003, Sensors and Actuators B.

In some modes of optical biosensor technology, a colorimetric resonant diffractive grating surface is used as a surface binding platform. A guided mode resonant phenomenon is used to produce an optical structure that, when illuminated with white light, is designed to reflect only a single wavelength. When molecules are attached to the surface, the reflected wavelength (color) is shifted due to the change of the optical path of light that is coupled into the grating. By linking receptor molecules to the grating surface, complementary binding molecules can be detected without the use of any kind of fluorescent probe or particle label. High throughput screening of pharmaceutical compound libraries with protein targets, and microarray screening of protein-protein interactions for proteomics are examples of applications that can be amenable to this approach.

In some embodiments, the invention is used to prepare an analyte for detection by acoustic detection technology such as that being commercialized by Akubio Ltd. (Cambridge, UK). Various modes of this type of label-free detection are described in the following references: M. A. Cooper, "Label-free screening of molecular interactions using acoustic detection," Drug Discovery Today 2002, 6 (12) Suppl.; M. A. Cooper "Acoustic detection of pathogens using rupture event scanning (REVS)," Directions in Science, 2002, 1, 1-2; and M. A. Cooper, F. N. Dultsev, A. Minson, C. Abell, P. Ostanin and D. Klenerman, "Direct and sensitive detection of a human virus by rupture event scanning," Nature Biotech., 2001, 19, 833-837.

In some embodiments the invention is used to prepare an analyte for detection by atomic force microscopy, scanning force microscopy and/or nanoarray technology such as that being commercialized by BioForce Nanosciences Inc. (Ames, Iowa). See, for example, Limansky, A., Shlyakhtenko, L. S., Schaus, S., Henderson, E. and Lyubchenko, Y. L. (2002) Amino Modified Probes for Atomic Force Microscopy, Probe Microscopy 2(3-4) 227-234; Kang, S-G., Henderson, E. (2002) Identification of Non-telomeric G-4 binding proteins in human, *E. coli*, yeast and *Arabidopsis*. Molecules and Cells 14(3), 404-410; Clark, M. W., Henderson, E., Henderson, W., Kristmundsdottir, A., Lynch, M., Mosher, C. and Nettikadan, S., (2001) Nanotechnology Tools for Functional Proteomics Analysis, J. Am. Biotech. Lab; Kang, S-G., Lee, E., Schaus, S, and Henderson, E. (2001) Monitoring transfected cells without selection agents by using the dual-cassette expression EGFP vectors. Exp. Molec. Med. 33(3) 174-178; Lu, Q. and E. Henderson (2000) Two Tetrahymena G-DNA binding proteins, TGP I and TGP 3, have novel motifs and may play a role in micromiclear division. Nuc. Acids Res. 28(15); Mosher, C., Lynch, M., Nettikadan, S., Henderson, W., Kristmundsdottir, A., Clark, M. C. and Henderson, E., (2000) NanoAsrays, The Next Generation Molecular Array Format for High Throughput Proteomics, Diagnostics and Drug Discovery JALA, 5(5) 75-78; O'Brien, J. C., Vivian W. Jones, and Marc D. Porter, Curtis L. Mosher and Eric Henderson, (2000) Immunosensing Platforms Using Spontaneously Adsorbed Antibody Fragments on Gold. Analytical Chemistry, 72(4), 703-710; Tseng, H. C., Lu, Q., Henderson, E., and Graves, D. J., (1999) Rescue of phosphorylated Tau-mediated microtubule formation by a natural osinolyte TMAO. Proc Natl Acad Sci USA 1999 Aug. 17; 96(17):9503-8; Lynch, M. and Henderson, E. (1999) A reliable preparation method for imaging DNA by AFM. Microscopy Today, 99-9, 10; Mazzola, L. T., Frank, C. W., Fodor, S. P. A., Lu, Q., Mosher, C., Lartius, R. and Henderson, E. (1999) Discrimination of DNA hybridization using chemical force microscopy. Biophys. J., 76, 2922-2933; Jones, V. W., Kenseth, J. R., Porter, M. D., Mosher, C. L. and Henderson, E. (1998) Microminiaturized immunoassays using Atomic Force Microscopy and compositionally patterned antigen arrays. Analy. Chem., 70 (7), 1233-1241; Fritzsche, W. and Henderson, E. (1997) Ribosome substructure investigated by scanning force microscopy and image processing. J. Micros. 189, 50-56; Fritzsche, W. and Henderson, E. (1997) Mapping elasticity of rehydrated metaphase chromosomes by scanning force microscopy. Ultramicroscopy 69 (1997), 191-200; Schaus, S. S, and Henderson, E. (1997) Cell viability and probe-cell membrane interactions of XR1 glial cells imaged by AFM. Biophysical Journal, 73, 1205-1214—W. Fritzsche, J. Symanzik, K. Sokolov, E. Henderson (1997) Methanol induced lateral diffusion of colloidal silver particles on a silanized glass surface—a scanning force microscopy study. Journal of Colloidal and Interface Science, Journal of Colloid and Interface Science 185 (2), 466-472—Fritzsche, W. and Henderson, E. (1997) Chicken erythrocyte nucleosomes have a defined orientation along the linker DNA—a scanning force microscopy study. Scanning 19, 42-47; W. Fritzsche, E. Henderson (1997) Scanning force microscopy reveals ellipsoid shape of chicken erythrocyte nucleosomes. Scanning 19, 42-47; Vesekna, J., Marsh, T., Miller, R., Henderson, E. (1996) Atomic force microscopy reconstruction of G-wire DNA. J. Vac. Sci. Technol. B 14(2), 1413-1417; W. Fritzsche, L. Martin, D. Dobbs, D. Jondle, R. Miller, J. Vesenka, E. Henderson (1996) Reconstruction of Ribosomal Subunits and rDNA Chromatin Imaged by Scanning Force Microscopy. Journal of Vacuum Science and Technology B 14 (2), 1404-1409—Fritzsche, W. and Henderson, E. (1996) Volume determination of human metaphase chromosomes by scanning force microscopy. Scanning Microscopy 10(1); Fritzsche, W., Sokolov, K., Chumanov, G., Cottom, T. M. and Henderson, E. (1996) Ultrastructural characterization of colloidal metal films for bioanalytical applications by SFM. J. Vac. Sci. Technol., A 14 (3) (1996), 1766-1769; Fritzsche, W., Vesenka, J. and Henderson, E. (1995) Scanning force microscopy of chromatin. Scanning Microscopy. 9(3), 729-739; Vesenka, J., Mosher, C. Schaus, S. Ambrosio, L. and Henderson, E. (1995) Combining optical and atomic force microscopy for life sciences research. BioTechniques, 19, 240-253; Jondle, D. M., Ambrosio, L., Vesenka, J. and Henderson, E. (1995) Imaging and manipulating chromosomes with the atomic force microscope. Chromosome Res. 3 (4), 239-244; Marsh, T. C., J. Vesenka, and E. Henderson. (1995) A new DNA nanostructure imaged by scanning probe microscopy. Nuc. Acids Res., 23(4), 696-700; Martin, L. D., J. P. Vesenka, E. R. Henderson, and D. L. Dobbs. (1995) Visualization of nucleosomal structure in native chromatin by atomic force microscopy. Biochemistry, 34, 4610-4616—Mosher, C., Jondle, D., Ambrosio, L., Vesenka, J. and Henderson, E. (1994) Microdissection and Measurement of Polytene Chromosomes Using the Atomic Force Microscope. Scanning Microscopy, 8(3) 491-497; Vesenka, J., R. Miller, and E. Henderson. (1994) Three-dimensional probe reconstruction for atomic force microscopy. Rev. Sci. Instrum., 65, 1-3—Vesenka, J., Manne, S., Giberson, R., Marsh, T. and Henderson, E. (1993) Colloidal gold particles as an incompressible atomic force microscope imaging standard for assessing the compressibility of biomolecules., Biophys. J., 65, 992-997; Vesenka, J., S. Manne, G. Yang, C. J. Bustamante and E. Henderson. (1993) Humidity effects on atomic force microscopy of gold-labeled DNA on mica. Scan. Mic. 7(3): 781-788; Rubim, J. C., Kim, J-H., Henderson, E. and Cotton, T. M. (1993) Surface enhanced raman scattering and atomic force microscopy of brass electrodes in sulfuric acid solution containing benzotriazole and chloride ion. Applied Spectroscopy 47 (1), 80-84; Parpura, V., Haydon, P. G., Sakaguchi, D. S., Henderson, E. (1993) Atomic force microscopy and manipulation of living glial cells. J. Vac. Sci. Technol. A, I 1 (4), 773-775; Shaiu, W-L., Larson, D. D., Vesenka, J. Henderson, E. (1993) Atomic force microscopy of oriented linear DNA molecules labeled with 5 nm gold spheres. Nuc. Acids Res., 21 (1) 99-103; Henderson, E., Sakaguchi, D. S. (1993) Imaging F-Actin in fixed glial cells with a combined optical fluorescence/atomic force microscope. Neurohnage 1, 145-150; Parpura, V. Haydon, P. G. and Henderson, E. (1993) Three-dimensional imaging of neuronal growth cones and glia with the Atomic Force Microscope. J. Cell Sci. 104, 427-432; Henderson, E., Haydon, P. G and Sakaguchi, D. A. (1992) Actin filaments dynamics in living glial cells imaged by atomic force microscopy. Science, 257, 1944-1946; Henderson, E. (1992) Atomic force microscopy of conventional and unconventional nucleic acid Structures. J. Microscopy, 167, 77-84—Henderson, E. (1992) Nanodissection of supercoiled plasmid DNA by atomic force microscopy. Nucleic Acids Research, 20 (3) 445-447.

In some embodiments the invention is used to prepare an analyte for detection by a technology involving activity-based protein profiling such as that being commercialized by ActivX, Inc. (La Jolla, Calif.). Various modes of this methodology are described in the following references: Kidd et al. (2001) Biochemistry 40:4005-4015; Adam et al. (2000) Chemistry and Biology 57:1-16; Liu et al. (1999) PNAS 96(26):146940-14699; Cravatt and Sorensen (2000) Cum Opin. Chem. Biol. 4:663-668; Patricelli et al. (2001) Proteomics 1-1067-71.

In some embodiments the invention is used to prepare an analyte for analysis by a technology involving a kinetic exclusion assay, such as that being commercialized by Sapidyne Instruments Inc. (Boise, Id.). See, e.g., Glass, T. (1995) Biomedical Products 20(9): 122-23; and Ohumura et al. (2001) Analytical Chemistry 73 (14):3392-99.

The technology used to take up and dispense liquids in the extraction capillaries can be similar to that used for capillary electrophoresis instruments where very small amounts of sample are taken up and dispensed into the capillary. This can also be done in 96 and 384 capillary arrays as are the capillary units used for DNA sequencing. Related techniques are described in Andre Marziali, et al., Annu. Rev. Biomet. Eng., 3:195 (2001). In some cases, the end of the capillary used for solid phase extraction can be the spotter itself. Related techniques are described in MICROARRAY BIOCHIP TECHNOLOGY, Chapter 2—Microfluidic Technologies and Instrumentation for Printing DNA Microarrays, Mark Schena (Editor), Telechem International, Eaton Publishing, ISBN 1-881299-37-6 (2000).

In some embodiments, the systems and methods of the invention are useful for preparing protein samples for crystallization, particularly for use in X-ray crystallography-based protein structure determination. The invention is particularly suited for preparation of samples for use in connection with high throughput protein crystallization methods. These methods typically require small volumes of relatively concentrated and pure protein, e.g., on the order of 1 μL, per crystallization condition tested. Instrumentation and reagents for performing high throughput crystallization are available, for example, from Hampton Research Corp. (Aliso Viejo, Calif.), RoboDesign International Inc. (Carlsbad, Calif.), Genomic Solutions, Inc. (Ann Arbor, Mich.) and Corning Life Sciences (Kennebunk, Me.). Typically, protein crystallization involves mixing the protein with a mother liquor to form a protein drop, and then monitoring the drop to see if suitable crystals form, e.g., the sitting drop or hanging drop methods. Since the determination of appropriate crystallization conditions is still largely empirical, normally a protein is tested for crystallization under a large number of different conditions, e.g., a number of different candidate mother liquors are used. The protein can be purified by channel extraction prior to mixture with mother liquor. The sample can be collected in an intermediate holding vessel, from which it is then transferred to a well and mixed with mother liquor. Alternatively, the protein drop can be dispenses directly from the channel to a well. The invention is particularly suited for use in a high-throughput mode, where drops of protein sample are introduced into a number of wells, e.g., the wells of a multi-well plate (e.g., 94, 384 wells, etc.) such as a CrystalEX 384 plate from Corning (Corning Life Sciences, Kennebunk Me.). The protein drops and/or mother liquors can be dispensed into microwells using a high precision liquid dispensing system such as the Cartesian. Dispensing System Honeybee (Genomic Solutions, Inc., Ann Arbor, Mich.). In high throughput modes it is desirable to automate the process of crystals trial analysis, using for example a high throughput crystal imager such as the RoboMicroscope III (RoboDesign International Inc., Carlsbad, Calif.).

Other analytical techniques particularly suited for use in conjunction with certain embodiments of the invention include surface immobilized assays, immunological assays, various ligand displacement/competition assays, direct genetic tests, biophysical methods, direct force measurements, NMR, electron microscopy (including cryo-EM), microcalorimetry, mass spectroscopy, IR and other methods such as those discussed in the context of binding detection chips, but which can also be used in non-chips contexts.

In one embodiment, an extracted sample is eluted in a deuterated desorption solvent (i.e., $D_2O$, chloroform-d, etc.) for direct analysis by NMR, e.g., an integrated microfluidic-NMR system. For example, a biomolecule analyte is extracted, washed with PBS or a similar reagent, washed with water as needed, and then liquid blown out. The capillary is then washed with $D_2O$, e.g., one or more small slugs of $D_2O$, so as to replace substantially all of the water in the extraction phase matrix with $D_2O$. The analyte is then eluted with a deuterated desorption solution, e.g., a buffer made up in $D_2O$. Deuterated solvents can be obtained, e.g., from Norell, Inc. (Landisville, N.J.).

In general, it is important to use a desorption solvent that is consistent with the requirements of the analytical method to be employed, e.g., in many cases it is preferable that the pH of the desorption solvent be around neutral, such as for use with some protein chips.

Capillary Multiplexing

In some embodiments of the invention, a plurality of channels (e.g., capillaries) are operated in parallel, i.e., in a multiplex fashion. This can be accomplished, for example, by arranging the capillaries in parallel so that fluid can be passed through them concurrently. When a pump is used to manipulate fluids through the column, each capillary in the multiplex array can have its own pump, e.g., syringe pumps activated by a common actuator. Alternatively, capillaries can be connected to a common pump, a common vacuum device, or the like. In another example of a multiplex arrangement, the plurality of capillaries is arranged in a manner such that they can be centrifuged, with fluid being driven through the capillaries by centrifugal force.

In one embodiment, sample can be arrayed from an extraction capillary to a plurality of predetermined locations, for example locations on a chip or microwells in a multi-well plate. A precise liquid processing system can be used to dispense the desired volume of eluant at each location. For example, an extraction capillary containing bound analyte takes up 50 μL of desorption solvent, and 1 μL drops are spotted into microwells using a robotic system such as those commercially available from Zymark (e.g., the SciClone sample handler), Tecan (e.g., the Genesis NPS or Te-MO) or Cartesian Dispensing (e.g., the Honeybee benchtop system). This can be used for high-throughput assays, crystallizations, etc.

Figure 5:
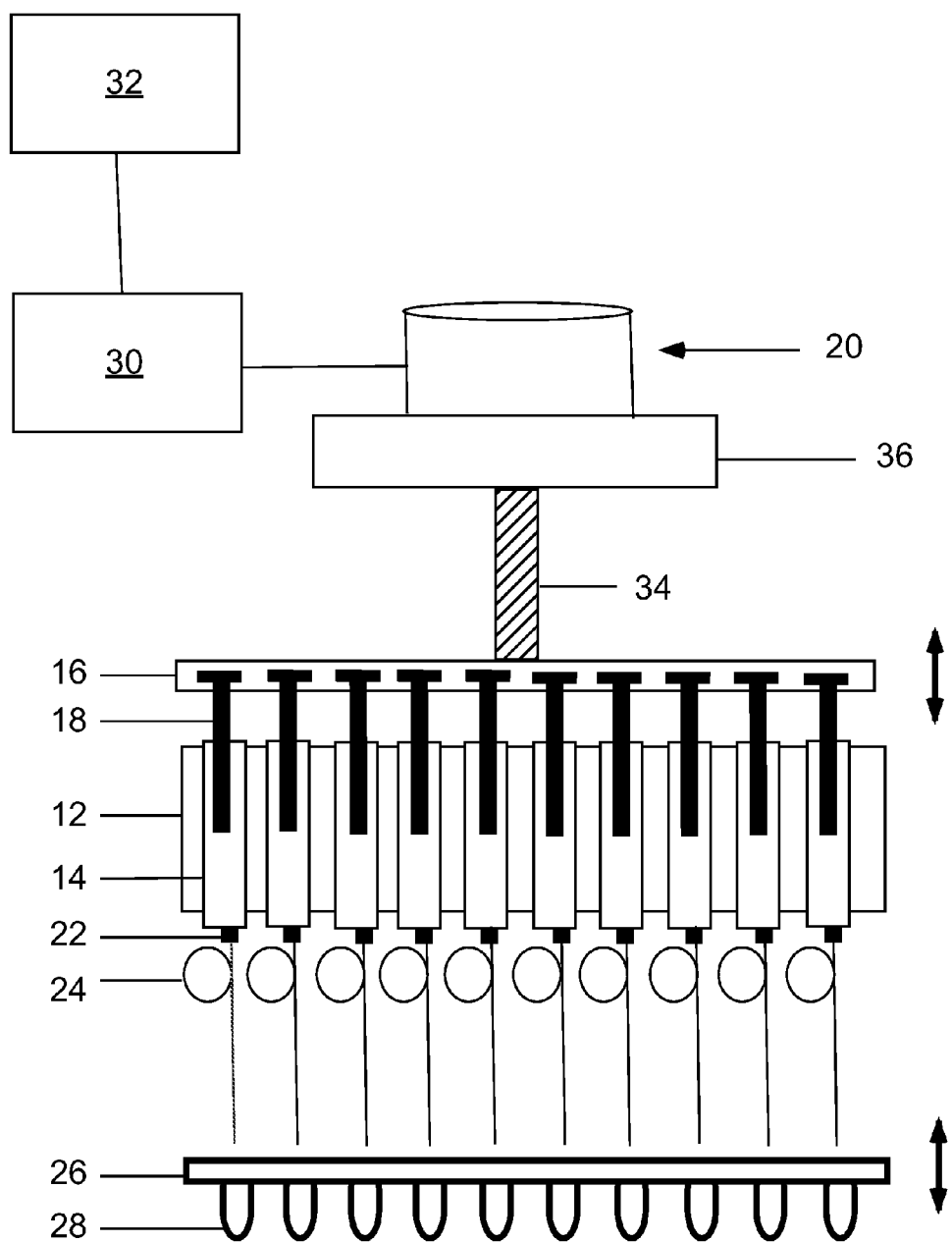
FIG. 5 depicts an example of a multiplexed capillary extraction apparatus.

FIG. 5 depicts an example of a multiplexed capillary extraction system. The system includes a syringe holder 12 for holding a series of syringes 14 and a plunger holder 16 for engaging the plungers 18 with a syringe pump 20. The syringe pump includes a screw 34 to move the plunger holder and a stationary base 36. The syringe pump can move the plunger holder up and down while the syringe holder remains stationary, thus simultaneously actuating all syringe plungers attached to the holder. Each syringe includes an attachment fitting 22 for attachment of an extraction capillary. Attached to each syringe is a coiled fused silica extraction capillary 24. The system also includes a sample rack 26 with multiple positions for holding sample collection vials 28, which can be Eppendorf tubes. The sample rack is slidably mounted on two vertical rods, and the height of the rack can be adjusted by sliding it up or down the rods and locking the rack at the desired location. The position of the rack can be adjusted to bring the input tip of the extraction capillary into contact with solution in a tube in the Eppendorf rack. The system also includes a controller 30 for controlling the syringe pump. The controller is attached to a computer 32, which can be programmed to control the movement of the pump through the controller. The controller allows for control of when and at what rate the plunger rack is moved, which in turn is used to control the flow of solution through the capillaries, withdrawal and infusion. Control of the plungers can be manual or automated, by means of a script file that can be created by a user. The software allows for control of the flow rate through the capillaries, and an extraction protocol can include multiple withdraw and infusion cycles, along with optional delays between cycles.

In one example of a multiplexing procedure, 10 Eppendorf tubes containing a sample, e.g., a clarified cell lysate containing a his-tagged recombinant protein, are placed in the sample rack. One mL syringes are attached to the syringe holder, and the plungers are engaged with the plunger holder. One meter long extraction capillaries, e.g., coiled immobilized-metal extraction capillaries as described elsewhere herein, are affixed to the syringe attachment fittings, e.g., via a Luer fitting. The sample rack is raised so that the ends of the extraction tips enter the sample. Sample solution is drawn into the capillaries by action of the syringe pump, which raises the plunger holder and plungers. The pump is preferably capable of precisely drawing up a desired volume of solution at a desired flow rate, and of pushing and pulling solution through the capillary. An example of a suitable syringe pump is the ME-100 (available from PhyNexus, Inc., San Jose, Calif.). Control of the liquid slug is optionally bidirectional. In this case, and where a syringe is used to control the slug, the syringe plunger head and the syringe body should be tightly held within the syringe pump. When the syringe plunger direction is reversed, then there will be a delay or a hysteresis effect before the syringe can begin to move the slug in the opposite direction. This effect becomes more important as the volume of the slug is decreased. However, because slug movement is bidirectional, the hysteresis effect will also affect how close to the end of capillary that the slug can be moved. In the ME-100 instrument, the syringe and syringe plunger are secured so that no discernable movement can be made against the holder rack.

If the sample volume is larger than the volume of the capillary, sample is drawn through the capillary and into the syringe chamber. The sample solution is then expelled back into the sample container. In some embodiments, the process of drawing sample through the capillary and back out into the sample container is performed two or more times, each of which results in the passage of the sample through the capillary twice. As discussed elsewhere herein, analyte adsorption can in some cases be improved by using a slower flow rate and/or by increasing the number of passages of sample through the capillary.

The sample container is then removed and replaced with a similar container holding wash solution (e.g., in the case of an immobilized metal extraction, 5 mM imidazole in PBS), and the wash solution is pumped back and forth through the capillary (as was the case with the sample). The wash step can be repeated one or more times with additional volumes of wash solution.

Figure 6:
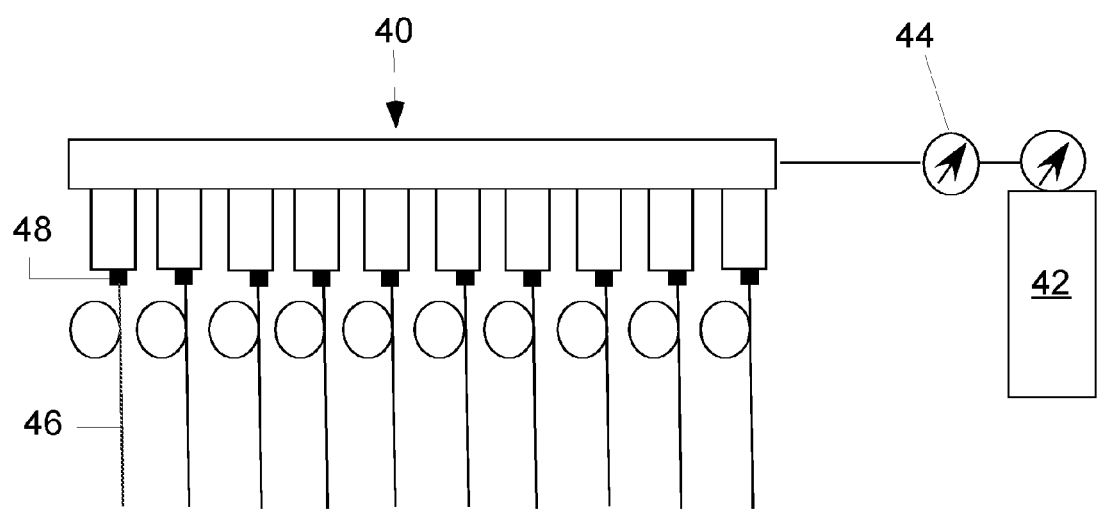
FIG. 6 depicts a gas manifold used in a multiplexed purging operation.

After the wash step, the capillary is typically purged with gas to remove residual solution. In a multiplexed operation such as this, it is useful to use a gas manifold to facilitate the process of purging. An example of such as manifold is shown in FIG. 6. The manifold 40 is attached to a canister 42 holding gas under pressure, along with a valve 44 for controlling release of the gas through the manifold. Capillaries 46 to be purged (in this example ten) are attached to the exit ports 48 of the manifold, and the valve is opened to allow gas to pass through the capillaries in multiplex fashion. A typical purge protocol would involve application of 50 psi gas (either nitrogen or helium) for a total of about 30-60 seconds.

Following the purge, the capillaries are put back onto syringes on the multiplexed extraction apparatus to perform the elution. Optionally, the syringe can be changed prior to elution. For example, 1 mL disposable syringes used for sample and wash solution can be replaced with 50 μL GasTight syringes for the elution. The original sample rack (or a different sample collection tray) is then filled with sample collection vials (e.g., 0.5 mL Eppendorf tubes), and the height of the tubes adjusted so that the capillary openings are just above the bottom of the individual samples tubes. An aliquot of desorption solvent is placed at the bottom of each tube (e.g., 2-15 μL of 200 mM imidazole would be typical for elution of protein off an immobilized metal column). The desorption solution is taken up into the capillary to a point near the attachment to the syringe, e.g., near the Luer fitting. For example, if the volume of desorption solution is 15 μL and the volume of the capillary is about 30 μL, the pump can be programmed to pull up the 15 μL of desorption solution followed by 15 μL of air, e.g., at a flow rate of about 0.03 mL/min. The slow rate should be slow enough to allow the integrity of the fluid segment to be maintained at all times. The eluant can be allowed to incubate in the capillary. For example, the 15 μL of desorption solution can be incubated for 60 seconds at the top half of a 30 μL capillary, then pushed down to the lower 15 μL of the capillary and allowed to incubate there for another 60 seconds. The elution cycle is completed by ejecting the desorption solution back into the sample vial. The elution process can be repeated, in some cases allowing for improved sample recovery.

The above-described extraction process can be automated, for example by using software to program the computer controller to control the pumping, e.g., the volumes, flow rates, delays, and number of cycles.

In some embodiments, the invention provides a multiplexed extraction system comprising a plurality of extraction channels of the invention, e.g., fused silica extraction capillaries. The system can include a pump or pump in operative engagement with the extraction channels, useful for pumping fluid through the capillaries in a multiplex fashion, i.e., concurrently. In some embodiments, each capillary is addressable. The term "addressable" refers to the ability of the fluid manipulation mechanism, e.g., the pumps, to individually address each capillary. An addressable channel is one in which the flow of fluid through the channel can be controlled independently from the flow through any other channel which may be operated in parallel. In practice, this means that the pumping means in at least one of the extraction steps is in contact and control of each individual channel independent of all the other channels. For example, when syringe pumps are used, i.e., pumps capable of manipulating fluid within the capillary by the application of positive or negative pressure, then separate syringes are used at each capillary, as opposed to a single vacuum attached to multiple syringes. Because the capillaries are addressable, a controlled amount of liquid can be accurately manipulated in each capillary. In a non-addressable system, such as where a single pump is applied to multiple capillaries, the liquid handling can be less precise. For example, if the back pressure differs between multiplexed capillaries, then the amount of liquid entering each capillary and/or the flow rate can vary substantially in a non-addressable system. Various embodiments of the invention can also include samples racks, instrumentation for controlling fluid flow, e.g., for pump control, etc. The controller can be manually operated or operated by means of a computer. The computerized control is typically driven by the appropriate software, which can be programmable, e.g., by means of user-defined scripts.

Figure 7G:
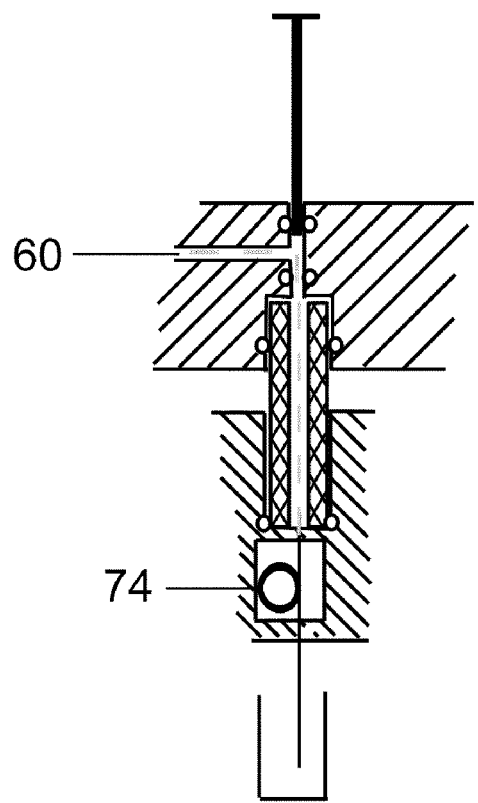
Figure 7H:
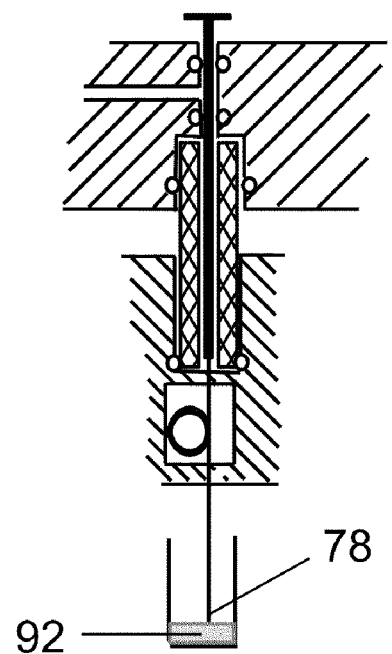
Figure 7I:
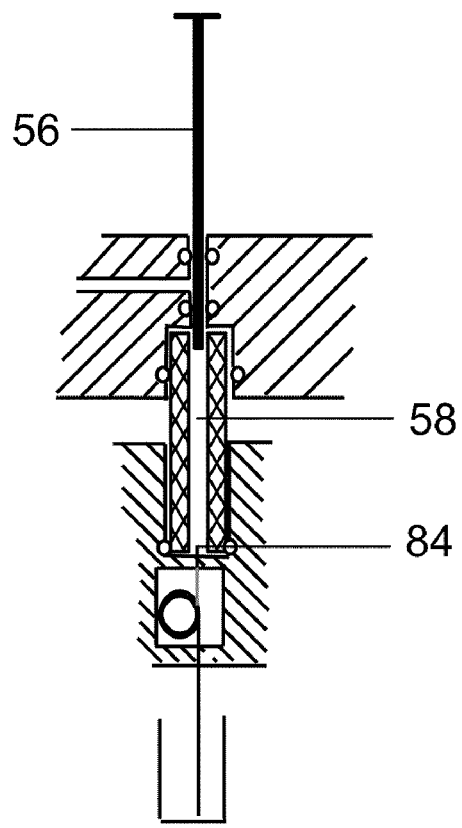
Figure 7J:
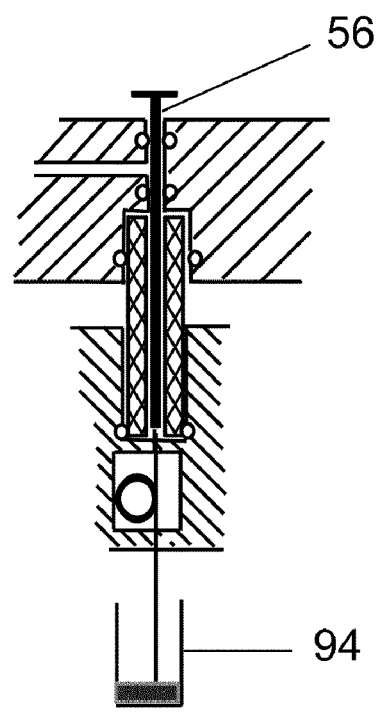

The possible means for fluid manipulation are varied. For example, another embodiment of the invention particularly suited for use in a multiplex context is illustrated in FIGS. 7A-J. The embodiment employs a manifold 52, which includes a plunger-barrel 54, a precision plunger 56 slidably positioned in the manifold so that it can slide through barrel 58, and an inlet port 60 in communication with the barrel 58 (FIG. 7A). In operation, a disposable cartridge 70, comprising a fluid reservoir 72 and a capillary holder 74 is attached to the manifold by sliding the end of the plunger-barrel into the reservoir (FIG. 7B). A seal between the plunger-barrel and the wall of the reservoir is achieved by means of the seal 76. The lower end of the capillary 78 is brought into contact with sample solution 80, contained in sample vial 82, which is positioned in a sample tray. Sample solution is drawn from the sample vial through the capillary and into the reservoir through the upper end of the capillary 84. The sample solution is drawn into and out of the disposable reservoir by lowering the precision plunger 56 to seal the top 50 of the plunger-barrel 54 and pushing and pulling the barrel-plunger 54 like a syringe (FIGS. 7C-7D). The precision plunger 56 is then raised and wash solution is blown through the port 60, the reservoir 72 and out through the capillary 74 (FIG. 7E). The plunger-barrel 54 is then lowered to the bottom of the reservoir (FIG. 7F). Optionally, a second wash (e.g., water) can be blown through the port 60 and through the capillary in down position. Nitrogen is then blown through the port 60 and into the capillary 74 to purge the capillary (FIG. 7G). The lower end of the capillary 78 is inserted into desorption solution 92 (FIG. 7H). The precision plunger 56 is then operated to draw a slug of desorption solution through the capillary until it reaches near the end 84 without entering the barrel (FIG. 7J). The precision plunger 56 is used to control the movement of the plug back and forth in the capillary as described elsewhere herein, and finally the slug of desorption solution containing eluted analyte is collected in a sample vial 94 or deposited on a target (FIG. 7J).

Multiple variations of the above-described embodiments can be readily arrived at and fall within the scope of the claimed invention. For example, the liquid solutions can be introduced into the capillary from either end, e.g., by being pulled up via a plunger or pushed through the capillary from the inlet port. In various embodiments, manipulation of solution in the capillary can be accomplished by means of the precision plunger, the barrel-plunger, or by positive and/or negative pressure applied through the inlet, e.g., by means of a pump, pressurized air, etc. In some embodiments, the plunger is not used in an extraction process; manipulation of fluid is accomplished by means of, e.g., a pump attached at the inlet. The plunger can even be omitted from the manifold in certain embodiments, e.g., where all fluid enters and is controlled via the inlet.

The invention also provides software for implementing the methods of the invention. For example, the software can be programmed to control manipulation of solutions and addressing of capillaries into sample vials, collection vials, for spotting or introduction into some analytical device for further processing.

The invention also includes kits comprising one or more reagents and/or articles for use in a process relating to solid-phase extraction, e.g., buffers, standards, solutions, capillaries, sample containers, etc.

Step and Multi-Dimensional Elutions

In some embodiments of the invention, desorption solvent gradients, step elutions and/or multidimensional elutions are performed.

The use of gradients is well known in the art of chromatography, and is described in detail, for example in a number of the general chromatography references cited herein. As applied to the extraction channels of the invention, the basic principle involves adsorbing an analyte to the extraction surface and then eluting with a desorption solvent gradient. The gradient refers to the changing of at least one characteristic of the solvent, e.g., change in pH, ionic strength, polarity, or the concentration of some agent that influence the strength of the binding interaction. The gradient can be with respect to the concentration of a chemical entity that interferes with or stabilizes an interaction, particularly a specific binding interaction. For example, where the affinity binding agent is an immobilized metal the gradient can be in the concentration of imidazole, EDTA, etc. In some embodiments, the result is fractionation of a sample, useful in contexts such as gel-free shotgun proteomics.

As used herein, the term "dimension" refers to some property of the desorption solvent that is varied, e.g., pH, ionic strength, etc. An elution scheme that involves variation of two or more dimensions, either simultaneously or sequentially, is referred to as a multi-dimensional elution.

Gradients used in the context of the invention can be step. Step elutions are particularly applicable, particularly when segments of desorption solvent bounded by air and/or some other immiscible fluid are employed. In one embodiment, two or more plugs of desorption solvent varying in one or more dimension are employed. For example, the two or more plugs can vary in pH, ionic strength, hydrophobicity, or the like. The segment can have a volume greater than the capillary or less, i.e., a tube enrichment factor of greater than one can be achieved with each plug. Optionally, the capillary can be purged with gas prior to introduction of one or more of the desorption solvent plugs. In one embodiment, the plugs are introduced and ejected from the same end of the capillary. The plug is passed back and forth through the column one or more times. As described elsewhere herein, in some cases the efficiency of desorption is improved by lowering the flow rate of desorption solvent through the capillary and/or by increasing the number of passages, i.e., flowing the solvent back and forth through the capillary.

In another embodiment, a series of two or more plugs of desorption solvent is run through the capillary in sequence, separated by segments of air. In this embodiment, the air-separated segments vary in one or more dimensions. The plugs of solvent can enter and leave the capillary from the same or different ends, or they can enter the capillary at one end and leave from the other. Thus, for example, a series of plugs separated by air can be introduced at one end, and the discrete plugs collected or analyzed directly, for example by introducing each plug into an MS ionization apparatus or onto a protein chip.

In some embodiments of the invention a multidimensional stepwise solid phase extraction is employed. This is particularly useful in the analysis of isotope-coded affinity tagged (ICAT) peptides, as described in U.S. patent application Ser. No. 10/434,713 and references cited therein. A multi-dimensional extraction involves varying at least two desorption condition dimensions.

In a typical example, a stepwise elution is performed in one dimension, collecting fractions for each change in elution conditions. For example, a stepwise increase in ionic strength could be employed where the extraction phase is based on ion exchange. The eluted fractions are then introduced into a second capillary (either directly or after collection into an intermediate holding vessel) and in this case separated in another dimension, e.g., by reverse-phase, or by binding to an affinity binding group such as avidin or immobilized metal.

In some embodiments, one or more dimensions of a multidimensional extraction are achieved by means other than an extraction capillary. For example, the first dimension separation might be accomplished using conventional chromatography, electrophoresis, or the like, and the fractions then loaded on an extraction capillary for separation in another dimension.

Note that in many cases the elution of a protein will not be a simple on-off process. That is, some desorption buffers will result in only partial release of analyte. The composition of the desorption buffer can be optimized for the desired outcome, e.g., complete or near complete elution. Alternatively, when step elution is employed two or more successive steps in the elution might result in incremental elution of fraction of an analyte. These incremental partial elutions can be useful in characterizing the analyte, e.g., in the analysis of a multi-protein complex as described below.

Purification of Classes of Proteins

Extraction capillaries can be used to purify entire classes of proteins on the basis of highly conserved motifs within their structure, whereby an affinity binding agent is used that reversibly binds to the conserved motif. For example, it is possible to immobilize particular nucleotides on the inner capillary surface. These nucleotides include adenosine 5'-triphosphate (ATP), adenosine 5'-diphosphate (ADP), adenosine 5'-monophosphate (AMP), nicotinamide adenine dinucleotide (NAD), or nicotinamide adenine dinucleotide phosphate (NADP). These nucleotides can be used for the purification of enzymes that are dependent upon these nucleotides such as kinases, phosphatases, heat shock proteins and dehydrogenases, to name a few.

There are other affinity groups that can be immobilized on the inner capillary surface for purification of protein classes. Lectins can be immobilized at the inner capillary wall for the purification of glycoproteins. Concanavalin A (Con A) and lentil lectin can be immobilized for the purification of glycoproteins and membrane proteins, and wheat germ lectin can be used for the purification of glycoproteins and cells (especially T-cell lymphocytes). Though it is not a lectin, the small molecule phenylboronic acid can also be immobilized at the inner capillary wall and used for purification of glycoproteins.

It is also possible to immobilize heparin onto the inner surface of the capillary, which is useful for the purification of DNA-binding proteins (e.g. RNA polymerase I, II and III, DNA polymerase, DNA ligase). In addition, immobilized heparin can be used for purification of various coagulation proteins (e.g. antithrombin III, Factor VII, Factor IX, Factor XI, Factor XII and XIIa, thrombin), other plasma proteins (e.g. properdin, BetaIH, Fibronectin, Lipases), lipoproteins (e.g. VLDL, LDL, VLDL apoprotein, HOLP, to name a few), and other proteins (platelet factor 4, hepatitis B surface antigen, hyaluronidase). These types of proteins are often blood and/or plasma borne. Since there are many efforts underway to rapidly profile the levels of these types of proteins by technologies such as protein chips, the performance of these chips will be enhanced by performing an initial purification and enrichment of the targets prior to protein chip analysis.

It is also possible to attach protein interaction domains to the inner surface of the capillary for purification of those proteins that are meant to interact with that domain. One interaction domain that can be immobilized on the inner surface of the capillary is the Src-homology 2 (SH2) domain that binds to specific phophotyrosine-containing peptide motifs within various proteins. The SH2 domain has previously been immobilized on a resin and used as an affinity reagent for performing affinity chromatography/mass spectrometry experiments for investigating in vitro phosphorylation of epidermal growth factor receptor (EGFR) (see Christian Lombardo, et al., Biochemistry, 34:16456 (1995)). Other than the SH2 domain, other protein interaction domains can be immobilized on the inner surface of the capillary for the purposes of purifying those proteins that possess their recognition domains. Many of these protein interaction domains have been described (see Tony Pawson, Protein Interaction Domains, Cell Signaling Technology Catalog, 264-279 (2002)) for additional examples of these protein interaction domains).

As other class-specific affinity ligands, benzamidine can be immobilized on the inner surface of the capillary for purification of serine proteases. The dye ligand Procion Red HE-3B can be immobilized on the inner surface of the capillary for the purification of dehydrogenases, reductases and interferon, to name a few.

In another example, synthetic peptides, peptide analogs and/or peptide derivatives can be used to purify proteins, classes of proteins and other biomolecules that specifically recognize peptides. For example, certain classes of proteases recognize specific sequences, and classes of proteases can be purified based on their recognition of a particular peptide-based affinity binding agent.

Multi-Protein Complexes

In certain embodiments, extraction capillaries of the invention are used to extract and/or process multi-protein complexes. This is accomplished typically by employing a sample solution that is sufficiently non-denaturing that it does not result in disruption of a protein complex or complexes of interest, i.e., the complex is extracted from a biological sample using a sample solution and extraction conditions that stabilize the association between the constituents of the complex. As used herein, the term multi-protein complex refers to a complex of two or more proteins held together by mutually attractive chemical forces, typically non-covalent interactions. Non-covalent attachments would typically be reversible, thus allowing for recovery of component proteins.

In some embodiments, multi-protein complex is adsorbed to the extraction surface and desorbed under conditions such that the integrity of the complex is retained throughout. That is, the product of the extraction is the intact complex, which can then be collected and stored, or directly analyzed (either as a complex or a mixture of proteins), for example by any of the analytical methodologies described herein.

One example involves the use of a recombinant "bait" protein that will form complexes with its natural interaction partners. These multiprotein complexes are then purified through a fusion tag that is attached to the "bait." These tagged "bait" proteins can be purified through groups attached to the surface of the capillary such as metal-chelate groups, antibodies, calmodulin, or any of the other surface groups employed for the purification of recombinant proteins. The identity of the cognate proteins can then be determined by any of a variety of means, such as MS.

It is also possible to purify "native" (i.e. non-recombinant) protein complexes without having to purify through a fusion tag. For example, this can be achieved by using as an affinity binding reagent an antibody for one of the proteins within the multiprotein complex. This process is often referred to as "co-immunoprecipitation." The multiprotein complexes can be eluted, for example, with low pH.

In some embodiments, the multi-protein complex is loaded onto the column as a complex, and the entire complex or one or more constituents are desorbed and eluted. In other embodiments, one or more complex constituents are first adsorbed to the extraction surface, and subsequently one or more other constituents are applied to the extraction surface, such that complex formation occurs on the extraction surface.

In another embodiment, the extraction capillaries of the invention can be used as a tool to analyze the nature of the complex. For example, the protein complex is desorbed to the extraction surface, and the state of the complex is then monitored as a function of solvent variation. A desorption solvent, or series of desorption solvents, can be employed that result in disruption of some or all of the interactions holding the complex together, whereby some subset of the complex is released while the rest remains adsorbed. The identity and state (e.g., post-translational modifications) of the proteins released can be determined often, using, for example, MS. Thus, in this manner constituents and/or sub-complexes of a protein complex can be individually eluted and analyzed. The nature of the desorption solvent can be adjusted to favor or disfavor interactions that hold protein complexes together, e.g., hydrogen bonds, ionic bonds, hydrophobic interactions, van der Waals forces, and covalent interactions, e.g., disulfide bridges. For example, by decreasing the polarity of a desorption solvent hydrophobic interactions will be weakened-inclusion of reducing agent (such as mercaptoethanol or dithiothrietol) will disrupt disulfide bridges. Other solution variations would include alteration of pH, change in ionic strength, and/or the inclusion of a constituent that specifically or non-specifically affects protein-protein interactions, or the interaction of a protein or protein complex with a non-protein biomolecule.

In one embodiment, a series of two or more desorption solvents is used sequentially, and the eluent is monitored to determine which protein constituents come off at a particular solvent. In this way it is possible to assess the strength and nature of interactions in the complex. For example, if a series of desorption solvents of increasing strength is used (e.g., increasing ionic strength, decreasing polarity, changing pH, change in ionic composition, etc.), then the more loosely bound proteins or sub-complexes will elute first, with more tightly bound complexes eluting only as the strength of the desorption solvent is increased.

In some embodiments, at least one of the desorption solutions used contains an agent that effects ionic interactions. The agent can be a molecule that participates in a specific interaction between two or more protein constituents of a multi-protein complex, e.g., Mg-ATP promotes the interaction and mutual binding of certain protein cognates. Other agents that can affect protein interactions are denaturants such as urea, guanidinium chloride, and isothiocyanate, detergents such as triton X-100, chelating groups such as EDTA, etc.

In other sets of experiments, the integrity of a protein complex can be probed through modifications (e.g., post-translational or mutations) in one or more of the proteins. Using the methods described herein the effect of the modification upon the stability or other properties of the complex can be determined.

In some embodiments of the invention, multidimensional solid phase extraction techniques, as described in more detail elsewhere herein, are employed to analyze multiprotein complexes.

Recovery of Native Proteins

In one embodiment, the capillary extraction devices and methods of the invention are used to purify proteins that are functional, active and/or in their native state, i.e., non-denatured. This is accomplished by performing the extraction process under non-denaturing conditions. Non-denaturing conditions encompasses the entire protein extraction process, including the sample solution, the wash solution (if used), the desorption solution, the extraction phase, and the conditions under which the extraction is accomplished. General parameters that influence protein stability are well known in the art, and include temperature (usually lower temperatures are preferred), pH, ionic strength, the use of reducing agents, surfactants, elimination of protease activity, protection from physical shearing or disruption, radiation, etc. The particular conditions most suited for a particular protein, class of proteins, or protein-containing composition vary somewhat from protein to protein.

One particular aspect of the extraction capillary technology of the invention that facilitates non-denaturing extraction is that the process can be accomplished at low temperatures. In particular, because solution flow through the capillary can be done without heating the capillary, e.g., without the introduction of electrical current or the generation of joule heat that typically accompanies capillary processes involving chromatography or electroosmotic flow, the process can be carried out at lower temperatures. Lower temperature could be room temperature, or even lower, e.g., if the process is carried out in a cold room, or the a cooling apparatus is used to cool the capillary. For example, capillary extractions can be performed at a temperature as low as 0° C., 2° C. or 4° C., e.g., in a range such as 0° C. to 30° C., 0° C. to 20° C., 2° C. to 30° C., 2° C. to 20° C., 4° C. to 30° C., or 4° C. to 20° C.

Another aspect of capillary extraction as described herein that allows for purification of native proteins is that the extraction process can be completed quickly, thus permitting rapid separation of a protein from proteases or other denaturing agents present in sample solution. The speed of the process allows for quickly getting the protein from the sample solution to the analytical device for which it is intended, or to storage conditions that promote stability of the protein. In various embodiments of the invention, protein extractions of the invention can be accomplished in less than 1 minute, less than 2 minutes, less than 5 minutes, less than 10 minutes, less than 15 minutes, less than 20 minutes, less than 60 minutes, or less than 120 minutes.

In another aspect, extracted protein is sometimes stabilized by maintaining it in a hydrated form during the extraction process. For example, if a purge step is used to remove bulk liquid (i.e., liquid segments) from the capillary prior to desorption, care is taken to ensure that gas is not blown through the capillary for an excessive amount of time, thus avoiding drying out the capillary and possibly desolvating the extraction phase and/or protein.

In another embodiment, the extraction process is performed under conditions that do not irreversibly denature the protein. Thus, even if the protein is eluted in a denatured state, the protein can be renatured to recover native and/or functional protein. In this embodiment, the protein is adsorbed to the extraction surface under conditions that do not irreversibly denature the protein, and eluting the protein under conditions that do not irreversibly denature the protein. The conditions required to prevent irreversible denaturation are similar to those that are non-denaturing, but in some cases the requirements are not as stringent. For example, the presence of a denaturant such as urea, isothiocyanate or guanidinium chloride can cause irreversible denaturation. The eluted protein is denatured, but native protein can be recovered using techniques known in the art, such as dialysis to remove denaturant. Likewise, certain pH conditions or ionic conditions can result in reversible denaturation, readily reversed by altering the pH or buffer composition of the eluted protein.

The recovery of non-denatured, native, functional and/or active protein is particularly useful as a preparative step for use in processes that require the protein to be denatured in order for the process to be successful. Non-limiting examples of such processes include analytical methods such as binding studies, activity assays, enzyme assays, X-ray crystallography and NMR.

In another embodiment, the invention is used to stabilize RNA. This can be accomplished by separating the RNA from some or substantially all RNase activity, enzymatic or otherwise, that might be present in a sample solution. In one example, the RNA itself is extracted and thereby separated from RNase in the sample. In another example, the RNase activity is extracted from a solution, with stabilized RNA flowing through the capillary. Extraction of RNA can be sequence specific or non-sequence specific. Extraction of RNase activity can be specific for a particular RNase or class of RNAses, or can be general, e.g., extraction of proteins or subset of proteins.

Extraction Tube as Sample Transfer Medium

In certain embodiments, an extraction channel can function not only as a separation device, but also as a means for collecting, transporting, storing and or dispensing a liquid sample.

For example, in one embodiment the extraction capillary is transportable, and can be readily transported from one location to another. Note that this concept of transportability refers to the capillary devices that can be easily transported, either manually or by an automated mechanism (e.g., robotics), during the extraction process. This is to be distinguished from other systems that employ a capillary in a manner such that it is stably connected to a device that is not readily portable, e.g., a gas chromatography or capillary electrophoresis instrument. While one can certainly move such an instrument, for example when installing it in a laboratory, during use the capillary remains stably attached to the stationary instrument. In contrast, in certain embodiments of the invention the capillary is transported.

For example, in one embodiment the extraction capillary is used as a sample collection device, e.g., a sample collection needle. To illustrate, the capillary can be attached to a syringe and used to aspirate a sample. This allows the separation device to be brought directly to the sample, which can be particularly useful when collecting certain biological samples. When using conventional chromatography or electrophoresis in a stationary instrument, the sample must usually be collected and then transferred to the capillary. Direct introduction of sample to the extraction capillary at the site of collection avoids losses that can occur in the process of holding and transporting a sample to a stationary instrument.

For example, in one embodiment an extraction capillary is attached to a pump (by means of a fitting), e.g., a syringe pump or precision pump, and used to collect a sample by aspirating the sample directly into the capillary. This can be particularly useful in situations where the sample volume is limited or where it is difficult to secure sample. Examples include animal studies where the progression of a condition is measured. This includes studies where drug dosage, size and long term effect are measured. Frequently, the entire animal is sacrificed because enough sample in not available or it is difficult to extract the sample to be measured. Another example is tumor biopsies, which can be difficult to reach or limited in size. Still another example is single cell studies, where the cell morphology is measured with respect to the health of the cell.

Many cancers will shed cells at a rate that is higher than the surrounding normal cells, and will shed them into lumens (or "tubes") to which they are in contact. This has been used in the past as a means of collecting cells that have been "enriched" for their cancerous counterparts. For example, a colon cancer cell may possess a relative frequency of one cell in ten thousand within the colon tissue, but are shed into the colon (their lumen) at a rate that is, e.g., 1,000 times higher than their healthy counterparts. Therefore, in this case the cells harvested from the lumen will have a cancer cell:healthy cell frequency of 10:1. There are many lumen types in the body that can potentially "enrich" or sequester cancerous cells for which the lumen's physically small scale require sample collection and processing devices that are of equal/comparable scale. or example, mammary ducts can be the type of small-scale lumen sampled for the purposes of studying and potentially diagnosing breast cancer; lymphatic ducts and lymph nodes can be small-scale lumens for the study of lymphoma and certain leukemias; etc, etc. In these cases, the lumen acts as an in vivo sequestration device, and capillary extraction works to ensure that the sequestration is at minimum maintained, or in certain cases increased or enhanced through further enrichment and/or purification of the studied cells. Once the sample has been taken up by the capillary, it can be processed as described elsewhere herein.

In another embodiment, an extraction capillary is transportable to the site where the eluted sample is destined, e.g., a storage vessel or an analytical instrument. For example, the capillary, with analyte bound, can be transported to an analytical instrument, to a chip, an arrayer, etc, and eluted directly into or onto the intended target. In one embodiment, the capillary is transported to an electrospray ionization chamber and eluted directly therein. In another embodiment, the capillary is transported to a chip or MALDI target and the analyte spotted directly on the target.

In some embodiments of the invention involving transportable capillary or capillary devices, the entire capillary is transported, e.g., on the end of a syringe, or just the bare capillary or a portion thereof. In other cases, one end of the capillary remains attached to a stationary instrument or device and the other end is transportable, e.g., the end can be moved to ionization chamber or to predetermined location for spotting on solid substrate. The relative flexibility of many capillaries permits this type of movement, although it is of course important in many cases to ensure that the capillary is not broken or damaged during transport.

Thus, in various embodiments the invention provides a transportable extraction capillary device, which includes the extraction capillary and optionally other associated components, e.g., pump, holder, etc. The term "transportable" refers to the ability of an operator of the extraction to transport the capillary, either manually or by automated means, during the extraction process, e.g., during sample uptake, washing, or elution, or between any of these steps. This is to be distinguished from non-transportable extraction capillary devices, such as an extraction capillary connected to a stationary instrument, such that the capillary is not transported, nor convenient to transport the capillary, during normal operation of the capillary.

Furthermore, the extraction phase device can serve as both separation medium and transfer tubing. For example, the deposition end of a capillary tube can be positioned to deposit the purified and/or enriched sample directly onto a protein chip, MALDI target or an electrospray nozzle. In this way, the analyte may be transferred without losses.

The system can include means to position the end of capillary channel above, on or in a deposition target. The target may be an injector; protein chip, mass spectrometer, HPLC, or other analytical device or other device for holding or containing sample (such as a vial or tube). The channel can function as both the extraction device and the transport device. The extraction channel can be moved to pick up sample, pick up and discharge wash solvent, and then deposit sample on or in the target. This involves movement of the (nano-scale) extraction device to the sample and detector in contrast to devices which are permanently connected to the detector that move the sample to the device.

In some embodiments, a transportable extraction capillary comprises a fitting for attachment to a pump, such as the pumps described elsewhere herein. In other embodiments, the capillary can be adapted for use as a sample collection needles, for use spotting an eluted sample onto a target substrate, or for operable engagement with an analytical device, such that an eluted sample can be input directly from the extraction channel into the analytical device.

The open channel and a deposition tube to the deposition target can be a continuous channel to facilitate deposition of the desorbed analyte. In this configuration, desorption can be introduced into the open end of the open channel and travel through the open channel to the target; the desorption solvent having a moving front, the initial segment of which desorbs the analyte. Continuing this flow through the deposition tube to the target presents the desorbed analyte in a highly concentrated form to the target. If the target is a chip, the extraction can be performed as part of the arraying process. If the analytical instrument takes samples directly for analysis, the desorbed material can be introduced into the sample inlet of the interface of the instrument.

In some embodiments of the invention, sample is processed in the extraction capillary itself. This can be particularly useful when working with limiting sample material, such as a small biological sample. In one embodiment, a biological sample containing one or more cells is lysed in the extraction capillary itself, thus eliminating transfer steps in a conventional lysis protocol and the associated sample loss. See, e.g., Yeung, E., Internet, "Chemical Characterization of Single Cells and Single Molecules," Trends in Analytical Life Sciences Vol. 1 (CCAB97), published on Internet Sep. 7, 1997 and Chaiyasut, C. et al. "Red Blood Cell Lysis at the Single Cell Level by Using a Mini Electrophoresis Apparatus" (2002) Chromatography 23(1). Lysis can even be accomplished on a single cell in some cases, and the analyte of interest directly extracted without the need for intervening sample processing and transfer steps between collection of the sample and adsorption to the extraction surface. This can allow for collection of sample into an extraction capillary and elution of purified analyte directly into the desired instrument, collection vial, or target, with all sample processing occurring in the capillary itself. Because of the efficiency with which a sample of limited availability can be processed, this methodology can allow for the purification and detection of an analyte that is present at levels that would be undetectable using other technology. This can translate into substantial benefits to the researcher. For example, in some cases the progress of a condition in an experimental animal can be monitored without having to sacrifice the animal, owing to the extremely small samples that can be processed.

Specific cells, classes of cells, viruses and the like can be extracted by using an extraction phase with an affinity for a moiety characteristic to the analyte of interest, e.g., a protein or other biomolecule displayed on the surface of the cell or virus. Many cell types (e.g., cancer cells, types of B cells and T cells, etc.) display characteristic antigenic groups that can be recognized by the corresponding antibody. This antibody can be immobilized to the interior of the extraction channel and function as an affinity group specific for the cell or virus type of interest.

Method for Desalting a Sample

In some embodiments, the invention is used to change the composition of a solution in which an analyte is present. An example is the desalting of a sample, where some or substantially all of the salt (or other constituent) in a sample is removed or replaced by a different salt (or non-salt constituent). The removal of potentially interfering salt from a sample prior to analysis is important in a number of analytical techniques, e.g., mass spectroscopy. These processes will be generally referred to herein as "desalting," with the understanding that the term can encompass any of a wide variety of processes involving alteration of the solvent or solution in which an analyte is present, e.g., buffer exchange or ion replacement.

In some embodiments, desalting is accomplished by extraction of the analyte, removal of salt, and desorption into the desired final solution. For example, the analyte can be adsorbed in a reverse phase, ion pairing or hydrophobic interaction extraction process. In some embodiments, the process will involve use of a hydrophobic interaction extraction phase, e.g., benzyl or a reverse extraction phase, e.g., C8, C18 or polymeric. There are numerous other possibilities; e.g., virtually any type of reverse phase found on a HPLC packing particle can be attached to the wall of fused silica capillary using similar reaction conditions. An example of a C18 capillary fused silica column is a section of CP-Sil 5/C18 fused silica gas chromatography column available from Varian, Inc. Descriptions of an ion-pairing desalting and hydrophobic interactions protocols are provided in the Examples.

An anion exchanger can be used to adsorb an analyte, such as a protein at a pH above its isoelectric point. Desorption can be facilitated by eluting at a pH below the isoelectric point, but this is not required, e.g., elution can be accomplished by displacement using a salt or buffer Likewise, a cation exchanger can be used to adsorb protein at a pH below its isoelectric point, or a similar analyte.

In other embodiments, the desalting process is accomplished using a mixed bed capillary channel. Such processes can be accomplished, for example, using a mixed bed extraction capillary prepared by application of a latex film, or a plurality of latex films, on a capillary surface, as described in the US provisional patent application entitled Three-Dimensional Solid Phase Extraction Surfaces, filed Nov. 18, 2003. A mixed-bed ion exchanger can be used to remove a component or components of a solution. For example mixed bed ion exchanger can be used to exchange the anion, the cation or both from a solution containing a neutral analyte. A description of a mixed bed desalting protocol is provided in the Examples.

In one embodiment, a mixed bed ion exchanger where the anion exchanger is in the hydroxide form and the cation exchanger is in the hydronium form is used to desalt an analyte (e.g., a protein) prior to MS detection.

In Channel Detection of the Extracted Slug

Detection and/or quantification of the amount of extracted analyte is sometimes desired prior to elution of desorbed analyte from the extraction channel. In some embodiments of the invention, the presence and/or concentration of the analyte molecules can be detected in the extraction channel prior elution, e.g., for collection or direction to an analytical instrument. Preferably detection is performed on the enriched and purified biomolecules contained in the desorption solvent slug. It is useful to remove potential interfering material and enrich the material into a slug so that the material can be more readily detected. After the analytes are captured, purified and enriched the molecules are desorbed from the extraction channel with a slug of desorption solvent and the slug is moved to a location in the channel where the analytes can be detected. For example, in some cases it is desirable to determine the concentration or amount of an extracted protein prior to processing with a protein chip. In another example, the amount of an extracted DNA material may be measured prior to performing PCR amplification on the material.

The detection method can be non-destructive, so that the analyte material can be eluted and subjected to further processing and/or detection. Non-destructive detection methods include ultraviolet, visible, fluorescence, chemiluminescence, NMR, IR, and Raman spectroscopy. In cases where the capillary channel is fused silica tubing, a polycarbonate outside coating may be used so that the liquid segment can be detected anywhere that an ultraviolet, visible, or fluorescence detector might be located along the channel. If a polyimide coating is used on the fused silica tubing and the measurement is made perpendicular to the channel, then a window must be burned through the coating and the segment of eluant must be positioned into the window before the measurement can be made. Several capillary channels can be measured at the same time in a multiplexed capillary channel apparatus. This is done by addressing each channel individually through detector transducer and hardware design.

It is important that the measurement is of the desired material and not of other materials that might have been present in the sample solution. Selectivity of the detection method is imparted by the selectivity of the extraction method and/or by selectivity of the measurement method. Affinity extraction methods are inherently selective; therefore, measurement of a material that has been desorbed or eluted from a selective extraction phase is likely to contain substantially only the desired material. Measurement of this material can be done directly. In other cases, where the extraction might be more general or specific to a class of materials, the total extracted material can be measured. If a particular component in the extracted material is measured, then a selective detection method can be used. This can be accomplished by measuring a particular property of the desired material, or a selective reaction reagent can be introduced causing the analyte to give a signal. For example, proteins can be measured through addition of a Bradford reagent.

A solution containing polynucleotides or proteins may be treated with the appropriate ion pairing reagent and passed through a reverse phase capillary channel. The biomolecules will be adsorbed to the capillary channel walls. Other materials in the solution, including salts, will be washed away. Then the biomolecules can be eluted with a slug of an organic solvent e.g. 50% acetonitrile. The slug is directed to the window and a UV detector, such as a Linear Model Spectra 200 UV detector (Therma Analytical, Pleasanton, Calif.) is used to measure the analyte concentration. For DNA or RNA, 260 nm can be used. For proteins, 215 nm can be used. An average absorptivity used to calculate the concentration can be estimated using a standard of known concentration directed to the detection portion of the capillary. Using the segment length, the volume of the slug can be calculated and the mass of the analyte contained in the slug determined.

All publications and patent applications mentioned in this specification are herein incorporated by reference to the same extent as if each individual publication or patent application was specifically and individually indicated to be incorporated by reference.

Having now generally described the invention, the same will be more readily understood through reference to the following examples, which are provided by way of illustration, and are not intended to be limiting of the present invention, unless so specified.

EXAMPLES

The following preparations and examples are given to enable those skilled in the art to more clearly understand and practice the present invention. They should not be construed as limiting the scope of the invention, but merely as being illustrative and representative thereof.

Example 1

Hydroxide Etch-Conditioning of Fused Silica Capillary Tubing

Fused silica capillaries (204 um ID, 362 um OD; 50 meters ×2; obtained from Polymicro Inc. (Phoenix, Ariz., lot

PBWO4A) were etched by treatment of the channel surface with 100 mM NaOH for 50 minutes. The capillaries were then washed with water (6.0 mL), 0.1N HCl (2 mL), water (10 mL) and acetonitrile (6 mL), after which they were dried with nitrogen gas.

Example 2

Synthesis of Amino-Functionalized Capillary

A 10 meter section of the etched capillary described in Example 1 was filled with a solution of $(MeO)_3Si(CH_2)_3NH_2$ (400 uL) in toluene (1200 uL). The capillary was placed in a 120° C. oil-bath and the reaction continued for 16 h with the flow of the silanization solution through the capillary adjusted to 0.8 uL/min. The capillary was then washed with toluene (1000 uL), acetonitrile (2000 uL), and dried with nitrogen.

Example 3

Synthesis of Carboxylic Acid-Functionalized Capillary

A four meter length of the amino-functionalized capillary described in Example 2 was filled with a solution of succinic anhydride (125 mg; 1.25 mmol), DMAP (20 mg), pyridine (25 uL) in DMF (400 uL) and acetonitrile (900 uL). The capillary was placed in a 65 C oven and the reaction continued for 15 h with the flow of the succinic anhydride solution adjusted to 0.6 uL/min. The capillary was then washed with acetonitrile (2000 uL).

Example 4

Synthesis of "Nitrilotriacetic Acid" (NTA)

N,N-Bis-(carboxymethyl) lysine (commonly referred to as "Nitrilotriacetic acid," or "NTA") was synthesized as follows based the procedure reported by Hochuli et al. (Journal of Chromatography, 411:177-184 (1987)).

A solution of H-Lys(Z)—OH (42 g; 150 mmol) in 2N NaOH (225 mL) was added drop wise to a solution of bromoacetic acid (42 g; 300 mmol; 2 eq) in 2N NaOH (150 mL) at ~0 to 10° C. White precipitate formed as the solution of H-Lys(Z)—OH added. The reaction continued at room temperature (RT) overnight, after which the temperature was increased to 60° C. and the reaction continued for another 2 h. 1N HCl (450 mL) was added and the mixture was place in a refrigerator for a couple hours. The solid product (Z-protected NTA) was filtered off and recrystallized by re-dissolving the solid in 1N NaOH, then neutralized with the same amount of 1N HCl. The Z-protected NTA was collected by filtration and dried.

Z-protected NTA was dissolved in 1N NaOH (130 mL) and 5% Pd/C (~450 mg) was added. The reaction mixture was evacuated and saturated with $H_2$ before being stirred at RT under $H_2$ balloon overnight. The reaction mixture was filtered through a celite bed to remove the Pd/C. The filtrate, containing NTA was collected and water (80 mL) was used to wash the filtering bed. 6N HCl was added to bring the pH down to 7.5-8.0. The collected NTA solution was diluted with water to have the final concentration of ~200 mM.

Example 5

Synthesis of an Extraction Capillary Coated with a NTA Monolayer

A four meter length of the carboxyl-functionalized capillary described in Example 3 was activated by filling the capillary with a solution of N-hydroxysuccinimide (115 mg; 1.0 mmol), and EDAC (191.7 mg; 1.0 mmol) in acetonitrile (1500 uL). The reaction continued for 3 h at RT with the flow of the above solution through the capillary adjusted to 5 uL/min. (The reaction can also be carried out for about 14 h with the flow of the reagents solution adjusted to 0.6 uL/min.)

The activated capillary was washed with acetonitrile (1000 uL), then treated with a solution of NTA (described in Example 4) in water (200 mM; pH~8; 1.0 mL). The reaction continued for 14 h at RT with the flow rate adjusted to ~1 uL/min. The capillary was further reacted with 0.5% ethanolamine in water for 2 min before it was washed with water (4 mL).

Example 6

Charging a NTA Extraction Capillary with $Ni^{2+}$

An extraction capillary coated with NTA monolayer as described in Example 5 was washed by flowing 500 uL of 100 mM $NaHCO_3$ through the capillary at a fast flow rate. The washed capillary was then charged with 10 mM $NiSO_4$ for 20 min (flow rate~0.02 mL/min). The charged capillary was then washed with water (1 mL at a fast flow rate), followed by 10 mM NaCl (500 uL; 0.05 mL/min), and then a final water wash (6 mL; 0.1 mL/min). Toward the end of the final water wash the effluent spot checked with PAR reagent (pyridineazoresorcinol) for the presence of any $Ni^{2+}$ (see Example 18).

The capillary was then cut into 1 meter lengths each for use in extraction procedures.

Capillaries that have been used in extractions can be re-charged using the same procedure. Prior to re-charging a capillary it should be washed with 50 mM $Na_2EDTA$ (500 uL; fast with about 1 min of incubation).

Example 7

Synthesis of Poly-Methylcarboxydextran

Dextran (ICN Cat#101507; MW. 15000-20000; 3 g; 55.5 mmol of —OH) was dissolved in 60 mL of water (with the help of a heat gun] and bromoacetic acid (9.3 g; 67 mmol; 1.2 eq) was added [now the pH is really acidic] followed by $Ag_2O$ (8.6 g; 37 mmol; 1.3 eq in term of Ag+). The reaction continued at RT for 24 h. The $Ag_2O$ was not completely dissolved, so the reaction looked like it contained charcoal. This charcoal color eventually turned to milky-brown. The reaction stopped and solid material was filtered over celite. The filtrate was dialyzed then lyophilized to dried powder.

Example 8

Synthesis via Active Ester-Dextran of an Extraction Capillary Coated with a Three-Dimensional NTA Extraction Surface To a solution of poly-methylcarboxydextran (100 mg (dialyzed and freeze-dried, see Example 7); 1.8 mmol of —COOH) in water (3.0 mL) was added N-hydroxysuccinimide (170 mg; 1.5 mmol) followed by EDAC (290 mg; 1.5 mmol). The reaction continued at RT for 3 h. Afterwards there was still quite a bit of grayish precipitate present, which was removed by filtration using a fritted pipette tip.

The resulting active ester-dextran solution was adjusted to pH ~8 with 1M NaOH before being pumped through the aminosilane-derivatized capillaries of Example 2 at a flow rate of 1 uL/min for 14 h (before pumping the dextran solution through the capillaries, they were quickly washed with 100 mM $NaHCO_3$ solution).

The dextran treated-capillaries were washed with water (0.5 mL; flow rate 0.10 mL/min) before a solution of NTA in water (200 mM; pH~8.0; 0.5 mL, as described in Example 4) was pumped through the capillaries. The reaction continued for 4 h at RT with the flow rate adjusted to 0.20 mL/h. The capillaries were washed with water (2 mL) before one meter of capillary was removed and charged with $Ni^{2+}$ as described in Example 6 (single activation).

The remaining capillary was quickly washed with slightly acidic water before being treated with a solution of N-hydroxysuccinimide (170 mg; 1.5 mmol) and EDAC (290 mg; 1.5 mmol) in water (1.5 mL) for 6 h with a flow rate of 0.15 mL/h. The capillary was washed with water (0.5 mL; flow rate 0.10 mL/min), then a solution of NTA in water (200 mM; pH~8.0; 0.5 mL) was introduced into the capillary. The reaction continued for 14 h at RT with the flow rate adjusted 1 uL/min. The capillary was then washed with water (4 mL). The washed capillary was charged with 10 mM $NiSO_4$ for 20 min as described in Example 6 (double activation).

The effect of single activation vs. double activation on binding capacity was evaluated using the methods of Examples 13 and 18. One meter of the single activated.

Example 9

Synthesis of $HSCH_2CO$-NTA

To a solution of thioglycolic acid (460 mg; 5.0 mmol) in acetonitrile (14 mL) was added N-hydroxysuccinimide (600 mg; 5.2 mmol) followed with DCC (1.1 mg; 5.5 mmol). The reaction continued for 30 min at RT (it was noted that a substantial amount of ppt formed after a couple minutes of reaction). The insoluble by-product DCU was filtered off and washed with additional acetonitrile (4 mL). The combined colorless product solution was added to a solution of NTA (see Example 4; 175 mM; pH~8.2; 30 mL; 5.25 mmol; this solution was purged with nitrogen for about 10 min prior to the reaction) and the pH of the reaction mixture adjusted to 8.65 with 1N NaOH. The reaction continued for 3 h at RT under nitrogen. The pH of the reaction mixture was readjusted to 2.5 with 6N HCl before being filtered through a fritted pipette tip. The total volume is 50 mL and assuming 100% yield, the concentration of this solution is 100 mM.

Example 10

Synthesis of Thiol-Functionalized Capillary

Etched capillaries were prepared as described in Example 1 and were filled with a solution of $(MeO)_3Si(CH_2)_3SH$ (20% in toluene) before being placed in an oven at ~125° C. The reaction continued for 16 h with the flow of the silanization solution through the capillary adjusted to 0.15 mL/h. The capillaries were washed with toluene (3000 uL), acetonitrile (2000 uL), water (4 mL), acetonitrile (3000 uL), and dried with nitrogen.

Example 11

Vinylsulfonedextran Synthesis

Dextran (Fluka, St. Louis, Mo. #31387; MW. 15000-20000; 2 g; 37 mmol of —OH) was dissolved in water (60 mL) and phosphate buffer (pH 11.5; 400 mM $Na_2HPO_4$/NaOH; 20 mL) before $NaBH_4$ (40 mg) was added, followed by divinylsulfone (5.5 mL; 74 mmol; 1.5 eq.; added all at once). The reaction continued at RT for 27 minutes, then quenched by adjusting the pH to 6 with 6N HCl. The light yellow reaction mixture was dialyzed and lyophilized.

Example 12

Synthesis via VinylSulfone Dextran of an Extraction Capillary Coated with a Three-Dimensional NTA Extraction Surface Vinylsulfone-dextran (Example 11; 200 mg (dialyzed and freeze-dried)) was dissolved in a solution of 50 mM phosphate buffer (pH=8.5; 3 mL) and DMF (3 mL) was added to clarified the solution. Thiol-functionalized capillaries (Example 10; ~50 meters×2) were filled with the solution using 450 psi (it took ~25 min) and the reaction was allowed to proceed for 1 h at a flow rate through the capillary of 0.5 mL/h.

The dextran-treated capillaries were washed with water (2.5 mL each) before reacting with a solution of $HSCH_2CO$-NTA (Example 9; 100 mM; readjusted to pH 8.5; 3.0 mL per capillary). The reaction continued for 1 h at RT with a flow rate of 0.4 mL/h. The capillaries were then washed with water (2.5 mL each) and charged with 25 mM $NiSO_4$ for 20 minutes before a solution of 5 mM $NiSO_4$ in 10% MeOH—$H_2O$ was used to displace the 25 mM $NiSO_4$ solution (Example 6). The capillaries are stored at 4° C. filled with 5 mM $NiSO_4$ in 10% MeOH—$H_2O$ solution.

Example 13

Procedure for Determining the Capacity of an $Ni^{2+}$-NTA Extraction Capillary via His-GST Protein A $Ni^{2+}$-NTA capillary of interest is dried with $N_2$, then loaded with a 20 uL sample plug of a 2500 ug/mL stock solution of His-GST protein (described in U.S. patent application Ser. No. 10/434,713). The sample plug is moved through the capillary two complete cycles with about 2-5 min of incubation before being expelled from the capillary. The capillary is then washed with water (500 uL; fast flow rate), followed by PBS (10 mM phosphate pH7+140 mM NaCl; 500 uL with about 1 min of incubation) and water (500 uL; fast flow rate). The capillary is then dried (air or $N_2$) for about 2-5 min.

Next the protein is eluted off the capillary with 200 mM imidazole (15 uL). The imidazole plug is moved through the capillary two complete cycles with about 2-5 min of incubation before being expelled from the capillary and collected. 15 uL of water is then added to the collected sample.

The amount of protein in the sample is determined by running sample on an HP1050 HPLC system using a gradient of 25-75% B in 5 min. (solvent A: 0.1% TFA in water and solvent B: 0.1% TFA in acetonitrile) with the detection wavelength of 214 nm, and integrating the protein absorbance peak. A calibration standard is used, which is made by adding 15 uL of a 125 ug/mL protein solution with 15 uL of 200 mM imidazole.

Example 14

Comparison of Capacities of 3-D and Monolayer Extraction Capillaries

The capacity of a monolayer extraction capillary as described in Example 5 was determined using the method of Example 13. A one meter long section of the capillary was found to bind 1.4 μg of His-GST.

A number of 3-D extraction capillaries as described in Example 5 (of the same length) were tested in the same manner, and were found to typically bind about 10-15 μg of protein. Thus, the 3-D extraction surface results in a substantial improvement in protein binding capacity.

Example 15

Vinylsulfone Dextran Assay

The purpose of this assay is to determine the amount of vinylsulfone groups in vinylsulfone dextran that are available for further reaction with any thio-nucleophile.

This assay is based on the on the reaction between excess sodium thiosulphate and the available vinyl groups of vinylsulfone dextran. The reaction produces hydroxide ions which can be titrated with hydrochloric acid to determine the level of vinylsulfone substitution of a given amount of vinylsulfone dextran (Journal of Chromatography (1975) 103:49-62).
Experimental Procedure:
1. Accurately weight out about 100 mg of vinylsulfone dextran.
2. In a 50 mL centrifuge tube, dissolve the vinylsulfone dextran in DMSO (1 mL) and dilute it with water (39 mL). The pH of this solution is acidic.
3. Add sodium thiosulphate (800 mg) and shake well.
4. Allow the reaction to proceed for additional 18 h on a shaker.
5. Pour the reaction mixture into a 200 mL beaker equipped with a stir bar.
6. Turn on and calibrate the pH meter before placing the probe in the beaker that contains the reaction mixture. The set up is then placed on the stirrer with medium setting.
7. Start titrating with 0.01N hydrochloric acid, with the help of a burette, until the pH of the solution reaches 5.60. Record the total volume of HCl used.

Example 16

Evaluation of Vinylsulfone Dextran Samples for Concentration of Vinylsulfone Groups and for Protein Binding Capacity A number of different samples of vinylsulfone dextran were prepared using the method described in Example 11 and assayed using the procedure described in Example 15. The vinylsulfone dextran samples were also used to synthesize 3-D extraction capillaries as described in Example 12 and assayed for His-GST binding capacity using the method of Example 13. The following table provides the mass yield for the vinylsulfonation reactions, the results of vinylsulfone dextran assay for each sample, and the GST capacity for the capillaries corresponding to each sample.

| Sample Name | Yield in g (all with 2.0 g of starting Dextran) | μmol of VS/g of VSD | μg of GST/m of Cap. |
| --- | --- | --- | --- |
| VSD042303 | 4.4 | 550 | ~18 |
| VSD071503 | 2.4 | 534 | 2.4 |
| VSD071603 | 2.7 | 619 | 2.9 |
| VSD072903A | 3.6 | 995 | ~11 |
| VSD072903B | 3.9 | 1068 | ~11 |
| VSD072903C | 3.7 | 990 | ~10 |
| VSD082803A[1] | 2.9 | 495 | 2.7 |
| VSD082803B[1] | 3.0 | 481 | 1.7 |

[1]The starting dextran MW. is 6000 instead of 15000-20000 like the rest of the samples.

With the exception of VSD042303, the VS titration results had a direct correlation to the final protein capacity. However, the data were collected over a period of three to four months and there were some variations. These reaction variables include: the integrity of the GST protein as it was shown to degrade over time, the integrity of the Thio-NTA reagent, the amount of available thio groups on the capillaries, and the experimental variables such as MW of the starting dextran and reaction time.

Example 17

Determination of Binding Specificity for His-GST in a 3-D Extraction Surface Capillary 20 uL of His-GST protein (~1000 ug/mL) was diluted with a solution of 2 mg BSA and 5 mM imidazole in 1 mL of PBS. 500 uL of this mixture was passed through a capillary (3-4 cycles), then washed and eluted with imidazole as described in Example 13. About 7 ug of GST protein was recovered without any detectable BSA.

Example 18

Determination of the Amount of $Ni^{2+}$ Ions Bound to Capillary Surface Via 4-(2-Pyridylazo) Resorcinol (PAR) Reagent The objective of this assay is to determine the amount of $Ni^{2+}$ ions bound to capillary surface by chelation to the NTA moieties. $Ni^{2+}$ ions (in aqueous solution) form a stable, colored complex (2:1) with 4-(2-pyridylazo) resorcinol ("PAR"), with $A_{max}$=495 nm.

The assay is performed on an extraction capillary that has been loaded with $Ni^{2+}$ as described above. A 20 μl slug of 0.01 M HCl is passed through the capillary four times, dissolving the Ni-NTA complex. This effluent is then collected and combined with 20 μl of PAR reagent ($4.0 \times 10^{-4}$ M PAR in 3M $NH_3$, pH=11-12) and incubated for 10 minutes. The sample is analyzed at 495 nm on a FIA flow injection system. Quantification is done via a "one-point" calibration, using $1.0 \times 10^{-4}$ M $NiSO_4$ in 0.25M HCl as the standard solution.

Example 19

Determination of Relationship Between $Ni^{2+}$ Capacity and Protein Capacity The relationship between $Ni^{2+}$ capacity and protein capacity was determined for several different capillaries (see Table), using the procedures of Examples 13 and 18.

Capillary 042203Ni is a Ni-NTA monolayer capillary that was prepared as described in Examples 5 and 6. Capillaries D042303Ni and D042403Ni were prepared using the double activation method of Example 8. Capillary D041003Ni was made by the same procedure as D042303Ni, but the methylcarboxydextran was used before dialysis and lyophilization. Capillary D042503Ni was produced by the same procedure as D042303Ni, with the exception that the solvent in the reactivation reaction of the attached methylcarboxydextran was done in acetonitrile instead of water.

As can be seen from the table, there is a good correlation between nickel chelation and protein binding.

| Capillary ID No. | Ng Chelated Nickel (per M) | Ug His-GST Trapped (per M) |
|---|---|---|
| 042203Ni | 33 | 1.4 |
| D042503Ni | 106 | 5.8 |
| D041003Ni | 137 | 6.3 |
| D042303Ni | 266 | 21 |
| D042403Ni | 320 | 22 |

Example 20

Preparation of a Strong Acid Cation Exchanger Capillary Channel

A 100 µm ID 50 cm fused silica capillary (Polymicro, Inc.) is attached to a syringe pump containing an aqueous 0.1% (v/v) suspension of Biocryl BPA 1000 strong anion exchanger latex (Rohm and Haas, Inc.) and latex is pumped through the capillary at the rate of 100 µL/min for 10 minutes. Then the capillary is flushed with deionized water for 10 minutes, removing the residual anion exchanger. A 0.1% (v/v) aqueous suspension of strong acid cation exchanger, SPR-H Sarasep, Inc. is pumped through the capillary at the rate of 100 µL/min for 10 minutes. The capillary is flushed with deionized water for 10 minutes and then put into a refrigerator for storage.

Example 21

Preparation of a Strong Acid Cation Exchanger Capillary Channel

The process as described in Example 20 is repeated except Biocryl 1050, Rohm and Haas, Inc. is used in place of Biocryl 1000. Biocryl 1050 latex contains both strong base and weak base anion exchanger sites.

Example 22

Preparation of a Strong Acid Cation Exchanger Capillary Channel

The process as described in Example 20 is repeated except Polybrene® (1,5-dimethyl-1,5-diazaundecamethylene polymethobromide, hexadimethrine bromide) Part. Number. 10,768-9/Sigma Aldrich, Inc. is used in place of Biocryl 1000 Polybrene® is a linear strong base anion exchanger polymer.

Example 23

Preparation of a Weak Acid Cation Exchanger

The processes as described in Examples 20, 21, and 22 are repeated except a 0.5% (w/v) aqueous suspension of weak acid cation exchanger latex (TWS-3420, Rohm and Haas, Inc.) is used in place of SPR-H.

Example 24

Synthesis of NTA-Dextran via an Active Ester

To a solution of polymethylcarboxydextran (150 mg, dialyzed and free-dried; 0.93 mmol of sugar, see Example 7) in water (5.0 mL) is added N-hydroxysuccinimide (173 mg; 1.5 mmol) followed by EDAC (380 mg; 2.0 mmol). The reaction continues at RT for 60 min before a solution of NTA (see Example 4) in water (175 mM; pH~8.2; 7.5 mL; 1.2 mmol) is added. The pH of the reaction is then adjusted to ~9 with 0.1N NaOH and the reaction continues for 3 h at RT. The pH of the reaction mixture is adjusted back to ~7, and the whole thing is dialyzed and lyophilized.

Example 25

Synthesis of NTA-Dextran via Vinylsulfone

Vinylsulfone-dextran (150 mg, dialyzed and freeze-dried, see Example 11) is dissolved in 50 mM phosphate buffer (pH=8.5; 5 mL) and DMF (400 uL). $HSCH_2CO$-NTA (100 mM; 5 mL, see Example 9) is added to the vinylsulfone dextran solution. The pH of the resulting solution is adjusted to ~8.5 with 1N NaOH. The reaction continues for 1 h at RT before the pH readjusted to ~6 with 1N HCl and the whole reaction mixture is dialyzed and lyophilized.

Example 26

Preparation of a NTA Chelator

The processes as described in Examples 23 are repeated except the polymer suspension prepared according to Example 24 or 25 is used in place of SPR-H. A 1% (w/v) aqueous suspension of the polymer is pumped through the coated capillary at a rate of 100 mL/min for 10 min and then washed with DI water for 10 min. The capillary is charged with 10 mM $NiSO_4$ for 10 min and then washed with DI water for 10 min.

Example 27

Extracting Multi-Protein DNA-Binding Complexes with Mass Spectrometric Identification of the Complex Composition A 150 µm ID 75 cm length capillary is etched according to Examples 1. The capillary is then filled with a 65° C. 4% (v/v) solution of 3-aminopropyltriethoxysilane in methanol and reacted for 12 hours at a slow flow of 1 µL. After flushing with 100% methanol and then deionized water, the tube is filled with a 5.0 mg/mL NHS-LC biotin (N-hydroxysuccinimidobiotin, Sigma-Aldrich, Milwaukee, Wis., PN H1759) in 50 mM sodium bicarbonate solution pH 8.3 and reacted for 4 hours at room temperature. Following biotinylation the capillary is flushed with deionized water and then the capillary is filled with 4.0 mg/ml solution of streptavidin (Sigma-Aldrich, Milwaukee, Wis., PN S0677) in 50 mM sodium phosphate buffer (pH 7.3). The streptavidin solution is reacted for 4 hours at 40° C. and any remaining free streptavidin is removed by rinsing the capillary tube with deionized water.

DNA sequences being screened for their interactions with multi-protein complexes are prepared. In all cases the target sequence is biotinylated at its 5' end. An example of multi protein complexes are described in Eckhard Nordhoff, et al., Nature Biotech., 17:884 (1999). Short single-stranded biotinylated DNA (<50 bp) is prepared by standard DNA synthesis techniques (i.e. oligonucleotide synthesis). Long single-stranded biotinylated DNA (>50 bp) is prepared by standard PCR techniques, whereby one or both of the PCR primers is 5'-labeled with biotin. The primers are removed after the PCR reaction by standard purification techniques, including DNA Chromatography (Douglas Gjerde, et al., DNA Chromatography, Chapter 6, Wiley-VCH, Weinheim, Germany (2002)). The purified PCR product is then heated to >95° C. and then cooled immediately to 4° C. to produce single-stranded biotinylated DNA. Long double-stranded biotinylated DNA (>50 bp) is prepared in the manner identical to the single-stranded variety, except for elimination of the final heat denaturation and cooling step.

Once the biotinylated DNA of interest is suitably prepared, it is allowed to incubate with the proteins being screened for their DNA interactions. The proteins will most often be derived from whole-cell extracts, nuclear extracts, or any other source of DNA-binding proteins that have been prepared by standard means. Biotinylated DNA (100 ng) is added to the extract and is allowed to incubate in the manner described previously for extraction of DNA-binding proteins (Eckhard Nordhoff, et al., Nature Biotech., 17:884 (1999)). Once the incubation is complete, the unbound biotinylated DNA is removed from the sample by its selective precipitation with polyethyleneimine (PEI), in the manner described previously for the precipitation and removal of DNA (Jesper Svejstrup, et al., Proc. Natl. Acad. Sci. USA, 94:6075 (1997)). Once the unbound DNA is removed, the entire sample that contains the protein-bound biotinylated DNA is introduced into the streptavidin capillary described above. The entire sample is fully drawn up into and pushed out of the capillary at a flow rate of 50 µL/min, and this action is repeated 5 times. Once completed, the capillary is washed by separately drawing up and pushing out to waste 15 µL of water at 100 µL/min, and this action is repeated 5 times. The capillary is then evacuated by flowing 10 psi of air through the capillary for 30 seconds. A single 1 µL segment (approximately 5.6 cm in length) of 50% methanol/50% water is then fully drawn into the capillary, and passing this elution slug over the entire streptavidin surface a total of 5 times at 20 µL/min. The entire 1 µL elution volume that contains the eluted proteins bound to the original DNA sequence is then pushed into an electrospray nozzle (Advion NanoMateTMI 00, Advion Bio-Sciences, Inc., Ithaca, N.Y.; Nanospray needle holder, PN NSI-01 and NSI-02, Nanospray needles, PN NSI-NDL-01 and NSI-NDL-02, LC Packings Inc., San Francisco, Calif.), which is in turn analyzed by ESI-MS/MS (examples of such electrospray nozzles, and their use with MS and MS/MS are described at Xian Huang, et al., Proceedings of the 50th ASMS Conference on Mass Spectrometry and Allied Topics, Orlando, Fla., Jun. 2-6, 2002. The ESI-MS/MS is then used for identification of the proteins that comprise the DNA-binding complex, in a manner described previously (Martin Yarmush, et al., Annu. Rev. Bionied. Eng., 4:349 (2002)).

Example 28

Ion Pairing Desalting

A section of C18 capillary fused silica column (a section of CP-Sil 5/C18 fused silica gas chromatography column available from Varian, Inc (Palo Alto, Calif.)) is used for the extraction channel. An ion pairing reagent is added to the sample and the mixture is introduced to the capillary channel. For example, where the analyte is DNA or RNA 200 mM triethylammonium acetate, pH 7.0 (TEAA) can be used as the ion pairing agent. A two-fold dilution of sample is performed so that the final concentration of the ion pairing reagent is 100 mM. Other types of substituted ammonium reagents may also be used depending on constraints of the detection or amplification technology that is to be used down stream of the desalting process. 200 mM of trifluoroacetic acid (TFA) is used for protein. Hexafluorobutyric acid (HFBA) and other ion pairing reagents can also be used.

After the sample is loaded onto the capillary channel, the capillary is washed with a wash solution including the ion pairing reagent, thereby removing substantially all matrix materials and salts. Then a small volume of organic solvent is used to strip the protein from the capillary and deposit it, e.g., into a target vial or analytical instrument. For example, in many cases a 50/50 (v/v) mixture of ACN water is used. Other organic solvents such as 2-propanol, methanol, ethanol, etc. may be also be used. The most suitable elution solvent for a particular application can be determined based on the nature of the analyte, the extraction phase, the analytical process, etc.

Preconcentration of the sample is also performed with the process if the desorption volume is less than the original sample volume.

Sample loading flow rates should be slow enough to allow complete transport of the desired analyte to the capillary wall. If the sample volume is less than the tube volume, the sample is simply loaded into the capillary and then sufficient time is allow before ejection of the solution from the capillary into the sample vial or analytical device.

Solution containing desalted sample can be directed to a vial, a mass spectrometer with an electrospray nozzle, GC, HPLC or other analytical device.

Example 29

Desalting a Sample Using a Mixed Bed Extraction Capillary

A capillary channel used for desalting is prepared by coating ion exchange polymers on the interior surface of a capillary. In this example, the polymer is a cross-linked latex attached through electrostatic attraction to the silanol groups on the fused silica wall.

The process of making the capillary is started with strong base anion exchanger latex in the hydroxide form. The latex is free of residual ions. It is pumped through the capillary with a 0.1% (v/v) suspension. Latex can be pumped with a piston pump, syringe pump, pressurized vessel, etc. An example of a strong base anion exchanger is Biocryl BPA 1000 formerly available from Rohm and Haas, Inc.

A weak base anion exchanger or a combination of weak and strong base anions exchanger may also be added or coated to the fused silica tubing. An example of a mixed anion exchanger suspension is Biocryl BPA 1050, formerly available from Rohm and Haas, Inc.

The latex or polymer is substantially free of residual ions. The hydroxide anion associated with the anion exchanger is present only as the ion pair associated with the quaternary amine bonded to the latex. There is substantially no "free" hydroxide anion. Cleaning the latex suspension is done by, e.g., centrifugation, decanting, ultrafiltration, cross-flow filtration and/or dialysis.

Another latex layer of the opposite charge may be added or coated on top of the first layer. For example, a strong acid cation exchanger in the hydronium form may be added to the top of the anion exchanger latex bed (an example is SPR-H, formerly available from Sarasep, Inc). This is done with the same method of pumping the latex through the tube. Care is taken so that residual latex of the opposite charge is not present (except that coated to the wall). If residual counter charge latex is present, the latex will precipitate and cannot be coated. Weak acid cation exchanger latex (TWS-3420, formerly available from Rohm and Haas, Inc.) may also be coated. The coating of weak acid latex may be done on either a primary coating of strong base anion exchanger, weak base anion exchanger or a combination of strong base and weak base anion exchanger.

Each layer of latex will be able to deionize (take up) a salt of the appropriate charge. For example, an anion exchanger in the —OH form will be able to take up chloride anion from solution. A cation exchanger in —H form will be able to take up sodium. Combining the two ion exchangers results in a mixed bed. The mixed bed will be able to remove sodium chloride from solution. Since the product of hydroxide and hydronium is water, which is not easily dissociated, the deionization reaction is driven to completion provided there is sufficient ion exchange capacity and the ions that are being removed are able to travel to and react with the appropriate ion exchange site.

As many successive layers may be added as desired to increase capacity of the capillary, e.g., as many as 100 layers each (or more) may be added. It is preferred to add 5 layers each, and most preferred is to add 1 or 2 layers each. Each latex suspension is substantially free of residual ions. Assuming a 10 cm length of 200 µm id fused silica tubing (having a surface area of 0.6 cm$^2$), a latex particle diameter of 100 µm, and that the particles take up about 50% of the total volume, it is predicted that each layer of ion exchanger latex takes up about 0.003 cm$^3$. Assuming a bead density of 1 and an ion exchange capacity of 2 mequiv/g, the ion exchange equivalents is 0.006 mequiv. for every layer. Therefore, a 10 cm length tube of this capacity will be expected to desalt 30 µL volume of 200 mM salt assuming each ion exchange site takes up 1 ion.

The particle size of the latex can range from about 5 nm to about 1000 nm. The preferred size range is 25 to 500, with most preferred 50 to 100 nm.

The predominant surface charge corresponds to the type of ion exchanger last added. A cation exchanger will have a predominant negative surface charge. An anion exchanger will have a predominant positive surface charge. Choice of final surface charge will depend on if there is a charged analyte that is being recovered. If the analyte being recovered is a cation, then the final charge is made cationic. If the charge of the analyte is negative, then the final charge is made anionic. A neutral substance can be recovered from either final charge.

Sample loading flow rates are slow enough to allow complete transport of the desired material to the wall. If the sample volume is less than the tube volume, the sample is simply loaded into the capillary and then sufficient time is allow before ejection of the solution from the capillary into a sample vial or analytical device.

A small sample volume is taken up into a mixed bed extraction capillary, e.g., by means of a syringe attached to the capillary. The volume of liquid to be desalted can be less or more than the volume of the capillary. The volume will be dictated by how much matrix ions must be removed. Samples with lower concentrations of salts can be introduced at higher volumes and vice versa, samples with high salt concentrations can be introduced at lower volumes. The sample is drawn back and forth in the capillary until substantially all matrix salts are taken up by the mixed bed. Substances to be recovered can be neutral or ionic. If they are ionic, the surface charge is same as the substance charge and the substance is too large to move past the surface to interact with the polymer layer below. The procedure works best with neutral substances. Solution containing desalted sample can be directed to a vial, a mass spectrometer with an electrospray nozzle, GC, HPLC or other analytical device.

Example 30

Recovery of Functional His-Tagged GST

Samples of his-tagged GST in an *E. coli* lysate were prepared at concentrations of 0, 2, 10 and 20 ug/mL. 0.5 mL aliquots were purified using a Ni-NTA extraction capillary. The purified samples were then detected on a bare gold grating SPR protein biochip using rabbit anti-GST antibody. The results, shown in the following table and reported in terms of resonance change units (RCU), indicates that the tagged GST is recognized by the antibody.

| GST-his concentration in lysate (ug/mL) | RCU |
| --- | --- |
| 0 | 0 |
| 2 | 13 |
| 10 | 25 |
| 20 | 35 |

Example 31

Recovery of Active DNA Polymerase

Figure 8:
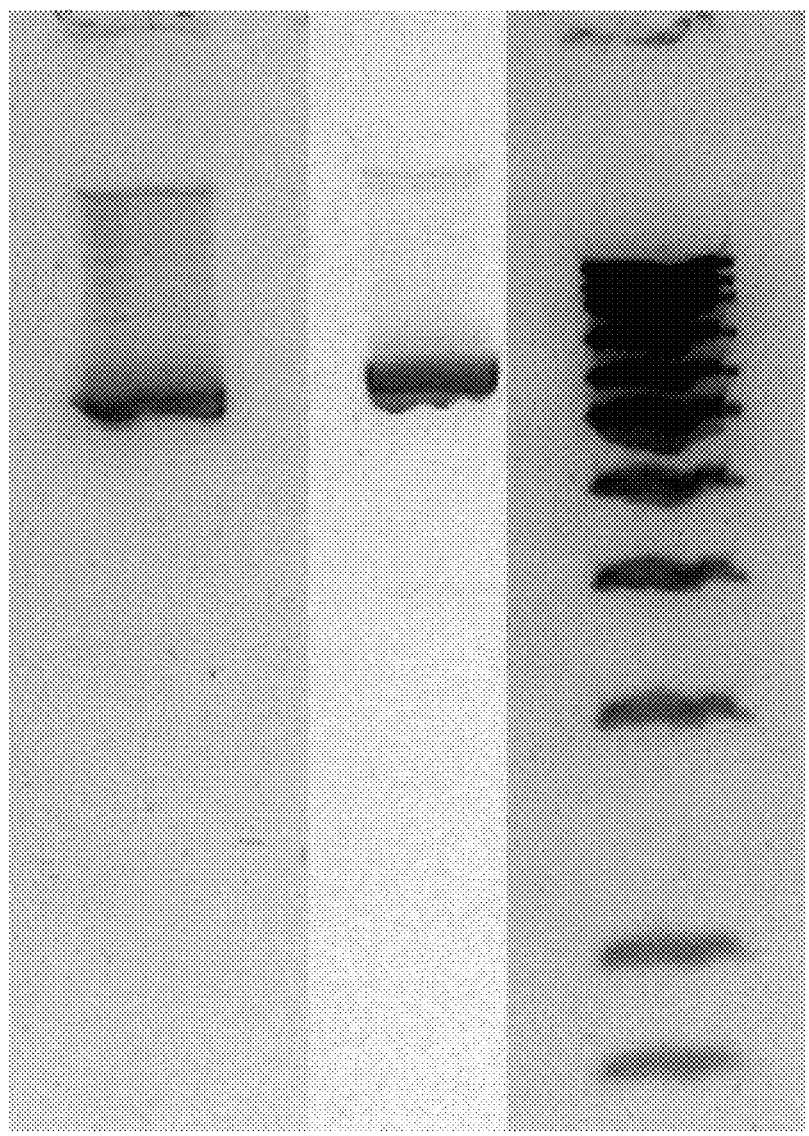
FIG. 8 is an SDS-PAGE gel associated with Example 31.

An unpurified his-tagged DNA polymerase was used in a standard PCR reaction to amplify a 450 bp fragment from an *E. coli* plasmid. A sample of the polymerase was purified using a Ni-NTA extraction capillary, and used to amplify the same fragment under the same conditions. The products of the reactions were analyzed by SDS-PAGE of the PCR reaction (shown in FIG. 8). Lane 1 is the reaction using unpurified polymerase, lane 2 is the reaction using purified polymerase, and lane 3 is molecular weight markers. Note that the processed polymerase retains its enzymatic activity.

Example 32

Attaching Polyacrylamide to a Capillary Channel

A 200 µm ID 50 cm capillary is etched according to Example 1. The fused silica capillary is reacted with a solution of γ-methacryloxypropyl-trimethoxysilane (Sigma-Aldrich, Milwaukee, Wis., PN 44,015-9) (30 µL mixed with 1.0 mL of 60% (v/v) acetone/water). The capillary is filled, the flow is stopped and the capillary wall reacted at room temperature. After 1 hour, the capillary is flushed with water to stop the reaction. Then the capillary is reacted with a solution of acrylamide. A solution of 3% (v/v) acrylamide with catalyst is prepared and immediately pumped into the capillary. Acrylamide (30 µL) is mixed with a 1.0 mL degassed water solution containing 2 mg of ammonium persulfate and 0.8 mg of TEMED (N,N,N',N'-tetramethyl-ethylenediamine). The capillary is filled rapidly at 50 µL/min, the flow is stopped and the capillary reacted at room temperature for 1 hour. After 1 hour, the capillary is flushed with deionized water to stop the reaction. Alternatively, the acrylamide polymerization solution can be prepared at 4° C., pumped into the capillary and polymerization solution allowed to warm up to room temperature and react for 1 hour. Finally, the capillary is flushed and stored in deionized water.

Example 33

Bonding IDA, NTA, and CMA Chelating Groups to Fused Silica Capillary Channel

A 200 μm ID 100 cm length capillary is etched according to Example 1. The capillary is filled with a 100° C. solution of 10% (v/v) γ-glycidoxypropyl-trimethoxysilane (Sigma-Aldrich, Milwaukee, Wis., PN 44,016-7) in dry toluene and reacted for 1 hour at 10 μL/min. This treatment is repeated twice. The capillary is flushed with 100% HPLC grade methanol. To make IDA chelator, the epoxy bonded capillary is filled and reacted with a 65° C. solution of 10% (w/v) solution of iminodiacetic acid in methanol adjusted to pH 8.2 with lithium hydroxide for 4 hours at 10 μL/min. To make the NTA chelator, epoxy activated capillary is reacted with a 65° C. solution of 10% (w/v) solution of R-substituted nitrilotriacetic acid, either N-[3-amino-1-carboxypropyl]-iminodiacetic acid or N-[5-amino-1-carboxypentyl]-iminodiacetic acid, in methanol adjusted to pH 7.5 with lithium hydroxide for 4 hours at 10 μL/min. The synthesis procedures of R substituted NTA reagents are described in U.S. Pat. No. 4,877,830. For the carboxymethylated aspartate (CMA) metal chelate capillary channel, a solution of L-aspartic acid (100 mg/mL) is adjusted to pH 8.6 with sodium carbonate and pumped through the capillary channel at a rate of 5 μL/min at 30° C. for 12 hours. The capillary is washed with deionized water and a solution of bromoacetic acid (100 mg/mL) adjusted to pH 8.6 with sodium carbonate is pumped through the capillary channel at a rate of 5 μL/min at 30° C. for 12 hours. The capillary channel is washed with deionized water and is ready to be converted to the metal chelated form by pumping with a metal salt solution as described in U.S. Pat. No. 5,962,641. The excess epoxide groups are endcapped with a 1 M aqueous solution of ethanolamine for one hour at room temperature. Finally, the chelator capillary is flushed and stored in deionized water.

The chelator capillary is converted to the metal chelate form before use. This is accomplished by flushing the capillary with the appropriate metal salt solution. The capillary is flushed for 30 minutes each of 30 mM disodium EDTA and deionized water, and then flushed with either 0.2 M $ZnCl_2$, 0.2 M $NiCl_2$, $Hg(NO_3)_2 \cdot H_2O$ or $FeCl_3$ in 1 mM $HNO_3$ to convert the capillary to the Zn form, Ni form, or the Fe form respectively. The capillary is washed and stored with deionized water.

Example 34

Procedure For Immobilizing Protein G, Protein A, Protein A/G, and Protein L on a Fused Silica Capillary Channel A 200 μm ID 100 cm length capillary is etched according to Example 1. The capillary is filled with 10% w/v γ-glycidoxypropyltrimethoxysilane (Sigma-Aldrich, Milwaukee, Wis., PN 44,016-7) in dried toluene, and then the capillary is heated under slow flow conditions of 1 μL/min at 50° C. for 4 hours. The capillary is cooled, washed for 30 minutes each with toluene and methanol, and then deionized water. The capillary is filled with solution of protein G solution (5 mg/ml in 10 mM phosphate buffer, pH 7.5). The protein may be native Protein G (Calbiochem, San Diego, Calif., PN 539302-Y) which will attach through native lysine residues or recombinant Protein G from (Calbiochem, San Diego, Calif., PN 539303-Y) which will attach through a poly-lysine fusion tag at the protein terminus. The capillary is reacted by pumping the protein solution through capillary at 1 μL/min at 25° C. for 4 hours. The capillary is flushed and conditioned with 10 mM phosphate buffer solution pH 7.0 for 1 hour and then flushed and stored with deionized water at 4° C. until used.

In addition to Protein G, others, such as recombinant Protein L (Pierce, Rockford, Ill., PN 21189), recombinant Protein A (Calbiochem, San Diego, Calif., PN 539203-Y), and recombinant Protein A/G (Pierce, Rockford, Ill., PN 21186) may be used with the procedures described in this example.

Example 35

Immobilizing Single Strand and Double Strand DNA on Fused Silica Capillary Channels Using a Streptavidin Biotin Synthesis Reaction A 150 μm ID 75 cm length capillary is etched according to Example 1. The capillary is then filled with a 65° C. 4% (v/v) solution of 3-aminopropyltriethoxy-silane in methanol and reacted for 12 hours with a slow flow of 2 μL/min. After flushing with 100% methanol and then deionized water, the tube is filled with a 5.0 mg/mL NHS-LC biotin (Quanta BioDesign, Ltd., Powell, Ohio, PN 10206) in 50 mM sodium bicarbonate solution pH 8.3 and reacted for 4 hours at room temperature. N-hydroxysuccinimidobiotin (NHS-biotin), an alternative molecule, is also used (Quanta BioDesign, Ltd., Powell, Ohio, PN 10205; or Sigma-Aldrich, Milwaukee, Wis., PN H1 759). An NHS-biotin reagent containing a hydrophilic polyethylene glycol spacer (NHS-dPEG$_4$™-Biotin, Quanta BioDesign, Ltd., Powell, Ohio, PN 10200) is used under the same reaction conditions as the other biotin reaction reagents.

Following biotinylation the capillary is flushed with deionized water and then the capillary is filled with 4.0 mg/ml solution of streptavidin (Sigma-Aldrich, Milwaukee, Wis., PN S0677) in 50 mM sodium phosphate buffer (pH 7.3). The streptavidin solution is reacted for 4 hours at 4° C. and any remaining free streptavidin is removed by rinsing the capillary tube with deionized water. The streptavidin capillary is stored in a refrigerator until the final attachment of the biotinylated DNA.

In some cases, single-stranded DNA is immobilized to the wall of the capillary by quickly heating the biotinylated double-stranded DNA PCR product to 95° C. for several minutes followed by rapid cooling to 5° C. and immediately pumping the solution into the reactor. Excess template is removed by rinsing with deionized water. The deionized water may be heated to ensure complete denaturing of the DNA and retention of single-stranded DNA. Alternatively biotinylated single-stranded DNA may be prepared and purified and then introduced into the streptavidin capillary. Double-stranded DNA is immobilized to the wall of the capillary by pumping biotinylated double-stranded DNA PCR product without prior heating.

Example 36

Purifying a (His)$_6$ Fusion Protein Integrated with Arraying the Protein onto a Protein Chip A capillary of dimensions 25 cm×100 μm ID is functionalized with an NTA-Ni(II) chelator bonded according to the procedure described in Example 33. The capillary is coiled "figure 8" type configuration with 6 mm diameter coils with 5 cm straight sections on top and bottom of the configuration. The capillary is connected to a syringe pump (Tecan Systems, San Jose, Calif., CAVRO Model No. XP-3000) fitted with 100 μl or 1 mL syringe connected to one end of the open tube capillary, and the other end is movable and is connected to an apparatus where the materials may be taken up or deposited at different locations. The capillary is conditioned by drawing up 20 mM sodium phosphate, 0.5 M sodium chloride, 10 mM imidazole, pH 7.4 at the rate of 25 μL/min for 2 minutes. The buffer is expelled and the capillary is filled with a 100 μL sample of clarified whole-cell lysate of *E. coli* expressing a fusion protein with a $His_6$ tag and a terminal cysteine residue. The sample is drawn repeatedly over the capillary surface at the rate of 25 μL/min so that the total 100 μL sample passes back and forth 3 times for a total of 6 passes over the capillary surface. The remaining sample is blown out of the capillary with 3 psi air, and 10 μL of standard PBS (0.9% w/v NaCl, 10 mM sodium phosphate, pH 7.2) wash buffer is drawn into and out of the capillary at a rate of 25 μL/min. This is done for a total of 3 cycles over the capillary surface, and the remaining wash solution is blown out of the capillary with 3 psi air. A small plug, 50 mL (approximately 7 mm in length), of desorption buffer, 20 mM sodium phosphate, 0.5 M sodium chloride, 0.5 M imidazole, pH 7.4 is drawn into the capillary, and is passed over the capillary surface a total of six times at a rate of 5 μL/min. This elution plug is positioned at the opening of the capillary column, and a portion (10 mL) is deposited on a bare gold grating-coupled SPR chip for covalent attachment through the terminal cysteine's thiol group. Attachment of proteins to gold surfaces via cysteine residues, along with descriptions of collecting GC-SPR data from these surfaces, has been described previously. (Jennifer Brockman et al., Poster Presentation "Grating-Coupled SPR," *Antibody Engineering Conference*, Dec. 2-6, 2001, San Diego, Calif.).

Example 37

Purifying A Monoclonal Human IgG Protein

A capillary of dimensions 35 cm×100 μm ID is functionalized with an extraction phase on a capillary of recombinant Protein G bonded according to the procedure described in Example 34. The capillary is a straight configuration where one end is movable and connected to a pumping means and the other end is movable and connected to an apparatus where the material may be taken up or deposited at different locations. The pumping means is a 200 μL vial that may be filled with conditioning fluid, sample, washing fluid or nitrogen gas. The vial is filled with the various fluids by draining and forcing the old fluid out and then refilling with the new fluid several times until the vial is rinsed and ready for use. The vial is pressurized to force fluids through the capillary usually at a pressure of 0.1 to approximately 300 psi depending on the diameter and length of the capillary. For this capillary, a pressure of 3 psi is used.

The capillary is conditioned with 100 mM sodium phosphate, 100 mM sodium citrate, 2.5 M sodium chloride, pH 7.4 at the pressure of 3 psi for 10 minutes. The buffer is expelled and the capillary is pumped with 300 μL hybridoma cell culture supernatant sample (preferably, but not necessarily, free from fetal bovine serum) containing monoclonal human IgG. The capillary is washed with 100 mM sodium phosphate, 100 mM sodium citrate, 2.5 M sodium chloride, pH 7.4 at the pressure of 3 psi for 10 minutes. The washing step may be omitted in cases where the enrichment is high and a small amount of residual sample material can be tolerated.

The wash solution is blown out of the capillary and a small plug, 50 mL (approximately 7 mm in length), of desorption buffer of 100 mM sodium phosphate, 100 mM sodium citrate, pH 3.0 is pumped through the capillary and deposited directly into a vial containing 40 mL of neutralization buffer of 100 mM $H_2NaPO_4$/100 mM $HNa_2PO_4$, pH 7.5. Alternatively, the desorption solution is introduced as a stream rather than a segment of liquid. The desorption process is performed so that the leading edge of the stream contains the desorbed material and the first 2 cm length of the stream (150 mL) is directed and deposited in directly into a vial containing 40 mL of neutralization buffer of 100 mM $H_2NaPO_4$/100 mM $HNa_2PO_4$, pH 7.5. The remaining portion of the stream is directed to waste. Alternatively, the leading edge desorption process is performed directly into the wash buffer or the sample. The desorption buffer containing 100 mM sodium phosphate, 100 mM sodium citrate, adjusted to pH 3.0 is pumped into the capillary containing residual wash buffer or sample. In this example, for the rate at which the desorption buffer is pumped into the capillary, it will take 5.0 minutes for the leading edge to start to exit the end of the tube. The sample or wash in the capillary is directed to waste. Then, the flow for the time segment of 5.0-5.3 minutes is directed and deposited directly into a vial containing 40 mL of neutralization buffer of 100 mM $H_2NaPO_4$/100 mM $HNa_2PO_4$, pH 7.5. The remaining portion of the stream is directed to waste.

Alternatively, a Protein L capillary channel as described in Example 34 can be used in this example.

Example 38

Purifying a Monoclonal Human IgG Protein with Arraying onto a Protein A-Functionalized Protein Chip A capillary of dimensions 100 cm×200 μm ID is functionalized with an extraction phase on a capillary of recombinant Protein G bonded according to the procedure described in Example 34. The capillary is a straight configuration where one end is movable and connected to a pumping means and the other end is movable and is connected to an apparatus where the material may be taken up or deposited at different locations. The pumping means is a 200 μL vial that may be filled with conditioning fluid, sample, washing fluid or nitrogen gas. The vial is filled with the various fluids by draining and forcing the old fluid out and then refilling with the new fluid several times until the vial is rinsed and ready for use. The vial is pressurized to force fluids through the capillary usually at a pressure of 0.1 to approximately 300 psi depending on the diameter and length of the capillary. For this capillary, a pressure of 3 psi is used.

The capillary is conditioned with 100 mM sodium phosphate, 100 mM sodium citrate, 2.5 M sodium chloride, pH 7.4 at the pressure of 3 psi for 10 minutes. The buffer is expelled and the capillary is pumped with 1,000 μL hybridoma cell culture supernatant sample (preferably, but not necessarily, free from fetal bovine serum) containing monoclonal human IgG. The capillary is washed with 100 mM sodium phosphate, 100 mM sodium citrate, 2.5 M sodium chloride, pH 7.4 at the pressure of 3 psi for 10 minutes. The washing step may be omitted in cases where the enrichment is high and a small amount of residual sample material can be tolerated.

The wash solution is blown out of the capillary and a small plug, 2 μL (approximately 6.4 cm in length), of desorption buffer of 100 mM sodium phosphate, 100 mM sodium citrate, adjusted to pH 3.0 is pumped into the capillary. This segment of fluid is passed over the inner capillary surface a total of five (5) times at flow rate of 30 µL/min. The complete segment is then deposited directly into a 384-well plate where an individual well contains 2 µL of neutralization buffer of 100 mM $H_2NaPO_4$/100 mM $HNa_2PO_4$, pH 7.5. The sample is then arrayed by available means onto a Protein A-coated grating-coupled SPR (GC-SPR) chip, for subsequent analysis of target binding to the antibody. The apparatus, procedures and conditions used for preparation of the Protein A-coated GC-SPR chip, arraying of the chip, and collection of the associated SPR data have been described (Jennifer Brockman et al., Poster Presentation "Grating-Coupled SPR," *Antibody Engineering Conference, Dec. 2-6, 2001*, San Diego, Calif.).

Alternatively, a Protein L capillary channel as described in Example 34 can be used in this example.

Example 39

Phage Display Screening of Fab Antibody Fragments with Label-Free Grating-Coupled SPR Phage-derived clones for different Fab antibody fragment sequences are released as whole-cell bacterial lysates, where there are two fusion tags on the Fab antibody fragment-one c-myc (for purification) and the other a terminal cysteine residue (for immobilization). The clarified lysate is passed through an open-tube separation capillary (Polymicro Technologies, Phoenix, Ariz.) of dimensions 200 µm ID and 60 cm with Protein G, as described in Example 34, immobilized on its surface, and an anti-c-myc monoclonal or polyclonal antibody is bound by the Protein G (a bifunctional linker covalently attaches the antibody to the Protein G; the bifunctional linker is dimethylpimelimidate (DMP); procedure for successful crosslinking are provided within "ImmunoPure Protein G IgG Orientation Kit" instructions (Pierce, Rockford, Ill., PN 44896). Once the Fab antibody fragment is trapped by the anti-c-myc antibody on the inside tube wall, a very small volume slug (1 µL) of 10 mM phosphoric acid (pH 2.3) is introduced to the tube, and is moved back and forth across the internal walls to desorb the Fab antibody fragment from the immobilized anti-c-myc. This is ejected from the tube into 250 mL of phosphate neutralization buffer (100 mM $H_2NaPO_4$/100 mM $HNa_2PO_4$, pH 7.5), bringing the pH to ~7.0. This is then ready for covalent spotting onto a grating-coupled surface plasmon resonance array (GC-SPR), where the surface chemistry is based upon the terminal cysteine's thiol group bonding with the gold surface of the GC-SPR chip. In addition, the desorption/neutralization process can be performed within the spotting apparatus itself so that the Fab antibody fragments are fully processed as part of a larger integrated chip preparation process.

In addition to Protein G, Protein A or Protein A/G (as described in Example 34) may be used in the procedures described in this example.

Example 40

Extracting Multi-Protein DNA-Binding Complexes with Mass Spectrometric Identification of the Complex Composition A 150 µm ID 75 cm length capillary is etched according to Example 1. The capillary is then filled with a 65° C. 4% (v/v) solution of 3-aminopropyltriethoxysilane in methanol and reacted for 12 hours at a slow flow of 1 µL/min. After flushing with 100% methanol and then deionized water, the tube is filled with a 5.0 mg/mL NHS-LC biotin (N-hydroxysuccinimido-biotin, Sigma-Aldrich, Milwaukee, Wis., PN H1759) in 50 mM sodium bicarbonate solution pH 8.3 and reacted for 4 hours at room temperature. Following biotinylation the capillary is flushed with deionized water and then the capillary is filled with 4.0 mg/ml solution of streptavidin (Sigma-Aldrich, Milwaukee, Wis., PN S0677) in 50 mM sodium phosphate buffer (pH 7.3). The streptavidin solution is reacted for 4 hours at 4° C. and any remaining free streptavidin is removed by rinsing the capillary tube with deionized water.

DNA sequences being screened for their interactions with multi-protein complexes are prepared. In all cases the target sequence is biotinylated at its 5' end. An of multi protein complexes are described in Eckhard Nordhoff, et al., *Nature Biotech.*, 17:884 (1999). Short single-stranded biotinylated DNA (<50 bp) is prepared by standard DNA synthesis techniques (i.e. oligonucleotide synthesis). Long single-stranded biotinylated DNA ($\geqq$50 bp) is prepared by standard PCR techniques, whereby one or both of the PCR primers is 5'-labeled with biotin. The primers are removed after the PCR reaction by standard purification techniques, including DNA Chromatography (Douglas Gjerde, et al., *DNA Chromatography*, Chapter 6, Wiley-VCH, Weinheim, Germany (2002)). The purified PCR product is then heated to >95° C. and then cooled immediately to 4° C. to produce single-stranded biotinylated DNA. Long double-stranded biotinylated DNA ($\geqq$50 bp) is prepared in the manner identical to the single-stranded variety, except for elimination of the final heat denaturation and cooling step.

Once the biotinylated DNA of interest is suitably prepared, it is allowed to incubate with the proteins being screened for their DNA interactions. The proteins will most often be derived from whole-cell extracts, nuclear extracts, or any other source of DNA-binding proteins that have been prepared by standard means. Biotinylated DNA (100 ng) is added to the extract and is allowed to incubate in the manner described previously for extraction of DNA-binding proteins (Eckhard Nordhoff, et al., *Nature Biotech.*, 17:884 (1999)). Once the incubation is complete, the unbound biotinylated DNA is removed from the sample by its selective precipitation with polyethyleneimine (PEI), in the manner described previously for the precipitation and removal of DNA (Jesper Svejstrup, et al., *Proc. Natl. Acad. Sci. USA*, 94:6075 (1997)). Once the unbound DNA is removed, the entire sample that contains the protein-bound biotinylated DNA is introduced into the streptavidin capillary described above. The entire sample is fully drawn up into and pushed out of the capillary at a flow rate of 50 µL/min, and this action is repeated 5 times. Once completed, the capillary is washed by separately drawing up and pushing out to waste 15 µL of water at 100 µL/min, and this action is repeated 5 times. The capillary is then evacuated by flowing 10 psi of air through the capillary for 30 seconds. A single 1 µL segment (approximately 5.6 cm in length) of 50% methanol/50% water is then fully drawn into the capillary, and passing this elution slug over the entire streptavidin surface a total of 5 times at 20 µL/min. The entire 1 µL elution volume that contains the eluted proteins bound to the original DNA sequence is then pushed into an electrospray nozzle (Advion NanoMate™ 100, Advion Biosciences, Inc., Ithaca, N.Y.; Nanospray needle holder, PN NSI-01 and NSI-02, Nanospray needles, PN NSI-NDL-01 and NSI-NDL-02, LC Packings Inc., San Francisco, Calif.), which is in turn analyzed by ESI-MS/MS (examples of such electrospray nozzles, and their use with MS and MS/MS are described at Xian Huang, et al., Proceedings of the $50^{th}$ ASMS Conference on Mass Spectrometry and Allied Topics, Orlando, Fla., Jun. 2-6, 2002. The ESI-MS/MS is then used for identification of the proteins that comprise the DNA-binding complex, in a manner described previously (Martin Yarmush, et al., *Annu. Rev. Biomed. Eng.*, 4:349 (2002)).

Example 41

Purification of Specific Nucleic Acid Sequence Using a Nucleic Acid Modified Capillary Channel A 100 µm ID and 25 cm length capillary is prepared with a single strand DNA group prepared according described in Example 35. The nucleic acid strand attached to the capillary channel is a 20 mer oligonucleotide with a sequence of attgc-cgggtttaatagcg. The capillary is a straight configuration connected to a syringe pump (Tecan Systems, San Jose, Calif., CAVRO Model No. XP-3000) fitted with 100 µl or 1 mL syringe connected to one end of the open tube capillary, and the other end is movable and is connected to an apparatus where the materials may be taken up or deposited at different locations.

A 50 µL solution containing 0.01 µg of 20 mer oligonucleotide with the complementary sequence of taacgggcccaaat-tatcgc in 10 mM sodium phosphate buffer, pH 7.0 is passed through the capillary at a rate of 10 µL/min at room temperature and the sample nucleic acid is hybridized to the complementary strand attached to the channel wall. The tube is washed with 10 µL of 100% deionized water and is expelled from the capillary. The capillary is placed in an oven and a hot 90° C. solution of 10 cm segment of solution of 10 mM Tris-HCl 0.1 mM EDTA (disodium salt) pH 8.0 is passed slowly through the capillary channel denaturing and desorbing complementary strand of nucleic acid and depositing the denatured nucleic into a vial.

Example 42

Bonding a Carboxylic Acid, a Weak Acid Cation Exchanger to a Capillary Channel

A 200 µm ID 50 cm capillary is etched according to Example 1. The fused silica capillary is reacted with a solution of γ-methacryloxypropyl-trimethoxysilane (Sigma-Aldrich, Milwaukee, Wis., PN 44,015-9) (30 µL mixed with 1.0 mL of 60% (v/v) acetone/water). The capillary is filled, the flow is stopped and the capillary reacted at room temperature. After 1 hour, the capillary is flushed with water to stop the reaction. Then the capillary is flushed with dry THF. Flush the capillary with deionized water. Flush the capillary with THF and then deionized water. Then, the capillary is filled with an acrylic acid monomer solution made up by the following procedure taking 30 µL of acrylic acid free of free radical scavengers (Sigma-Aldrich, Milwaukee, Wis.) and mixing it with a 1.0 mL degassed 0.05 M sodium phosphate buffer solution, pH 7.0 containing 2 mg of ammonium persulfate and 0.8 mg of TEMED (N,N,N',N'-tetramethylethylene-di-amine). The capillary is filled rapidly at 50 µL/min, the flow is stopped and the capillary reacted at room temperature. After 2 hours, the capillary is flushed with deionized water to stop the reaction. Alternatively, the polymerization solution can be prepared at 4° C., pumped into the capillary and polymerization solution allowed to warm up to room temperature and react for 2 hours. Finally, the capillary is flushed and stored in deionized water.

Example 43

Preparation of a Hydrophobic Capillary Channel Suitable for Hydrophobic Interaction of a Protein A 200 µm ID 50 cm length capillary is prepared with a carboxylic acid group according to the procedure described in Example 42. Alternatively, the carboxylic acid capillary can be formed by 2 other synthesis routes. In Route 1, the capillary prepared from the procedure in Example 1 is filled with 70° C. solution of neat thionyl chloride and reacted for 12 hours at 10 µL/min. The capillary is flushed with dry THF and then filled a 50° C. solution 20% (v/v) of vinylmagnesium bromide in tetrahydrofuran (THF) (Sigma-Aldrich, Milwaukee, Wis., PN 25, 725-7) and reacted for 12 hours at 10 µL/min. The capillary is flushed with THF and then deionized water. The capillary is filled with a solution of 10% (v/v) 3-mercapto propionic acid (Sigma-Aldrich, Milwaukee, Wis., PN M580-1) in a 3% aqueous hydrogen peroxide or a 50° C. solution of 10% (v/v) Thio-dPEG$_4$™ acid (Quanta BioDesign, Powell, Ohio, PN 10247) in a 3% aqueous hydrogen peroxide and reacted for 12 hours at 2 µL/min. Then the capillary is flushed with deionized water. In Route 2, the capillary is prepared from the procedure in Example 1 is filled and reacted with a neat solution of allyldimethylchlorosilane (Petrarch Systems Inc., Levittown, Pa., PN A0552) or allyl-triethoxysilane (Petrarch Systems Inc., Levittown, Pa., PN A0564) at a flow rate of 1 µL/min at room temperature. After 6 hours, the capillary is flushed with 100% methanol and then deionized water to stop the reaction. The capillary is filled with a solution of 10% (v/v) 3-mercaptopropionic acid (Sigma-Aldrich, Milwaukee, Wis., PN M580-1) in a 3% aqueous hydrogen peroxide or a 50° C. solution of 10% (v/v) Thio-dPEG$_4$™ acid (Quanta BioDesign, Ltd., Powell, Ohio, PN 10247) in a 3% aqueous hydrogen peroxide and reacted for 12 hours for 2 µL/min. Then the capillary is flushed with deionized water.

The carboxylic acid capillary from above is filled with an aqueous solution of EDC (1-Ethyl-3-(3-dimethylaminopro-pyl)-carbodiimide) (Sigma-Aldrich, Milwaukee, Wis., PN 16, 146-2) and sulfo-NHS (sodium salt of N-hydroxysulfos-uccinimide) (Sigma-Aldrich, Milwaukee, Wis., PN 56485) 10% each (w/v) and reacted at room temperature for 6 hours. The capillary is flushed with deionized water and then 100% methanol and then filled with 10% (w/v) solution of 4-phe-nylbutylamine in methanol and reacted at room temperature for 2 hours. The capillary is flushed with 100% methanol and stored at 4° C. until use.

Alternatively, a 200 µm ID 100 cm length capillary is etched according to Example 1. The capillary is filled with a 50° C. neat solution of phenethyltrimethoxysilane (Gelest, Tullytown, Pa., PN SIP6722.6) and then the capillary is heated under slow flow conditions of 1 µL/min for 4 hours at 2 µL/min. The capillary is cooled, washed for 30 minutes each with toluene and then 100% methanol.

Example 44

Preparing A C18 Reverse Phase Capillary Channel

A 200 µm ID 100 cm length capillary is etched according to Example 1. The etched capillary tube is filled with 10% (w/v) colloidal silica solution and sealed (Ludox HS-40, Du Pont, Wilmington, Del.) and heated to 250° C. for 1 hour. This treatment is repeated 3 times and finally the capillary is flushed with HPLC grade ethanol. The capillary is filled with an 80° C. solution of 0.2 g/mL dimethyloctadecyl-chlorosilane or octadecyltrichlorosilane (Petrarch Systems Inc., Bristol, Pa., USA) in toluene, and reacted for 2 hours at 10 μL/min. This treatment is repeated twice. The capillary is endcapped by filling the capillary with 80° C. 0.2 g/mL solution of methyltrichlorosilane in toluene reacted for 2 hours at 10 μL/min. After this treatment, the capillary is flushed and stored with 100% HPLC grade methanol.

Example 45

Desalting a Protein Using a Hydrophobic Capillary Channel

A capillary of dimensions 200 μm i.d and 50 cm length is functionalized with a hydrophobic surface bonded according to the procedure described in Example 43. Alternative, a capillary of dimensions 200 μm i.d and 50 cm length is functionalized with a hydrophobic $C_{18}$ surface bonded according to the procedure described in Example 44. The capillary is coiled "figure 8" type configuration with 6 mm diameter coils with 5 cm straight sections on top and bottom of the configuration. The capillary is connected to a syringe pump (Tecan Systems, San Jose, Calif., CAVRO Model No. XP-3000) fitted with 100 μl or 1 mL syringe connected to one end of the open tube capillary, and the other end is movable and is connected to an apparatus where the materials may be taken up or deposited at different locations.

The sample is a 200 μl solution containing 0.1 μg of IgG proteins in a 1.5 M ammonium sulfate buffer. The sample is introduced into the capillary by passing the solution back and forth for 3 cycles and the protein is adsorbed to the hydrophobic phase of the capillary channel. The remaining sample solution is blown out of the capillary and a small 10 cm segment of 100% deionized water is passed through the capillary, desorbing the protein from the wall and the sample is deposited into a vial for analysis.

Example 46

Procedure for Purification of Protein Kinase a with a Reverse Phase Capillary Channel and Ion Pairing Reagent A capillary of dimensions 100 μm ID and 25 cm length is functionalized with a reverse phase surface bonded according to the procedure described in Example 44. The capillary is a straight configuration connected to a syringe pump (Tecan Systems, San Jose, Calif., CAVRO Model No. XP-3000) fitted with 100 μL syringe connected to one end of the open tube capillary, and the other end is movable and is connected to an apparatus where the materials may be taken up or deposited at different locations.

The sample is a 100 μL solution containing 0.1 ug of Protein kinase A in a phosphate buffer saline (0.9% w/v NaCl, 10 mM sodium phosphate, pH 7.2) (PBS) buffer. Ten μL of 10% aqueous solution of trifluoroacetic acid (TFA) is added so that the final volume of the solution is 110 μL and the concentration of the TFA in the sample is 0.1%. The sample is introduced into the capillary and the protein/TFA complex is adsorbed to the reverse phase of the capillary channel.

The sample is blown out of the capillary and a small 10 cm segment of 50% (v/v) acetonitrile/water is passed through the capillary, desorbing the protein from the wall and the sample is deposited into a vial for analysis.

Alternatively, the capillary channel may be washed with 10 μL of aqueous 0.1% TFA. This solution is ejected from the capillary channel and the protein is desorbed and deposited into the vial.

If necessary, alternatively 1% heptafluorobutyric acid (HFBA) is used as the ion pairing reagent to reduce the ion suppression effect of the ion pairing reagent when the sample is analyzed by electrospray ion trap mass spectrometry.

Example 47

Purification of Nucleic Acid Mixture with Reverse Phase Capillary Channel and Ion Pairing Reagent A capillary of dimensions 100 μm ID and 25 cm length is functionalized with a reverse phase surface bonded according to the procedure described in Example 44. The capillary is straight configuration connected to a syringe pump (Tecan Systems, San Jose, Calif., CAVRO Model No. XP-3000) fitted with 100 μL syringe connected to one end of the open tube capillary, and the other end is movable and is connected to an apparatus where the materials may be taken up or deposited at different locations.

A 100 μL sample containing 0.01 μg of DNA is prepared using PCR amplification of a 110 bp sequence spanning the allelic MstII site in the human hemoglobin gene according to the procedure described in U.S. Pat. No. 4,683,195. A 10 μL concentrate of triethylammonium acetate (TEAA) is added so that the final volume of the solution is 110 μL and the concentration of the TEAA in the sample is 100 mM. The sample is introduced into the capillary and the DNA/TEAA ion pair complex is adsorbed to the reverse phase of the capillary channel.

The sample is blown out of the capillary and a small 10 cm segment of 50% (v/v) acetonitrile/water is passed through the capillary, desorbing the DNA from the wall and the sample is deposited into a vial for analysis.

Example 48

Hydroxide Etch-Conditioning a Capillary Channel

Capillaries (Polymicro Technologies, Phoenix, Ariz.) of dimensions 25, 50, 75, 100, 150, 200, 250, and 300 μm ID and lengths of 1 cm to 5 meters were obtained. In this example, a 100 μm ID 1 meter length fused silica capillary was filled with 0.1 M sodium hydroxide and flushed at room temperature for 1 hour. Then, the base solution was removed by rinsing with HPLC grade deionized water for 30 minutes. The solution was changed to 0.1 M HCl and the capillary was flushed for 30 minutes. Then the solution was changed to HPLC grade deionized water and the capillary was flushed for 15 minutes and was finally flushed and stored with HPLC grade acetone. Solvent flow rates were 10 μL/min. Increasing or decreasing the diameter of the channel being etched will increase or decrease the flow rate of the solvents used.

Example 49

Procedure for Preparation and Use of Protein G Capillary Channel

Two 200 μm ID 114 cm length sections of fused silica capillary were etched according to the procedure described in Example 48. The capillaries were then dried at 160° C. for three hours with a continual stream of nitrogen. A 15% solution of γ-glycidoxypropyltrimethoxysilane (Sigma-Aldrich, Milwaukee, Wis., PN 44,016-7) in dry toluene (Sigma-Aldrich, Milwaukee, Wis., 99.8% anhydrous) was passed through the capillary at 110° C. for three hours at a rate of 60 μL per minute by gravity. The silane reservoir was refilled once during this time period.

Seven centimeters were cut from each end to produce the 100 cm capillary needed. A 25 mL volume was placed over sodium and distilled to obtain the dry toluene. This solution was used for making the silane reagent. One capillary was rinsed with toluene to remove the silane reagent and stored overnight. Binding of protein G was done the next day. One mg of Protein G (CalBiochem, San Diego, Calif., PN 539303) was dissolved in 500 μL of sodium phosphate buffer at pH=8.0, 25 mM buffer concentration. The capillary was air flushed to remove toluene, rinsed briefly with methanol to remove any adsorbed toluene on the silica surface, and then rinsed briefly with water. The protein G was now flushed through the capillary monitoring the capillary end with litmus paper until the pH was basic (about pH of 8). Two column volumes of protein G were then allowed to pass through the capillary. Then the filled capillary ends were pressed into a GC septum to seal the capillary and placed in a 37° C. air oven for 3.5 hours.

Twenty μL of 4.9 mg/mL anti-FLAG M2 mouse monoclonal IgG$_1$ sample (Sigma-Aldrich, Milwaukee, Wis., PN, F-3165) was aspirated into 1 meter of the Protein G capillary, thus occupying roughly two-thirds of the 30 μL internal volume of the capillary. This 20 μL sample zone was visually monitored and pulled with a 50 μL syringe to the top of the capillary without allowing it to leave the capillary. The sample zone was allowed to incubate in the capillary at room temperature for five minutes, thus leaving 10 μL of internal volume unoccupied at the bottom of the capillary. The sample zone was then pushed to the bottom of the capillary in the same manner without allowing it to leave the capillary and was allowed to incubate in the capillary at room temperature for five minutes, thus leaving 10 μL of internal volume unoccupied at the top of the capillary. This process of incubating the sample zone at the top and bottom of the capillary was repeated twice for this same sample, followed by finally expelling the sample zone from the capillary with 1 mL of air flowing at 10-20 mL/min. This capillary was then washed with 10 mM NaH$_2$PO$_4$/10 mM Na$_2$HPO$_4$ buffer, pH 7 by passing 500 μL of the buffer through the capillary at 1 mL/min, followed by expelling of the buffer from the capillary with 1 mL of air flowing at 10-20 mL/min.

Ten μL of 14.7 mM phosphoric acid (pH 2.2) was aspirated into this same capillary, thus occupying roughly one-third of the 30 μL internal volume of the capillary. This 10 μL elution zone was visually monitored and pulled with a 50 μL syringe to the top of the capillary without allowing it to leave the capillary and was allowed to incubate in the capillary at room temperature for one minute, thus leaving 20 μL of internal volume unoccupied at the bottom of the capillary. The elution zone was then pushed to the bottom of the capillary in the same manner without allowing it to leave the capillary and was allowed to incubate in the capillary at room temperature for one minute, thus leaving 20 μL of internal volume unoccupied at the top of the capillary. This process of incubating the elution zone at the top and bottom of the capillary was repeated twice for this same elution zone, followed by finally expelling and collection of the elution zone into a 0.5 mL Eppendorf vial with 1 mL of air flowing at 10-20 mL/min. This collected elution zone was combined with 10 μL of Bradford assay reagent (Pierce, Rockford, Ill., PN 23236), was allowed to incubate for ten minutes at room temperature, and an absorbance reading was taken of it at 595 nm with a SpectraPhysics detector (Spectra FOCUS forward optical scanning detector). Calibration was performed by measuring a 14.7 mM phosphoric acid blank and 490 μg/mL anti-FLAG IgG$_1$ standard in 14.7 mM phosphoric acid, each combined with equal volumes of Bradford assay reagent. Analysis of the eluted sample against the calibration indicated that 2.5 μg of IgG was trapped and eluted from the Protein G capillary into 10 μL of 14.7 mM phosphoric acid (corresponding to a concentration of 250 μg/mL IgG in the eluted zone).

Example 50

Procedure for Ni-NTA Trapping of His-Tagged GST Protein Standard

A capillary of dimensions 200 μm ID and 60 cm long was etched by the following procedure: The capillary was rinsed with 1 mL HPLC grade deionized water. Then the capillary was filled with 0.1 M sodium hydroxide and flushed at room temperature for 30 minutes. Then, the base solution was removed by rinsing with 1 mL HPLC grade deionized water. The solution was changed to 1 mL 0.1 M HCl, and followed by another rinsing with 1 mL deionized water. The water was blown out with air.

N,N-Bis(carboxymethyl)-L-lysine hydrate (Sigma-Aldrich, Milwaukee, Wis., PN 14580) (0.300 g) was suspended in 4 mL dimethylformamide (DMF). After ten minutes, two mL N,N-di-isopropylethylamine (Sigma-Aldrich, Milwaukee, Wis., PN 496219) was added. After an additional ten minutes, 0.21 g (or ca. 200 μL) 3-glycidoxypropyltrimethoxysilane (Sigma-Aldrich, Milwaukee, Wis., PN 44,016-7) was added. The solution was heated to 75° C., and if the pH was less than 8, then more N,N-di-isopropylethylamine was added. The solution was reacted for 14-16 hours at 75° C.

A 1 mL syringe was filled with the solution prepared above, and any undissolved solids should not be introduced into the syringe directly but rather filtered through a 0.45 μm filter first. The solution was pumped through the capillary at 65° C. at a flow rate of 0.07 mL/hour for 10-12 hours. Then the capillary was rinsed with 2-3 mL deionized water and the capillary was stored in water.

The chelator capillary was flushed with water and converted to the Ni form with a 0.1 mM solution of NiSO$_4$ and flushed with water again. The capillary is ready to extract the his-tagged protein.

His-tagged GST standard (2.5 mg/mL) was used for demonstrating the functional activity of the Ni-NTA capillary surface. The his-tagged GST standard was prepared by transforming E. Coli BL21 DE3 competent cells (Stratagene, La Jolla, Calif., PN 200131) with a pET41a vector (Novagen, Madison, Wis., PN 70556-3). Transformation, inoculation, incubation, cell harvesting and centrifugation were performed exactly according to the cell manufacturer's instructions. The pelleted cells were lysed with Bugbuster protein extraction reagent (Novagen, Madison, Wis., PN 70584-3), which was used exactly according to the manufacturer's instructions to generate 3 mL of supernatant containing the his-tagged GST. This was combined with 3 mL of a 50% slurry of glutathione Sepharose 4 FastFlow (Amersham Biosciences, Piscataway, N.J., PN 17-5132-01), and the purification through the GST group proceeded exactly according to the manufacturer's instructions. The presence of this protein before and after glutathione purification was validated by SDS-PAGE. The purified protein fractions were pooled, dialyzed against 1×PBS (0.9% w/v NaCl, 10 mM sodium phosphate, pH 7.2) and freeze-dried by standard means. The addition of 2 mL deionized water resulted in 2 mL of 2.5 mg/mL his-tagged GST in 1×PBS.

In addition to these preparation procedures, this protein material was assayed for the presence of a functional and accessible 6×His fusion tag by loading 15 µL of the dialyzed stock protein solution onto 200 µL of Ni-NTA agarose (Qiagen, Santa Clarita, Calif., PN 30210). All Ni-NTA purification steps were performed exactly according to the manufacturer's instructions. The presence of his-tagged protein released from the Ni-NTA agarose was validated by SDS-PAGE.

Twenty µL of the 2.5 mg/mL his-tagged GST sample was aspirated into 1 meter of nickel-loaded NTA capillary, thus occupying roughly two-thirds of the 30 µL internal volume of the capillary. This 20 µL sample zone was visually monitored and pulled to the top of the capillary with a 50 µL syringe without allowing it to leave the capillary. This was allowed to incubate in the capillary at room temperature for five minutes, thus leaving 10 µL of internal volume unoccupied at the bottom of the capillary. The sample zone was then pushed to the bottom of the capillary in the same manner without allowing it to leave the capillary and was allowed to incubate in the capillary at room temperature for five minutes, thus leaving 10 µL of internal volume unoccupied at the top of the capillary. This process of incubating the sample zone at the top and bottom of the capillary was repeated twice for this same sample, followed finally by expelling the sample zone from the capillary with 1 mL of air flowing at 10-20 mL/min. This capillary was then washed with 10 mM $NaH_2PO_4$/10 mM $Na_2HPO_4$ buffer, pH 7 by passing 500 µL of the buffer through the capillary at 1 mL/min, followed by expelling of the buffer from the capillary with 1 mL of air flowing at 10-20 mL/min.

Ten µL of 200 mM imidazole eluent was aspirated into this same capillary, thus occupying roughly one-third of the 30 µL internal volume of the capillary. This 10 µL elution zone was visually monitored and pulled with a 50 µL syringe to the top of the capillary without allowing it to leave the capillary. This was allowed to incubate in the capillary at room temperature for one minute, thus leaving 20 µL of internal volume unoccupied at the bottom of the capillary. The elution zone was then pushed to the bottom of the capillary in the same manner without allowing it to leave the capillary and was allowed to incubate in the capillary at room temperature for one minute, thus leaving 20 µL of internal volume unoccupied at the top of the capillary. This process of incubating the elution zone at the top and bottom of the capillary was repeated twice for this same elution zone, followed by finally expelling and collecting the elution zone into a 0.5 mL Eppendorf vial with 1 mL of air flowing at 10-20 mL/min. This collected elution zone was combined with 10 µL of Bradford assay reagent (Pierce, Rockford, Ill., PN 23236), was allowed to incubate for ten minutes at room temperature, and an absorbance reading was taken of the sample at 595 nm with a SpectraPhysics detector (Spectra FOCUS forward optical scanning detector). Calibration was performed by measuring a 200 mM imidazole blank and 250 µg/mL his-tagged GST standard in 200 mM imidazole, each combined with equal volumes of the Bradford assay reagent. Analysis of the eluted sample against this calibration indicated that 0.8 µg of the his-tagged GST was trapped and eluted from the Ni-NTA capillary into 10 µL of 200 mM imidazole (corresponding to a concentration of 80 µg/mL his-tagged GST in the eluted zone).

Example 51

Extraction of Protein Complexes

Figure 9:
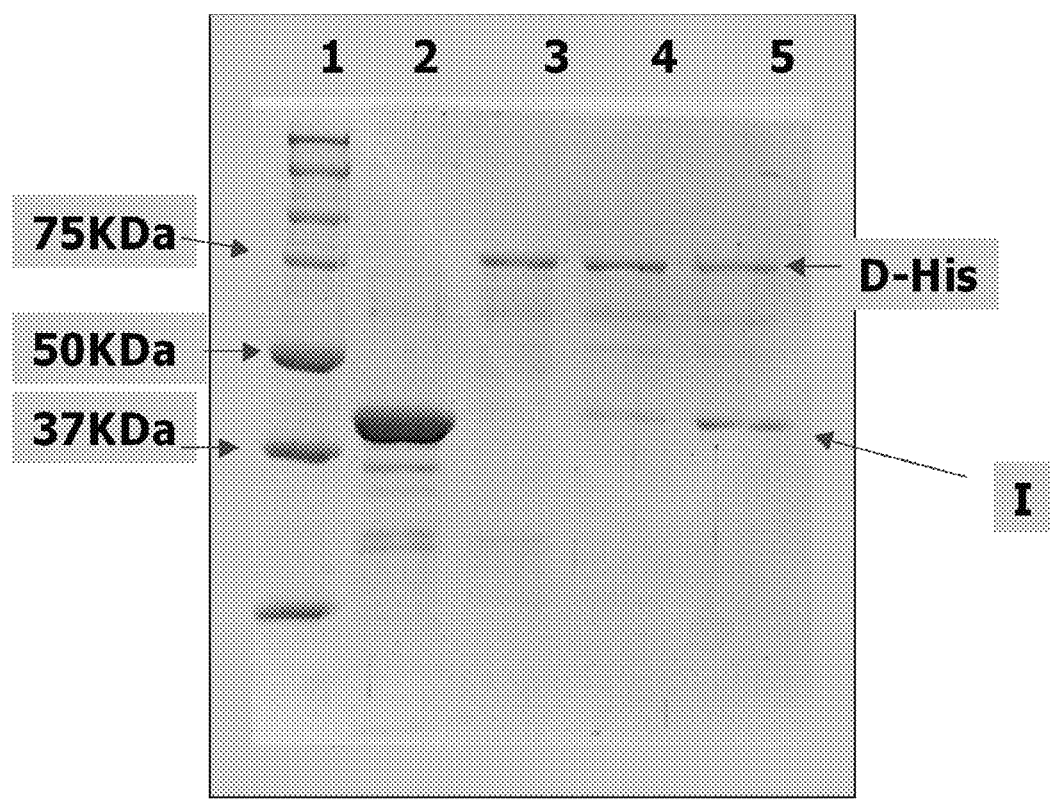
FIG. 9-12 are SDS-PAGE gels associated with Example 51.

His-tagged magnesium-protoporphyrin IX chelatase subunit D and untagged subunit I were expressed and purified using procedures based on the work of Jensen et al. (Biochem. J. 339:127-34 (1999)). The subunits were mixed in free solution in the presence of Mg-ATP. More particularly, 5 µL each of 10 µM D-His and 40 µM I were mixed together in presence of 12 mM $MgCl_2$+2 mM ATP in a buffer containing MOPS pH 7.7. In a separate reaction, the same subunits were mixed in the absence of Mg-ATP. The two reactions were then processed by extraction and elution off of a Ni-NTA extraction capillary. The processed reactions were analyzed by 12% SDS-PAGE (shown in FIG. 9). Lane 1 is MW markers, lane 2 is subunit I, lane 3 is his-tagged subunit D. Lane 4 is the processed Mg-ATP minus reaction, and lane 5 is the processed reaction conducted in the presence of Mg-ATP. Note that non-tagged I is extracted in the presence of tagged D, and that an increased amount of subunit I is extracted when the subunits are incubated in the presence of Mg-ATP.

Figure 10:
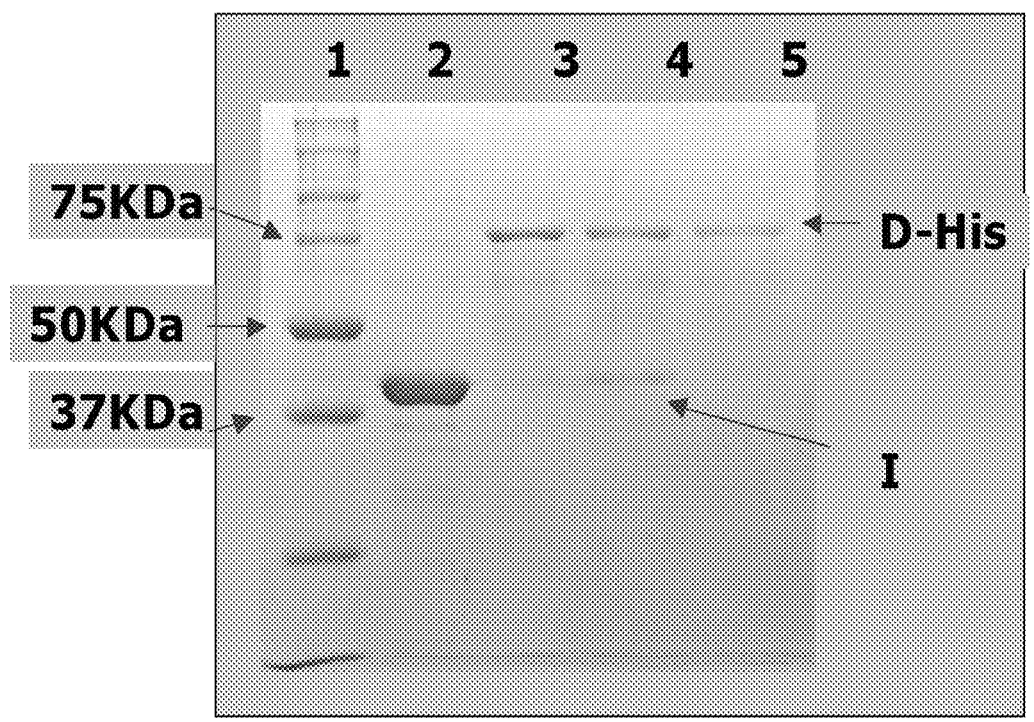

In another experiment, his-tagged subunit D was immobilized onto a Ni-NTA extraction capillary, and then untagged I was passed through the capillary either in the presence of absence of Mg-ATP. Bound material was then eluted and analyzed by SDS-PAGE (shown in FIG. 10). Lane 1 is MW markers, lane 2 is subunit I, lane 3 is his-tagged subunit D. Lane 4 is the eluted sample where I subunit was loaded in the presence of Mg-ATP, and lane 5 is the processed eluted sample where I subunit was loaded in the absence of Mg-ATP. Note the level of I bound in the presence of Mg-ATP.

Figure 11:
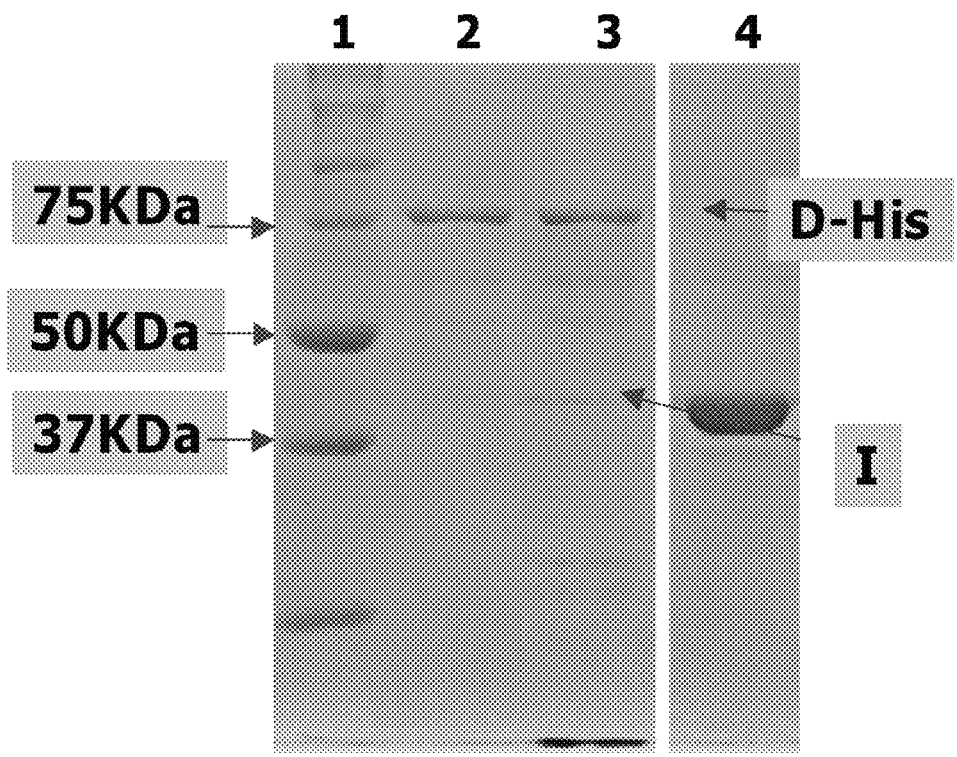

In another experiment, his-tagged subunit D and untagged subunit I were mixed in free solution in the presence of Mg-ATP and rabbit reticulocyte lysate. The reaction was then processed by extraction and elution off of a Ni-NTA extraction capillary. The processed reaction was analyzed by SDS-PAGE (shown in FIG. 11). Lane 1 is MW markers, lane 2 is his-tagged subunit D, lane 3 is the processed reaction, and lane 4 subunit I. The gel indicates that I is present in the reaction.

Figure 12:
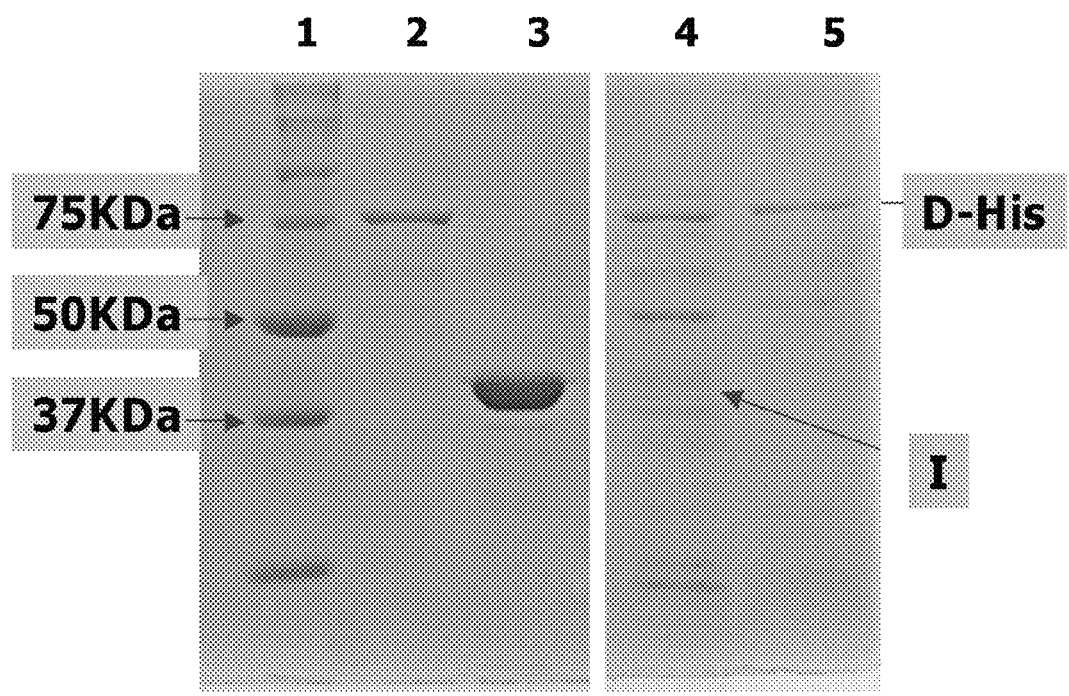

In another experiment, his-tagged subunit D and untagged subunit I were mixed in free solution in the presence of Mg-ATP and *E. coli* lysate. The same reaction was replicated in the absence of Mg-ATP. The reactions were then processed by extraction and elution off of a Ni-NTA extraction capillary. The processed reaction was analyzed by SDS-PAGE (shown in FIG. 12). Lane 1 is MW markers, lane 2 is his-tagged subunit D, and lane 3 is subunit I alone. Lane 4 is the processed reaction conducted in the presence of Mg-ATP, and lane 5 is the processed Mg-ATP minus reaction. Note the presence of a band corresponding to subunit I in lane 4.

Example 52

Antibody Screening with Label-Free Grating-Coupled SPR

Individual IgG antibody clones are expressed within hybridomas, where the hybridoma supernatant is passed through an open-tube separation capillary with ProG immobilized on its surface. Once the IgGs are trapped on the surface, the tube is washed with a suitable buffer (i.e. PBS), and all fluids are blown out. A very small volume slug (<1 µL) of 10 mM phosphoric acid (~pH2.3) is introduced to the tube, and is moved back and forth across the internal walls to desorb the IgG from the immobilized ProG. This is ejected from the tube, into an equal volume of phosphate buffer, bringing the pH to ~7. This is then ready for non-covalent spotting onto a GC-SPR array, where the surface chemistry is ProG covalently attached to MUA. In addition, the desorption/neutralization process can be performed within the spotting apparatus itself so that the antibodies are fully processed as part of a larger integrated chip preparation process.

Example 53

Phage Display Screening of Fabs with Label-Free Grating-Coupled SPR

Phage-derived clones for different Fab sequences are released as whole-cell bacterial lysates, where there are two fusion tags on the Fab—one for c-myc (for purification) and the other a terminal cysteine residue (for immobilization). The clarified lysate is passed through an open-tube separation capillary with ProG immobilized on its surface, and an anti-c-myc monoclonal or polyclonal antibody is bound by the ProG (a bifunctional linker covalently attaches the antibody to the ProG). Once the Fab is trapped by the anti-c-myc antibody on the inside tube wall, a very small volume slug (<1 μL) of 10 mM phosphoric acid (~pH 2.3) is introduced to the tube, and is moved back and forth across the internal walls to desorb the Fab from the immobilized anti-c-myc. This is ejected from the tube, into an equal volume of phosphate buffer, brining the pH to ~7. This is then ready for covalent spotting onto a GC-SPR array, where the surface chemistry is based upon the terminal cysteine's thiol group bonding with the gold surface of the GC-SPR chip (see attached poster presentation from HTS Biosystems). In addition, the desorption/neutralization process can be performed within the spotting apparatus itself so that the Fabs are fully processed as part of a larger integrated chip preparation process.

Example 54

Protein-Protein Interaction Screening by Fluorescence Imaging

Different recombinant yeast proteins are released as whole-cell lysates, where there are two fusion tags on every protein—one for GST (for purification) and the other a terminal 6-His tag (for immobilization). The clarified lysate is passed through an open-tube separation capillary with glutathione immobilized on its surface. Once the protein is trapped by the glutathione on the inside tube wall, a very small volume slug (<1 μL) of 20 mM glutathione is introduced into the tube, and is moved back and forth across the internal walls to desorb the protein (via competition for the GST). This is ejected from the tube, and is ready for non-affinity spotting onto a nickel-coated array surface through the 6-His tag. At this point the "target" protein that is being screened for its various interaction partners on the array is biotinylated and introduced to the array. Cy3-labeled streptavidin is introduced to the chip to detect those spots where the target bound, which is determined by standard fluorescence imaging. (For more details on these procedures, see attached paper from Snyder and colleagues).

Example 55

Quantitation Chip for Monitoring Protein Levels by Fluorescence Imaging

Purified antibodies for different cognate targets requiring quantitation are spotted onto a glass slide for passive adsorption to the surface. A clarified cell lysate is passed through an open-tube separation capillary with ProG immobilized on its surface, and an anti-phosphotyrosine (anti-pY) monoclonal or polyclonal antibody is bound by the ProG (a bifunctional linker covalently attaches the antibody to the ProG). Once the phosphorylated proteins are trapped by the anti-pY antibody on the inside tube wall, a very small volume slug (<1 μL) of 10 mM phosphoric acid (~pH 2.3) is introduced to the tube, and is moved back and forth across the internal walls to desorb the phosphoproteins from the immobilized anti-pY. This is ejected from the tube, into an equal volume of phosphate buffer, bringing the pH to ~7. These proteins are then labeled with either Cy5 or Cy3, and are presented in a very small (and enriched) volume to the aforementioned array for quantitation of the phosphorylated proteins. This process not only isolates and enriches the phosphoprotein fraction, but also eliminates any potentially confounding/interfering proteins such as albumin.

Example 56

Quantitation Chip for Monitoring Protein Levels in Serum by Chemiluminescence Imaging Purified antibodies for different cognate targets requiring quantitation are spotted onto a membrane for passive adsorption to the surface. A clarified serum sample is passed through a long, high-capacity open-tube separation capillary with Cibachron Blue immobilized on its surface, which will selectivity extract albumin from the serum. The resulting sample is then brought to the purified antibody array fro trapping of the cognate binders. A secondary antibody (for detection of the target) is labeled with biotin, and introduced to the array. Streptavidin-HRP fusion protein is added, after which chemiluminescence substrate is added (upon which the HRP reacts). The light-generating signals are collected with a cooled CCD camera. As a result of removing such a highly abundant protein as albumin, the signals will have greater specificity & reduced cross-reactivity between the antibody "matched pairs," which leads to lower background signals (improved detection limits) and enhanced accuracy.

Example 57

Nucleic Acid Aptamer Arrays for Quantitation of Serum- or Urine-Borne Markers

Purified aptamers for different cognate targets that bear terminal thiol groups are spotted onto a gold array surface, thus creating a covalent bond with that surface. A clarified serum sample is passed through a long, high-capacity open-tube separation capillary with Cibachron Blue immobilized on its surface, which will selectively extract albumin form the serum. The resulting sample is then brought to the purified aptamer array for trapping of the cognate binders. UV light results in covalent cross-linking of the specific targets to their specific aptamers, and non-specific binders are washed away. A universal protein stain is introduced to the covalently trapped proteins, and a fluorescence image is collected using various approaches. As a result of removing such a highly abundant protein as albumin, the signals will have greater specificity and reduced cross-reactivity between the antibody "matched pairs," which leads to lower background signals (improved detection limits) and enhanced accuracy.

Example 58

Purification of His-Tagged GST on Extraction Capillary Coated with a Three-Dimensional NTA Extraction Surface One meter extraction capillaries coated with a three-dimensional NTA extraction surface (internal volume of slightly higher than 30 μL) are prepared and charged as with nickel as described above. The capillaries are stored in 5 mM NiSO$_4$ in 10% methanol, preferably at 4° C. To prepare the capillaries for sample processing, the storage fluid is pushed from the capillary by means of a syringe. The capillaries are then flushed with PBS for 20 minutes to remove any excess methanol and nickel from the capillary.

The extraction process is conveniently implemented by a multiplexed automated or semi-automated system, such as those described in FIGS. 5-7 and commercially available from Phynexus, Inc. (San Jose, Calif.). 0.5 mL of sample is loaded by passing it back and forth four times through the capillary (total of 8 passages) by means of a syringe pump at a flow rate of 0.1-0.2 mL/min. The capillary is then washed with 2 exposures of 0.5 mL 10 mM imidazole in PBS at a flow rate of 0.2 mL/min. Any remaining wash solution is pushed out, and the capillary is purged by passing nitrogen through it at 50 psi for 1 minute. 15 μL of 500 mM imidazole eluent is pulled up to the top of the capillary (aspirated) at a flow rate of 0.06 mL/min. Since the total volume of capillary is about 30 μL, the top half of the capillary is filled with eluent and the lower half is filled with air. The eluent is allowed to incubate at this position for about 30 seconds, then is pushed down to the bottom of the capillary (infused) a flow rate of 0.06 mL/min, and allowed to incubate another 30 seconds. This process of aspiration and infusion is repeated a total of eight times, with the eluent cycling back and forth between the top and bottom sections of the capillary with the same flow rate and 30 second incubations. Finally the eluent is infused from the capillary, along with the processed his-GST.

While the invention has been described in connection with specific embodiments thereof, it will be understood that it is capable of further modifications and this application is intended to cover and variations, uses, or adaptations of the invention that follow, in general, the principles of the invention, including such departures from the present disclosure as come within known or customary practice within the art to which the invention pertains and as may be applied to the essential features hereinbefore set forth. Moreover, the fact that certain aspects of the invention are pointed out as preferred embodiments is not intended to in any way limit the invention to such embodiments.

What is claimed is:

1. A method for extracting a multi-protein complex comprising the steps of:
    a. introducing a sample solution comprising the multi-protein complex into an open extraction channel, wherein the inner surface of the open extraction channel is comprised of a solid phase extraction surface, wherein said multi-protein complex is comprised of at least a first protein and a second protein, whereby said multi-protein complex is adsorbed to said extraction surface;
    b. optionally passing a wash solution through the channel;
    c. purging the extraction channel with a gas in such a way that the extraction channel is substantially free of bulk liquid and wherein the extraction surface remains substantially solvated; and
    d. eluting the multi-protein complex by passing a desorption solution through the channel wherein the purified multi-protein complex retains biological activity.

2. The method of claim 1, wherein the extraction surface is comprised of an affinity binding agent selected from the group consisting of a chelated metal, a protein, an organic molecule or group, a sugar, and a nucleic acid.

3. The method of claim 2, wherein the extraction surface is 3-dimensional.

4. The method of claim 3, wherein the extraction channel is a capillary.

5. The method of claim 4, wherein the capillary is comprised of fused silica.

6. The method of claim 5, wherein the multi-protein complex is eluted with a solid phase extraction tube enrichment factor greater than 1.

7. The method of claim 3, wherein the multi-protein complex is eluted with a solid phase extraction tube enrichment factor greater than 1.

8. The method of claim 2, wherein the multi-protein complex is eluted with a solid phase extraction tube enrichment factor greater than 1.

9. The method of claim 1, wherein the extraction surface is 3-dimensional.

10. The method of claim 9, wherein the extraction channel is a capillary.

11. The method of claim 10, wherein the capillary is comprised of fused silica.

12. The method of claim 11, wherein the multi-protein complex is eluted with a solid phase extraction tube enrichment factor greater than 1.

13. The method of claim 9, wherein the multi-protein complex is eluted with a solid phase extraction tube enrichment factor greater than 1.

14. The method of claim 1, wherein the multi-protein complex is eluted with a solid phase extraction tube enrichment factor greater than 1.

* * * * *